(12) United States Patent
Crooke et al.

(10) Patent No.: US 6,329,146 B1
(45) Date of Patent: Dec. 11, 2001

(54) MASS SPECTROMETRIC METHODS FOR BIOMOLECULAR SCREENING

(75) Inventors: Stanley T. Crooke, Carlsbad; Richard Griffey, Vista; Steven Hofstadler, Oceanside, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/260,310

(22) Filed: Mar. 2, 1999

Related U.S. Application Data

(63) Continuation-in-part of application No. 09/076,206, filed on May 12, 1998.
(60) Provisional application No. 60/076,534, filed on Mar. 2, 1998.

(51) Int. Cl.$^7$ .................................................. C12Q 1/68
(52) U.S. Cl. ............................ 435/6; 435/91.2; 536/26.6
(58) Field of Search ..................... 435/6, 91.2; 536/26.6; 530/360

(56) References Cited

U.S. PATENT DOCUMENTS 5,571,902   11/1996   Ravikumar et al. ................. 536/22.1

FOREIGN PATENT DOCUMENTS

WO 89/12694   12/1989   (WO) .

OTHER PUBLICATIONS

Berendsen, Science, 282:642–43, Oct. 1998.*
Cheng, X. et al., "Electrospray Ionization with High Performance Fourier Transform Ion Cyclotron Resonance Mass Spectrometry for the Study of Noncovalent Biomolecular Complexes," *Techniques in Protein Chem. VII*, 1996,13–22.
Przybylski, M. et al., "Mass spectrometric approaches to molecular characterization of protein–nucleic acid interactions," *Toxicology Letts.*, 1995, 82/83, 567–575.
Sannes–Lowery, K.A. et al., "HIV–1 Tat Peptide Binding to TAR RNA by Electrospray Ionization Mass Spectrometry," *Anal. Chem.*, 1997, 69, 5130–5135.
Köster, H. et al., "A Strategy for rapid and efficient DNA sequencing by mass spectrometry," *Nature Biotechnology*, 1996, 14, 1123–1128.
Amster, "Fourier Transform Mass Spectrometry", *J. Mass Spectrom.*, 1996, 31, 1325–1337.
Anderegg et al., "Mass Spectrometric Characterization of a Protein—Ligand Interaction", *J. Am. Chem. Soc.*, 1995, 117, 1374–1377.
Baca et al., "Direct Observation of a Ternary Complex between the Dimeric Enzyme HIV–1 Protease and a Substrate–Based Inhibitor", *J. Am. Chem. Soc.*, 1992, 114, 3992–3993.

Baczynskyj et al., "Application of Thermally Assisted Electrospray Ionization Mass Spectrometry for Detection of Noncovalent Complexes of Bovine Serum Albumin with Growth Hormone Releasing Factor and Other Biologically Active Peptides", *Rapid Comm. Mass Spectrom.*, 1994, 8, 280–286.
Bayer et al., "Analysis of Double–Stranded Oligonucleotides by Electrospray Mass Spectrometry", *Anal. Chem.*, 1994, 66, 3858–3863.
Berson et al., "General Principles of Radioimmunoassay", *Clin. Chim. Acta*, 1968, 22, 51–60.
Bruce et al., "Bio–Affinity Characterization Mass Spectrometry", *Rapid Commun. Mass Spectrom.*, 1995, 9, 644–650.
Bruins et al., "Ion Spray Interface for Combined Liquid Chromatography/Atmospheric Pressure Ionization Mass Spectrometry", *Anal. Chem.*, 1987, 59, 2642–2646.
Busman et al., "Observation of Large Multimers in the Electrospray Ionization Mass Spectrometry of Peptides", *Rapid Commun. Mass Spectrom.*, 1994, 8, 211–216.
Cai et al., "Capillary electrohoresis—mass spectrometry",*J. Chromatogr.*, 667–692.
Cheng et al., "Using Electrospray Ionization FTICR Mass Spectrometry to Study Competitive Binding of Inhibitors to Carbonic Anhydrase", *J. Am. Chem. Soc.*, 1995, 117, 8859–8860.
Chu et al., "Affinity Capillary Electrophoresis",*Acc. Chem. Res.*, 1995, 28, 461–468.
Chu et al., "Using Affinity Capillary Electrophoresis to Identify the Peptide in a Peptide Library that Binds Most Tightly to Vancomycin",*J. Org. Chem.*, 1993, 58, 648–652.
Chu et al., "Affinity Capillary Electrophoresis—Mass Spectrometry for Screening Combinatorial Libraries", *J. Am. Chem. Soc.*, 1996, 118, 7827–7835.
Cohen et al., "Probing the solution structure of the DNA–binding protein Max by a combination of proteolysis and mass spectrometry", *Protein Sci.*, 1995, 4, 1088–1099.

(List continued on next page.)

Primary Examiner—Scott W. Houtteman
(74) Attorney, Agent, or Firm—Woodcock Washburn Kurtz Mackiewicz & Norris LLP

(57) ABSTRACT

The present invention provides methods for the determination of the structure of biomolecular targets, as well as the site and nature of the interaction between ligands and biomolecular targets. The present invention also provides methods for the determination of the relative affinity of a ligand for the biomolecular target it interacts with. Also provided are methods for screening ligand or combinatorial libraries of compounds against one or more than one biological target molecules. The methods of the invention also allow determination of the relative binding affinity of combinatorial and other compounds for a biomolecular target. The present invention further provides methods for the use of mass modifying tags for screening multiple biomolecular targets. In a preferred embodiment, ligands which have great specificity and affinity for molecular interaction sites on biomolecules, especially RNA can be identified. In preferred embodiments, such identification can be made simultaneously with libraries of ligands.

35 Claims, 33 Drawing Sheets

OTHER PUBLICATIONS

Doctycz et al., "Accumulation and Storage of Ionized Duplex DNA Molecules in a Quandrupole Ion Trap", *Anal. Chem.*, 1994, 66, 3416–3422.

Dunayevskiy et al., "Mass Spectrometric Identification of Ligands Selected from Combinatorial Libraries Using Gel Filtration", *Rapid Commun. Mass Spectrom.*, 1997, 11, 1178–1184.

Ecker et al., "Combinatorial Drug Discovery: Which Methods Will Produce the Greatest Value", *Biotech.*, 1995, 13, 351–360.

Erickson et al., "Macromolecular X–Ray Crystallography and NMR as Tools for Structure–based Drug Design", *Ann. Rep. Med. Chem.*, 1992, vol. 27, Ch. 29, 271–289.

Feng et al., "Analysis of Antibodies and Other Large Glycoproteins in the Mass Range of 150 000–200 000 Da by Electrospray Ionization Mass Spectrometry", *Anal. Chem.*, 1992, 64, 2090–2095.

Gale et al., "Observation of Duplex DNA–Drug Noncovalent Complexes by Electrospray Ionization Mass Spectrometry", *J. Am. Chem. Soc.*, 1994, 116, 6027–6028.

Ganem et al., "Detecting Noncovalent Complexes of Biological Macromolecules: New Applications of Ion–Spray Mass Spectrometry", *ChemTracts–Org. Chem.*, 1993, 6, 1–22.

Ganem et al., "Detection of Oligonucleotide Duplex Forms by Ion–Spray Mass Spectrometry", *Tetra. Lett.*, 1993, 34(9), 1445–1448.

Gao et al., "Screening Derivatized Peptide Libraries for Tight Binding Inhibitors to Carbonic Anhydrase II by Electrospray Ionization–Mass Spectrometry", *J. Med. Chem.*, 1996, 39, 1949–1955.

Glover et al., "Sequencing of Oligonucleotides Using High Performance Liquid Chromatography and Electrospray Mass Spectrometry", *Rapid Commun. Mass Spectrom.*, 1995, 9, 897–901.

Goodlett et al., "Direct Observation of a DNA Quadruplex by Electrospray Ionization Mass Spectrometry", *Biol. Mass Spectrom.*, 1993, 22, 181–183.

Greig et al., "Measurement of Macromolecular Binding Using Electrospray Mass Spectrometry. Determination of Dissocation Constants for Oligonucleotide—Serum Albumin Complexes", *J. Am. Chem. Soc.*, 1995, 117, 10765–10766.

Henion et al., "Mass Spectrometric Investigations of Drug–Receptor Interactions", *Ther. Drug Monitoring*, 1993, 15(6), 563–569.

Hillenkamp et al., "Matrix–Assisted Laser Desorption/Ionization Mass Spectrometry of Biopolymers", *Anal. Chem.*, 1991, 63(24), 1193A–1202A.

Hu et al., "Determining Calcium–binding Stoichiometry and Cooperativity of Parvalbumin and Calmodulin by Mass Spectrometry", *J. Mass Spectrom.*, 1995, 30, 1076–1079.

Huang et al., "Packed–Capillary Liquid Chromatography/Ion–Spray Tandem Mass Spectrometry Determination of Biomolecules", *Anal. Chem.*, 1991, 63, 732–739.

Huang et al., "LC/MS and LC/MS/MS Determination of Protein Tryptic Digests", *J. Am. Soc. Mass Spectrom.*, 1990, 1(2), 158–165.

Jefson, "Applications of NMR Spectroscopy to Protein Structure Determination", *Ann. Rep. Med. Chem.*, 1988, vol. 23, Ch. 28, 275–283.

Jensen et al., "Mass Spectrometric Characterization of UV–Crosslinked Protein–Nucleic Acid Complexes", *42nd ASMS Conf. On Mass Spectrom. and Allied Topics*, 1994, 923.

Jensen et al., "Direct Observation of UV–crosslinked Protein–Nucleic Acid Complexes by Matrix–assisted Laser Desorption Ionization Mass Spectrometry", *Rapid Commun. Mass Spectrom.*, 1993, 7, 496–501.

Jonsson et al., "Real–Time Biospecific Interaction Analysis Using Surface Plasmon Redonance and a Sensor Chip Technology", *Biotech.*, 1991. 11(5), 620–627.

Karlsson et al., "Kinetic analysis of monoclonal antibody––antigen interactions with a new biosensor based analytical system", *J. Immunol. Methods*, 1991, 145, 229–240.

Kassel et al., "Direct Coupling of an Automated 2–Dimenstional Microcolumn Affinity Chromatogrpahy–Capillary HPLC System with Mass Spectrometry for Biomolecular Analysis", in *Techniques in Protein Chemistry*, J.Crabb (ed.), Academic Press, San Diego, 1995, Ch. VI, 39–46.

Knight et al., "Electrospray Ionization Mass Spectrometry as a Mechanistic Tool: Mass of Human Leucocyte Elastase and a β–Lactam–Derived E–I Complex", *Biochem.*, 1993, 32 2031–2035.

Lane et al., "SPARC Is a Source of Copper–binding Peptides that Stimulate Angiogenesis", *J. Cell Biol.*, 1994, 125(4), 929–943.

Little et al., "Rapid Sequencing of Olignoucleotides by High–Resolution Mass Spectrometry", *J. Am. Chem. Soc.*, 1994, 116, 4893–4897.

Li et al., "Mass Spectrometric Studies on Noncovalent Dimers of Leucine Zipper Peptides", *J. Am. Chem. Soc.*, 1993, 115, 8409–8413.

Light–Wahl et al., "Observation of a Small Oligonucleotide Duplex by Electrospray Ionization Mass Spectrometry", *J. Am. Chem. Soc.*, 1993, 115, 803–804.

Light–Wahl et al., "Observation of the Noncovalent Quaternary Associations of Proteins by Electrospray Ionization Mass Spectrometry", *J. Am. Chem. Soc.*, 1994, 116, 5271–5278.

Light–Wahl et al., "Collisionally Activated Dissociation and Tandem Mass Spectrometry of Intact Hemoglobin β–Chain Variant Proteins with Electrospray Ionization", *Biol. Mass Spectrom.*, 1993, 22, 112–120.

Lim et al., "Recognition of Cell–wall Peptide Ligands by Vancomycin Group Antibiotics: Studies Using Ion Spray Mass Spectrometry", *J. Mass Spectrom.*, 1995, 30. 708–714.

Little et al., "Sequencing 50–mer DNAs Using Electrospray Tandem Mass Spectrometry and Complementary Fragmentation Methods", *J. Am. Chem. Soc.*, 1995, 117, 6783–6784.

Little et al., "Infrared Multiphoton Dissociation of Large Multiply Charged Ions for Biomolecule Sequencing", *Anal. Chem.*, 1994, 66, 2809–2815.

Little et al., "Verification of 50 –to 100–mer DNA and RNA sequences with high–resolution mass spectrometry", *Proc. Natl. Acad. Sci. USA*, 1995, 92, 2318–2322.

Loo, "Bioanalytical Mass Spectrometry: Many Flavors to Choose", *Bioconjugate Chem.*, 1995, 6, 644–665.

Loo, "Observation of Large Subunit Protein Complexes by Electrospray Ionization Mass Spectrometry", *J. Mass Spectrom.*, 1995, 30, 180–183.

Loo et al., "Use of Electrospray Ionization Mass Spectrometry to Probe Antisense Peptide Interactions", *Biol. Mass Spectrom.*, 1994, 23, 6–12.

Loo et al., "Interaction of Angiotensin Peptides and Zinc Metal Ions Probed by Electrospray Ioniztion Mass Spectrometry", *J. Am. Mass Spectrom.*, 1994, 5(11), 959–965.

Marshall et al., "Fouriere Transform Ion Cyclotron Resonance Mass Spectrometry: The Teenage Years", *Anal. Chem.*, 1991, 63(4), A215–A229.

McLuckey et al., "Tandem Mass Spectrometry of Small, Multiply Charged Oligonucleotides", *J. Am. Soc. Mass Spectrom.*, 1992, 3(1), 60–70.

McLuckey et al., "Decompositions of Multiply Charged Oligonucleotide Anions", *J. Am. Chem. Soc.*, 1993, 115, 12085–12095.

Nelson et al., "Mass Determination of Human Immunoglobulin IgM Using Matrix–assisted Laser Desorption/Ionization Time–of–flight Mass Spectromety", *Rapid Commun. Mass Spectrom.*, 1994, 8, 627–631.

Ni et al., "Interpretation of Oligonucleotide Mass Spectra for Determinationof Sequence Using Electrospray Ionization and Tandem Mass Spectrometry", *Anal. Chem.*, 1996, 68, 1989–1999.

Nordhoff et al., "Direct Mass Spectrometric Sequencing of Low–picomole Amounts of Oligodeoxynucleotides with up to 21 Bases by Matric–assisted Laser Desorption/Ionization Mass Spectrometry", *J. Mass Spectrom.*, 1995, 30, 99–112.

Pieles et al., "Matrix–assisted laser desorption ionization time–of–flight mass spectrometry: a powerful tool for the mass and sequence analysis of natural and modified oligonucleotides", *Nucl. Acid Res.*, 1993, 21(14), 3191–3196.

Rossomando et al., "Identification of Tyr–185 as the site of tyrosine autophosphorylation of recombinant mitogen–activated protein kinase p42$^{mapk}$", *Proc. Natl. Acad. Sci USA*, 1992, 89, 5779–5783.

Shaler et al., "Analysis of Enzymatic DNA Sequencing Reactions by Matrix–assisted Laser Desorption/Ionization Time–of–flight Mass Spectrometry", *Rapid Commun. Mass Spectrom.*, 1995, 9, 942–947.

Smith et al., "The Observation of Non–covalent Interactions in Solution by Electrospray Ionization Mass Spectrometry: Promise, Pitfalls and Prognosis", *J. Biol. Mass Spectrom.*, 1993, 22, 493–501.

Smith et al., "New Developments in Biochemical Mass Spectrometry: Electrospray Ionization", *Anal. Chem.*, 1990, 62, 882–899.

Sternberg et al., "Display of peptides and proteins on the surface of bacteriophageλ", *Proc. Natl. Acad. Sci. USA*, 1995, 92, 1609–1613.

Udenfriend et al., "Scintillation Proximity Assay: A Sensitive and Continuous Isotopic Method for Monitoring Ligand/Receptor and Antigen/Antibody Interactions", *Anal. Biochem.*, 1987, 161, 494–500.

Winger et al., "High–Resolution Accurate Mass Measurements of Biomolecules Using a New Electrospray Ionization Ion Cyclotron Resonance Mass Spectrometer", *J. Am. Soc. Mass Spectrom.*, 1993, 4(7), 566–577.

Witkowska et al., "Mass Spectrometric Analysis of a Native Zinc–Finger Structure: The Glucocorticoid Receptor DNA Binding Domain", *J. Am. Chem. Soc.*, 1995, 117(12), 3319–3324.

Cheng et al., "Electrospray Ionization with High Performance Fourier Transform Ion Cyclotron Resonance Mass Spectrometry for the Study of Noncovalent Biomolecular Complexes", in *Techniques in Protein Chemistry*, 1996, vol. 7, 13–21.

Biemann, "Mass Spectrometry of Peptides and Proteins", *Ann. Rev. Biochem.*, 1992, 61, 977–1010.

Bowers et al., "Mass Spectrometry: Recent Advances and Future Directions", *J. Phys. Chem.*, 1996, 100, 12897–12910.

Burlingame et al., "Mass Spectrometry", *J. Anal. Chem.*, 1998, 70, 647R–716R.

Bryan, "Mechanisms of Action of Aminoglycoside Antibiotics", in *New Dimensions in Antimicrobial Therapy*, Root, R.K. et al. (eds.), Churchill Livingstone, New York, 1984, vol. 1, Ch. 2, 17–36.

Cheng et al., "Direct measurement of oligonucleotide binding stoichiometry of gene V protein by mass spectrometry", *Proc. Natl. Acad. Sci USA*, 1996, 93, 7022–7027.

Crain et al., "Applications of mass spectrometry to the characterization of oligonucleotides and nucleic acids", *Curr. Opin. Bioetechnol.*, 1998, 9, 25–34.

De Stasio et al., "Mutations in 16S ribosomal RNA disrupt antibiotic—RNA interactions", *EMBO J.*, 1989, 8, 1213–1216.

Fitzgerald et al., "Probing the oligomeric structure of an enzyme by electrospray ionization time–of–flight mass spectrometry", *Proc. Natl. Acad. Sci. USA*, 1996, 93, 6851–6856.

Fourmy et al., "Structure of the A Site of *Escherichia coli* 16S Ribosomal RNA Complexed with an Aminoglycoside Antibiotic", *Science*, 1996, 2/4, 1367–1371.

Fourmy et al., "Paromomycin Binding Induces a Local Conformational Change in the A–site of 16 S rRNA", *J. Mol. Biol.*, 1998, 277, 333–345.

Gale et al., "Characterization of Noncovalent Complexes Formed between Minor Groove Binding Molecules and Duplex DNA by Electrospray Ionization—Mass Spectrometry", *J. Am. Soc. Mass Spectrometry*, 1995, 6, 1154–1164.

Ganguly et al., "Studies of the Ras–GDP and Ras–GTP Noncovalent Complexes by Electrospray Mass Spectrometry", *Tetrahedron*, 1993, 49(36), 7985–7996.

Griffey et al., "Detection of base pair mismatches in duplex DNA and RNA oligonucleotides using electrospray mass spectrometry", *Proc. SPIE–Int. Soc. Opt. Eng.*, 1997, 2985, 82–86.

Jorgensen et al., "Direct Determination of Solution Binding Constants for Noncovalent Complexes between Bacterial Cell Wall Peptide Analogues and Vancomycin Group Antibiotics by Electrospray Ionization Mass Spectrometry", *Anal. Chem.*, 1998, 70, 4427–4432.

Loo, "Study Noncovalent Protein Complexes by Electrospray Ionization Mass Spectrometry", *Mass Spectrometry Reviews*, 1997, 16, 1–23.

Marshall et al., "Fourier Transform Ion Cyclotron Resonance Mass Spectrometry: A Primer", *Mass Spectrom. Rev.*, 1998, 17, 1–35.

Miyaguchi et al., "An antibiotic motif of an RNA fragment derived from the A–site–related region of *Escherichia coli* 16A rRNA", *Nucl. Acids Res.*, 1996, 24(19), 3700–3706.

Recht et al., "RNA Sequence Determinants for Aminoglycoside Binding to an A–site rRNA Model Oligonucleotide", *J. Mol. Biol.*, 1996, 262, 421–436.

Smith et al., "New mass spectrometric methods for the study of noncovalent associations of biopolymers", *Chem. Soc. Rev.*, 1997, 26, 191–202.

Wang et al., "Specificity of Aminoglycoside Binding to RNA Constructs Derived from the 16S rRNA Decoding Region and the HIV–RRE Activator Region", *Biochem.*, 1997, 36, 768–779.

Wincott et al., "Synthesis, deprotection, analysis and purification of RNA and ribozymes", *Nucl. Acids Res.*, 1995, 23(14), 2677–2684.

Wong et al., "Specificity of aminoglycoside antibiotics for the A–site of the decoding region of ribosomal RNA", *Chem. Biol.*, 1998, 5(7), 397–406.

Dunayevskly, Y. M., et al., "Simultaneous Measurement of nineteen binding constants of peptides to vancomycin using affinity capillary electrophoresis–mass spectrometry," *J. Med. Chem.*, 1998, 41, 1201–1204.

Griffey, R. H., et al., "Determinants of aninoglycoside–binding specificity for rRNA by using mass spectrometry," *Proc. Natl. Acad. Sci. USA*, 1999, 96, 10129–10133.

Kempen, E. C., et al., "A method for the determination of binding constants by electrospray ionization mass spectrometry," *Anal. Chem.*, 2000, 72, 5411–5416.

* cited by examiner

Figure 1. Sequence and structure of 27mer RNA target

Figure 2 MS/MS of control (upper) control + paromomycin (lower)

Figure 8. MS Fragmentation of DNA:DNA duplexes

Figure 9. MS Fragmentation of DNA:RNA duplexes

Simultaneous Screening of 16S A-site and 18S A-site Model RNAs Against Aminoglycoside Mixture

Figure 32

| n | name | apex | start | stop | height | area |
|---|---|---|---|---|---|---|
| 1 | 16628-1.-4 | 1783.710 | 1783.635 | 1783.834 | 14.55 | 1.63 |
| 2 | 16628-1.-3 | 1783.909 | 1783.834 | 1783.972 | 60.04 | 5.15 |
| 3 | 16628-1.-2 | 1784.109 | 1784.021 | 1784.184 | 115.60 | 11.14 |
| 4 | 16628-1.-1 | 1784.308 | 1784.233 | 1784.383 | 167.34 | 15.89 |
| 5 | 16628-1.0 | 1784.508 | 1784.433 | 1784.620 | 133.94 | 14.74 |
| 6 | 16628-1.1 | 1784.707 | 1784.620 | 1784.795 | 136.60 | 13.38 |
| 7 | 16628-1.2 | 1784.907 | 1784.795 | 1784.982 | 82.63 | 8.56 |
| 8 | 16628-1.3 | 1785.107 | 1785.032 | 1785.219 | 57.81 | 5.21 |
| 9 | 16628-1.4 | 1785.306 | 1785.232 | 1785.369 | 32.31 | 2.65 |
| 10 | 16628-1.5 | 1785.506 | 1785.456 | 1785.569 | 17.67 | 1.12 |
| 11 | 16628.10019.-4 | 1906.974 | 1906.874 | 1907.031 | 12.63 | 1.00 |
| 12 | 16628.10019.-3 | 1907.173 | 1907.045 | 1907.273 | 22.54 | 2.11 |
| 13 | 16628.10019.-2 | 1907.373 | 1907.287 | 1907.444 | 33.86 | 2.91 |
| 14 | 16628.10019.-1 | 1907.572 | 1907.456 | 1907.701 | 34.87 | 3.30 |
| 15 | 16628.10019.0 | 1907.772 | 1907.701 | 1907.843 | 20.93 | 1.55 |
| 16 | 16628.10019.1 | 1907.972 | 1907.900 | 1908.043 | 21.03 | 1.55 |
| 17 | 16628.10019.2 | 1908.157 | 1908.066 | 1908.271 | 10.97 | 0.90 |
| 18 | 16628.-4 | 2229.874 | 2229.679 | 2230.029 | 27.51 | 4.87 |
| 19 | 16628.-3 | 2230.146 | 2230.029 | 2230.263 | 111.72 | 16.23 |
| 20 | 16628.-2 | 2230.380 | 2230.263 | 2230.516 | 225.18 | 32.39 |
| 21 | 16628.-1 | 2230.633 | 2230.516 | 2230.770 | 260.66 | 40.90 |
| 22 | 16628.0 | 2230.887 | 2230.770 | 2231.023 | 287.24 | 41.95 |
| 23 | 16628.1 | 2231.140 | 2231.023 | 2231.257 | 242.23 | 34.17 |

MASS SPECTROMETRIC METHODS FOR BIOMOLECULAR SCREENING

CROSS-REFERENCE TO RELATED APPLICATIONS

This application is a Continuation-In-Part of U.S. patent application Ser. No. 09/076,206 filed May 12, 1998, and Provisional Application Ser. No. 60/076,534 filed Mar. 2, 1998, the disclosures of which are incorporated herein by reference in their entirety.

FIELD OF THE INVENTION

The present invention is directed to methods for the use of mass spectrometry for the determination of the structure of a biomolecule especially a nucleic acid target, the site(s) of interaction between ligands and the target, the relative binding affinity of ligands for the target and other useful information. The present invention also provides methods for the use of mass spectrometry for screening chemical mixtures or libraries, especially combinatorial libraries, for individual compounds that bind to a selected target and can be used in pharmaceuticals, veterinary drugs, agricultural chemicals industrial chemicals and otherwise. The present invention is further directed to methods for screening multiple targets simultaneously against, e.g. a combinatorial library of compounds.

A further aspect of the invention provides methods for determining the interaction between one or a plurality of molecular species, especially "small" molecules and a molecular interaction site on a nucleic acid, especially an RNA.

BACKGROUND OF THE INVENTION

The process of drug discovery is changing at a fast pace because of the rapid progress and evolution of a number of technologies that impact this process. Drug discovery has evolved from what was, several decades ago, essentially random screening of natural products, into a scientific process that not only includes the rational and combinatorial design of large numbers of synthetic molecules as potential bioactive agents, such as ligands, agonists, antagonists, and inhibitors, but also the identification, and mechanistic and structural characterization of their biological targets, which may be polypeptides, proteins, or nucleic acids. These key areas of drug design and structural biology are of tremendous importance to the understanding and treatment of disease. However, significant hurdles need to be overcome when trying to identify or develop high affinity ligands for a particular biological target. These include the difficulty surrounding the task of elucidating the structure of targets and targets to which other molecules may be bound or associated, the large numbers of compounds that need to be screened in order to generate new leads or to optimize existing leads, the need to dissect structural similarities and dissimilarities between these large numbers of compounds, correlating structural features to activity and binding affinity, and the fact that small structural changes can lead to large effects on biological activities of compounds.

Traditionally, drug discovery and optimization have involved the expensive and time-consuming, and therefore slow, process of synthesis and evaluation of single compounds bearing incremental structural changes. When using natural products, the individual components of extracts had to be painstakingly separated into pure constituent compounds prior to biological evaluation. Further, all compounds had to be carefully analyzed and characterized prior to in vitro screening. These screens typically included evaluation of candidate compounds for binding affinity to their target, competition for the ligand binding site, or efficacy at the target as determined via inhibition, cell proliferation, activation or antagonism end points. Considering all these facets of drug design and screening that slow the process of drug discovery, a number of approaches to alleviate or remedy these matters, have been implemented by those involved in discovery efforts.

One way in which the drug discovery process is being accelerated is by the generation of large collections, libraries, or arrays of compounds. The strategy of discovery has moved from selection of drug leads from among compounds that are individually synthesized and tested to the screening of large collections of compounds. These collections may be from natural sources (Sternberg et al., *Proc. Natl. Acad. Sci. USA*, 1995, 92, 1609–1613) or generated by synthetic methods such as combinatorial chemistry (Ecker and Crooke, BioTechnology, 1995, 13, 351–360 and U.S. Pat. No. 5,571,902, incorporated herein by reference). These collections of compounds may be generated as libraries of individual, well-characterized compounds synthesized, e.g. via high throughput, parallel synthesis or as a mixture or a pool of up to several hundred or even several thousand molecules synthesized by split-mix or other combinatorial methods. Screening of such combinatorial libraries has usually involved a binding assay to determine the extent of ligand-receptor interaction (Chu et al., *J. Am. Chem. Soc.*, 1996, 118, 7827–35). Often the ligand or the target receptor is immobilized onto a surface such as apolymer bead or plate. Following detection of a binding event, the ligand is released and identified. However, solid phase screening assays can be rendered difficult by non-specific interactions.

Whether screening of combinatorial libraries is performed via solid-phase, solution methods or otherwise, it can be a challenge to identify those components of the library that bind to the target in a rapid and effective manner and which, hence, are of greatest interest. This is a process that needs to be improved to achieve ease and effectiveness in combinatorial and other drug discovery processes. Several approaches to facilitating the understanding of the structure of biopolymeric and other therapeutic targets have also been developed so as to accelerate the process of drug discovery and development. These include the sequencing of proteins and nucleic acids (Smith, in Protein Sequencing Protocols, Humana Press, Totowa, N.J., 1997; Findlay and Geisow, in Protein Sequencing: A Practical Approach, IRL Press, Oxford, 1989; Brown, in DNA Sequencing, IRL Oxford University Press, Oxford, 1994; Adams, Fields and Venter, in Automated DNA Sequencing and Analysis, Academic Press, San Diego, 1994). These also include elucidating the secondary and tertiary structures of such biopolymers via NMR (Jefson, Ann. Rep. in Med. Chem., 1988, 23, 275; Erikson and Fesik, Ann. Rep. in Med. Chem., 1992, 27, 271–289), X-ray crystallography (Erikson and Fesik, Ann. Rep. in Med. Chem., 1992, 27, 271–289) and the use of computer algorithms to attempt the prediction of protein folding (Copeland, in Methods of Protein Analysis: A Practical Guide to Laboratory Protocols, Chapman and Hall, New York, 1994; Creighton, in Protein Folding, W. H. Freeman and Co., 1992). Experiments such as ELISA (Kemeny and Challacombe, in ELISA and other Solid Phase Immunoassays: Theoretical and Practical Aspects; Wiley, New York, 1988) and radioligand binding assays (Berson and Yalow, Clin. Chim. Acta, 1968,22, 51–60; Chard, in "An Introduction to Radioimmunoassay and Related Techniques," Elsevier press, Amsterdam/New York, 1982), the use of surface-plasmon resonance (Karlsson, Michaelsson and Mattson, J. Immunol. Methods, 1991, 145, 229; Jonsson et al., Biotechniques, 1991, 11, 620), and scintillation proximity assays (Udenfriend, Gerber and Nelson, Anal. Biochem., 1987, 161, 494–500) are being used to understand the nature of the receptor-ligand interaction.

All of the foregoing paradigms and techniques are now available to persons of ordinary skill in the art and their understanding and mastery is assumed herein.

Likewise, advances have occurred in the chemical synthesis of compounds for high-throughput biological screening. Combinatorial chemistry, computational chemistry, and the synthesis of large collections of mixtures of compounds or of individual compounds have all facilitated the rapid synthesis of large numbers of compounds for in vitro screening. Despite these advances, the process of drug discovery and optimization entails a sequence of difficult steps. This process can also be an expensive one because of the costs involved at each stage and the need to screen large numbers of individual compounds. Moreover, the structural features of target receptors can be elusive.

One step in the identification of bioactive compounds involves the determination of binding affinity of test compounds for a desired biopolymeric or other receptor, such as a specific protein or nucleic acid or combination thereof. For combinatorial chemistry, with its ability to synthesize, or isolate from natural sources, large numbers of compounds for in vitro biological screening, this challenge is magnified. Since combinatorial chemistry generates large numbers of compounds or natural products, often isolated as mixtures, there is a need for methods which allow rapid determination of those members of the library or mixture that are most active or which bind with the highest affinity to a receptor target.

From a related perspective, there are available to the drug discovery scientist a number of tools and techniques for the structural elucidation of biologically interesting targets, for the determination of the strength and stoichiometry of target-ligand interactions, and for the determination of active components of combinatorial mixtures.

Techniques and instrumentation are available for the sequencing of biological targets such as proteins and nucleic acids (e.g. Smith, in Protein Sequencing Protocols, 1997 and Findlay and Geisow, in Protein Sequencing: A Practical Approach, 1989) cited previously. While these techniques are useful, there are some classes and structures of biopolymeric target that are not susceptible to such sequencing efforts, and, in any event, greater convenience and economy have been sought. Another drawback of present sequencing techniques is their inability to reveal anything more than the primary structure, or sequence, of the target.

While X-ray crystallography is a very powerful technique that can allow for the determination of some secondary and tertiary structure of biopolymeric targets (Erikson and Fesik, Ann. Rep. in Med. Chem., 1992, 27, 271–289), this technique can be an expensive procedure and very difficult to accomplish. Crystallization of biopolymers is extremely challenging, difficult to perform at adequate resolution, and is often considered to be as much an art as a science. Further confounding the utility of X-ray crystal structures in the drug discovery process is the inability of crystallography to reveal insights into the solution-phase, and therefore the biologically relevant, structures of the targets of interest.

Some analysis of the nature and strength of interaction between a ligand (agonist, antagonist, or inhibitor) and its target can be performed by ELISA (Kemeny and Challacombe, in ELISA and other Solid Phase Immunoassays: 1988), radioligand binding assays (Berson and Yalow, Clin. 1968, Chard, in "An Introduction to Radioimmunoassay and Related Techniques," 1982), surface-plasmon resonance (Karlsson, Michaelsson and Mattson, 1991, Jonsson et al, Biotechniques, 1991), or scintillationproximity assays (Udenfriend, Gerber and Nelson, Anal. Biochem., 1987), all cited previously. The radioligand binding assays are typically useful only when assessing the competitive binding of the unknown at the biding site for that of the radioligand and also require the use of radioactivity. The surface-plasmon resonance technique is more straightforward to use, but is also quite costly. Conventional biochemical assays of binding kinetics, and dissociation and association constants are also helpful in elucidating the nature of the target-ligand interactions.

When screening combinatorial mixtures of compounds, the drug discovery scientist will conventionally identify an active pool, deconvolute it into its individual members via resynthesis, and identify the active members via analysis of the discrete compounds. Current techniques and protocols for the study of combinatorial libraries against a variety of biologically relevant targets have many shortcomings. The tedious nature, high cost, multi-step character, and low sensitivity of many of the above-mentioned screening technologies are shortcomings of the currently available tools. Further, available techniques do not always afford the most relevant structural information—the structure of a target in solution, for example. Instead they provide insights into target structures that may only exist in the solid phase. Also, the need for customized reagents and experiments for specific tasks is a challenge for the practice of current drug discovery and screening technologies. Current methods also fail to provide a convenient solution to the need for deconvolution and identification of active members of libraries without having to perform tedious re-syntheses and re-analyses of discrete members of pools or mixtures.

Therefore, methods for the screening and identification of complex chemical libraries especially combinatorial libraries are greatly needed such that one or more of the structures of both the target and ligand, the site of interaction between the target and ligand, and the strength of the target-ligand interaction can be determined. Further, in order to accelerate drug discovery, new methods of screening combinatorial libraries are needed to provide ways for the direct identification of the bioactive members from a mixture and to allow for the screening of multiple biomolecular targets in a single procedure. Straightforward methods that allow selective and controlled cleavage of biopolymers, while also analyzing the various fragments to provide structural informnation, would be of significant value to those involved in biochemistry and drug discovery and have long been desired. Also, it is preferred that the methods not be restricted to one type of biomolecular target, but instead be applicable to a variety of targets such as nucleic acids, peptides, proteins and oligosaccharides.

OBJECTS OF THE INVENTION

A principal object of the present invention is to provide novel methods for the determination of the structure of biomolecular targets and ligands that interact with them and to ascertain the nature and sites of such interactions.

A further object of the invention is to determine the structural features of biomolecular targets such as peptides, proteins, oligonucleotides, and nucleic acids such as the primary sequence, the secondary and folded structures of biopolymers, and higher order tertiary and quaternary structures of biomolecules that result from intramolecular and intermolecular interactions.

Yet another object of the invention is to determine the site(s) and nature of interaction between a biomolecular target and a binding ligand or ligands. The binding ligand may be a "small" molecule, a biomolecule such as a peptide, oligonucleotide or oligosaccharide, a natural product, or a member of a combinatorial library.

A further object of the invention is to determine the relative binding affinity or dissociation constant of ligands that bind to biopolymer targets. Preferably, this gives rise to a determination of relative binding affinities between a biopolymer such as an RNA/DNA target and ligands e.g. members of combinatorially synthesized libraries.

A further object of the invention is to determine the absolute binding affinity or dissociation constant of ligands that bind to biopolymer targets.

A still further object of the present invention is to provide a general method for the screening of combinatorial libraries comprising individual compounds or mixtures of compounds against a biomolecular target such as a nucleic acid, so as to determine which components of the library bind to the target.

An additional object of the present invention is to provide methods for the determination of the molecular weight and structure of those members of a combinatorial library that bind to a biomolecular target.

Yet another object of the invention is to provide methods for screening multiple targets such as nucleic acids, proteins, and other biomolecules and oligomers simultaneously against a combinatorial library of compounds.

A still further object of the invention is to ascertain the specificity and affinity of compounds, especially "small" organic molecules to bind to or interact with molecular interaction sites of biological molecules, especially nucleic acids such as RNA. Such molecules may be and preferably do form ranked hierarchies of ligands and potential ligands for the molecular interaction sites, ranked in accordance with predicted or calculated likelihood of interaction with such sites.

Another object of the present invention is to alleviate the problem of peak overlap in mass spectra generated from the analysis of mixtures of screening targets and combinatorial or other mixtures of compounds. In a preferred embodiment, the invention provides methods to solve the problems of mass redundancy in combinatorial or other mixtures of compounds, and also provides methods to solve the problem of mass redundancy in the mixture of targets being screened.

A further object of the invention is to provide methods for determining the binding specificity of a ligand for a target in comparison to a control. The present invention facilitates the determination of selectivity, the identification of non-specific effects and the elimination of non-specific ligands from further consideration for drug discovery efforts.

The present invention provides, inter alia, a series of new methods and applications for the determination of the structure and nature of binding of ligands to a wide variety of biomolecular targets. This new approach provides structural information for screening combinatorial libraries for drug lead discovery.

SUMMARY OF THE INVENTION

One aspect of the invention is a method to determine the structure of biomolecular targets such as nucleic acids using mass spectrometry. The method provides not only the primary, sequence structure of nucleic acid targets, but also information about the secondary and tertiary structure of nucleic acids, RNA and DNA, including mismatched base pairs, loops, bulges, kinks, and stem structures. This can be accomplished in accordance with one embodiment by incorporating deoxynucleotide residues or other modified residues into an oligoribonucleotide at specific sites followed by selective cleavage of these hybrid RNA/DNA nucleic acids in a mass spectrometer. It has now been found that electrospray ionization of the nucleic acid, cleavage of the nucleic acid, and subsequent tandem MSn spectrometry affords a pattern of fragments that is indicative of the nucleic acid sequence and structure. Cleavage is dependent on the sites of incorporation of the deoxynucleotide or other foreign residues and the secondary structure of the nucleic acid. This method therefore provides mass spectral data that identifies the sites and types of secondary structure present in the sequence of nucleic acids.

When the present methods are performed on a mixture of the biomolecular target and a ligand or molecule that binds to the target, it is possible to ascertain both the extent of interaction and the location of this interaction between ligand and biomolecule. The binding of the ligand to the biomolecule protects the binding site on the biomolecule from facile cleavage during mass spectrometry. Therefore, comparison of ESI-MS$^n$ mass spectra generated, using this method, for RNA/DNA in the presence and the absence of a binding ligand or drug reveals the location of binding. This altered cleavage pattern is clearly discerned in the mass spectrum and correlated to the sequence and structure of the nucleic acid. Thus, the absolute binding affinity of the test ligand can be determined by the methods of the present invention. Comparison of the abundance of the nucleic acid-ligand noncovalent complex ion to the abundance of a similar complex ion generated from a standard compound (such as paromomycin for the 16S RNA A site ) whose binding affinity is known, allows for the determination of relative binding affinity of the test ligand.

The methods of this invention can be used for the rapid screening of large collections of compounds. It is also possible to screen mixtures of large numbers of compounds that are generated via combinatorial or other means. When a large mixture of compounds is exposed to a biomolecular target, such as a nucleic acid, a small fraction of ligands may exhibit some binding affinity to the nucleic acid. The actual number of ligands that may be detected as binders is based on the concentration of the nucleic acid target, the relative concentrations of the components of the combinatorial mixture, and the absolute and relative binding affinities of these components. The method is capable of separating different noncovalent complexes, using techniques such as selective ion trapping, or accumulation and analyzing each complex for the structure and identity of the bound ligand using collisionally activated dissociation or MSn experiments. The methods of this invention, therefore, can not only serve as methods to screen combinatorial libraries for molecules that bind to biomolecular targets, but can also provide, in a straightforward manner, the structural identity of the bound ligands. In this manner, any mass redundancy in the combinatorial library does not pose a problem, as the methods can provide high resolution molecular masses and also able to discern differences between the different structures of ligands of identical molecular mass using tandem methods.

In accordance with preferred embodiments, a target biomolecule such as an RNA having a molecular interaction site, is presented with one or more ligands or suspected ligands for the interaction site under conditions such that interaction or binding of the ligand to the molecular interaction site can occur. The resulting complex, which may be of one or even hundreds of individual complexes of ligands with the RNA or other biomolecule, is then subjected to mass spectrometric evaluation in accordance with the invention. "Preparative" mass spectrometry can isolate individual complexes which can then be fragmented under controlled conditions within the mass spectrometric environment for subsequent analysis. In this way, the nature and degree, or absolute binding affinity, of binding of the ligands to the molecular interaction site can be ascertained. Identification of specific, strong binding ligands can be made and those selected for use either as therapeutics, agricultural, industrial or other chemicals, or the same used as lead compounds for subsequent modification into improved forms for such uses.

A further application of the present invention is the use of mass spectrometric methods for the simultaneous screening of multiple biomolecular targets against combinatorial libraries or mixtures of compounds. This rather complex screening procedure is made possible by the combined power of the mass spectrometric methods used and the way in which the screening is performed. When screening multiple target nucleic acids, for example, mass redundancy is a concern, especially if two or more targets are of similar sequence composition or mass. This problem is alleviated by the present invention, by using special mass modifying, molecular weight tags on the different nucleic acid targets being studied. These mass modifying tags are typically large molecular weight, non-ionic polymers including but not limited to, polyethylene glycols, polyacrylamides and dextrans, that are available in many different sizes and weights, and which may be attached at one or more of many different possible sites on nucleic acids. Thus similar nucleic acid targets may be differentially tagged and now be readily differentiated, in the mass spectrum, from one another by their distinctly different mass to charge ratios (m/z signals). Using the methods of this invention, screening efforts can be significantly accelerated because multiple targets can now be screened simultaneously against mixtures of large numbers of compounds.

Another related advantage of the methods of this invention is the ability to determine the specificity of binding interactions between a new ligand and a biomolecular target. By simultaneously screening a target nucleic acid, for example, and one or more control nucleic acids against a combinatorial library or a specific ligand, it is possible to ascertain, using the methods of this invention, whether the ligand binds specifically to only the target nucleic acids, or whether the binding observed with the target is reproduced with control nucleic acids and is therefore non-specific.

The methods of the invention are applicable to the study of a wide variety of biomolecular targets that include, but are not limited to, peptides, proteins, receptors, antibodies, oligonucleotides, RNA, DNA, RNA/DNA hybrids, nucleic acids, oligosaccharides, carbohydrates, and glycopeptides. The molecules that may be screened by using the methods of this invention include, but are not limited to, organic or inorganic, small to large molecular weight individual compounds, mixtures and combinatorial libraries of ligands, inhibitors, agonists, antagonists, substrates, and biopolymers, such as peptides, nucleic acids or oligonucleotides. The mass spectrometric techniques which can be used in the methods of the invention include, but are not limited to, $MS^n$, collisionally activated dissociation (CAD) and collisionally induced dissociation (CID) and infrared multiphoton dissociation (IRMPD). A a variety of ionization techniques may be used including, but not limited to, electrospray, MALDI and FAB. The mass detectors used in the methods of this invention include, but are not limited to, FTICR, ion trap, quadrupole, magnetic sector, time of flight (TOF), Q-TOF, and triple quadrupole. The methods of this invention may also use "hyphenated" techniques such as, but not limited to, LC/MS and CE/MS, all as described more fully hereinafter.

BRIEF DESCRIPTION OF THE DRAWINGS

FIG. 32 depicts data tabulated and stored in a relational database.

SUMMARY OF EXEMPLARY MASS SPECTROMETRIC TECHNIQUES

Figure 1:
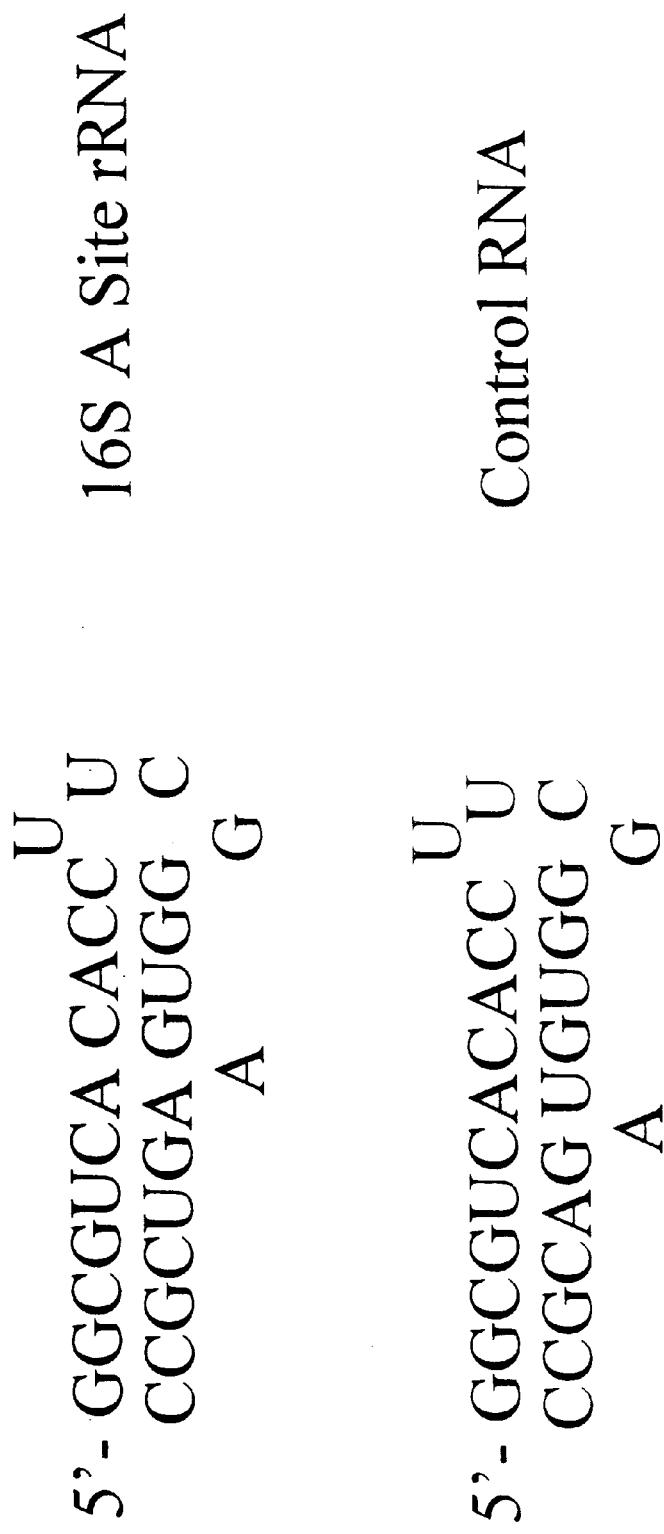
FIG. 1 shows the sequence and structure of the 27-mer RNA target corresponding to the 16S rRNA A-site.

Mass spectrometry (MS) is a powerful analytical tool for the study of molecular structure and interaction between small and large molecules. The current state-of-the-art in MS is such that less than femtomole quantities of material can be readily analyzed using mass spectrometry to afford information about the molecular contents of the sample. An accurate assessment of the molecular weight of the material may be quickly obtained, irrespective of whether the sample's molecular weight is several hundred, or in excess of a hundred thousand, atomic mass units or Daltons (Da). It has now been found that mass spectrometry can elucidate significant aspects of important biological molecules. One reason for the utility of MS as an analytical tool in accordance with the invention is the availability of a variety of different MS methods, instruments, and techniques which can provide different pieces of information about the samples.

One such MS technique is electrospray ionization mass spectrometry (ESI-MS) (Smith et al., Anal. Chem., 1990, 62, 882–899; Snyder, in Biochemical and biotechnological applications of electrospray ionization mass, American Chemical Society, Washington, D.C., 1996; Cole, in Electrospray ionization mass spectrometry: fundamentals, instrumentation, Wiley, New York, 1997). ESI produces highly charged droplets of the sample being studied by gently nebulizing the sample solution in the presence of a very strong electrostatic field. This results in the generation of highly charged droplets that shrink due to evaporation of the neutral solvent and ultimately lead to a "Coulombic explosion" that affords multiply charged ions of the sample material, typically via proton addition or abstraction, under mild conditions. ESI-MS is particularly useful for very high molecular weight biopolymers such as proteins and nucleic acids greater than 10 kDa in mass, for it affords a distribution of multiply-charged molecules of the sample biopolymer without causing any significant amount of fragmentation. The fact that several peaks are observed from one sample, due to the formation of ions with different charges, contributes to the accuracy of ESI-MS when determining the molecular weight of the biopolymer because each observed peak provides an independent means for calculation of the molecular weight of the sample. Averaging the multiple readings of molecular weight so obtained from a single ESI-mass spectrum affords an estimate of molecular weight that is much more precise than would be obtained if a single molecular ion peak were to be provided by the mass spectrometer. Further adding to the flexibility of ESI-MS is the capability to obtain measurements in either the positive or negative ionization modes.

In recent years electrospray ionization mass spectrometry (ESI-MS) has grown extensively as an analytical technique due to its broad applicability for analysis of macromolecules, including proteins, nucleic acids, and carbohydrates. Bowers, et al., *Journal of Physical Chemistry*, 1996, 100, 12897–12910; Burlingame, et al., *J. Anal. Chem.*, 1998, 70, 647R–716R; Biemann, *Ann. Rev. Biochem.*, 1992, 61, 977–1010; and Crain, et al., *Curr. Opin. Biotechnol*, 1998, 9, 25–34. One of the most significant developments in the field has been the observation, under appropriate solution conditions and analyte concentrations, of specific non-covalently associated macromolecular complexes that have been promoted into the gas-phase intact. Loo, *Mass Spectrometry Reviews*, 1997, 16, 1–23; Smith, et al, *Chemical Society Reviews*, 1997, 26, 191–202; Ens, et al, Standing, K. G. and Chernushevich, I. V. Editors, *New Methods for the Study of Biomolecular Complexes* (*Proceedings of the NATO Advanced Research Workshop*, held Jun. 16–20, 1996, in Alberta, Canada In: *NATO ASI Ser., Ser. C*, 1998; 510; Kluwer, Dordrecht, Neth., 1998. Recent examples include multimeric proteins (Fitzgerald, et al., *Proc. Natl. Acad. Sci. USA*, 1996, 93, 6851–6856), enzyme-ligand complexes (Ganguly, et al., *Tetrahedron*, 1993, 49, 7985–7996), protein-DNA complexes (Cheng, et al, *Proc. Nat'l. Acad. Sci. U.S.A.*, 1996, 93, 7022–7027), multimeric DNA complexes (Griffey, et al., *Proc. SPIE-Int. Soc. Opt. Eng.*, 1997,2985,82–86), and DNA-drug complexes (Gale, et al., *JACS*, 1994, 116, 6027–6028), the disclosures of which are incorporated herein by reference in their entirety.

Smith and co-workers have demonstrated that under competitive binding conditions in solution, ESI-MS measurements of enzyme-ligand mixtures yield gas-phase ion abundances that correlate with measured solution-phase dissociation constants (KD). Cheng, et al., *JACS*, 1995, 117, 8859–8860, the disclosure of which is incorporated herein by reference in its entirety. They were able to rank the binding affinities of a 256-member library of modified benzenesulfonamide inhibitors to carbonic anhydrase. Levels of free and bound ligands and substrates can be quantified directly from their relative abundances as measured by ESI-MS and that these measurements can be used to quantitatively determine molecular dissociation constants that agree with solution measurements. Jorgensen and co-workers have demonstrated that the relative ion abundance of non-covalent complexes formed between D- and L-tripeptides and vancomycin group antibiotics can be used to measure solution binding constants. Jorgensen, et al., *Anal. Chem.*, 1998, 70, 4427–4432, the disclosure of which is incorporated herein by reference in its entirety. Griffey and co-workers have shown that tandem ESI-MS methods can be used to determine the binding sites for small molecules that bind to RNA targets. Gale, et al., *Journal of the American Society for Mass Spectrometry*, 1995, 6, 1154–1164, the disclosure of which is incorporated herein by reference in its entirety.

Fourier transform ion cyclotron resonance mass spectrometry (FT-ICR MS) can resolve very small mass differences providing determination of molecular mass with unparalleled precision and accuracy. Marshall, et al, *Mass Spectrom. Rev.*, 1998, 17, 1–35. Because each small molecule with a unique elemental composition carries an intrinsic mass label corresponding to its exact molecular mass, identifying closely related library members bound to a macromolecular target requires only a measurement of exact molecular mass. The target and potential ligands do not require radiolabeling, fluorescent tagging, or deconvolution via single compound re-synthesis. Furthermore, adjustment of the concentration of ligand and target allows ESI-MS assays to be run in a parallel format under competitive or non-competitive binding conditions. Signals can be detected from complexes with dissociation constants ranging from <10 nM to ~100 mM.

Small molecules that bind to structured regions of RNA can exhibit therapeutic effects. For example, aminoglycoside antibiotics inhibit bacterial growth by disrupting essential RNA-protein and RNA-RNA interactions. De Stasio, et al., *EEMBO J*, 1989, 8, 1213–6 and Bryan, L. E. In *New dimensions in antimicrobial therapy*; Root, R. K., Sande, M. A., Eds., Churchill Livingstone, New York, 1984; Vol. 1, pp 17–35. Paromomycin, one of the most widely studied aminoglycosides, binds to the decoding region of the prokaryotic 16S rRNA (the A-site) with a ~200 nM $K_D$ and induces misreading of the genetic code during translation. Wong, et al, *Chem. Biol.*, 1998, 5, 397–406. However, the features of the interaction between RNAs and aminoglycosides that provide binding specificity are poorly characterized. In this work we employ ESI-FTICR to detect specific interactions between two closely related model RNA constructs corresponding to the decoding sites of the prokaryotic and eukaryotic ribosomes and individual members of a collection of aminoglycoside antibiotics.

Matrix-Assisted Laser Desorption/Ionization Mass Spectrometry (MALDI-MS) is another method that can be used for studying biomolecules (Hillenkamp et al., Anal. Chem., 1991, 63, 1193A–1203A). This technique ionizes high molecular weight biopolymers with minimal concomitant fragmentation of the sample material. This is typically accomplished via the incorporation of the sample to be analyzed into a matrix that absorbs radiation from an incident UV or IR laser. This energy is then transferred from the matrix to the sample resulting in desorption of the sample into the gas phase with subsequent ionization and minimal fragmentation. One of the advantages of MALDI-MS over ESI-MS is the simplicity of the spectra obtained as MALDI spectra are generally dominated by singly charged species. Typically, the detection of the gaseous ions generated by MALDI techniques, are detected and analyzed by determining the time-of-flight (TO) of these ions. While MALDI-TOF MS is not a high resolution technique, resolution can be improved by making modifications to such systems, by the use of tandem MS techniques, or by the use of other types of analyzers, such as Fourier transform (FT) and quadrupole ion traps.

Fourier transform mass spectrometry (FTMS) is an especially useful analytical technique because of its ability to make mass measurements with a combination of accuracy and resolution that is superior to other MS detection techniques, in connection with ESI or MALDI ionization (Amster, J. Mass Spectrom., 1996, 31, 1325–1337). Further it maybe used to obtain high resolution mass spectra of ions generated by any of the other ionization techniques. The basis for FTMS is ion cyclotron motion, which is the result of the interaction of an ion with a unidirectional magnetic field. The mass-to-charge ratio of an ion (m/q or m/z) is determined by a FTMS instrument by measuring the cyclotron frequency of the ion. The insensitivity of the cyclotron frequency to the kinetic energy of an ion is one of the fumdamental reasons for the very high resolution achievable with FTMS. FTMS is an excellent detector in conventional or tandem mass spectrometry, for the analysis of ions generated by a variety of different ionization methods including ESI and MALDI, or product ions resulting from collisionally activated dissociation (CAD).

Collisionally activated dissociation (CAD), also known as collision induced dissociation (CID), is a method by which analyte ions are dissociated by energetic collisions with neutral or charged species, resulting in fragment ions which can be subsequently mass analyzed. Mass analysis of fragment ions from a selected parent ion can provide certain sequence or other structural information relating to the parent ion. Such methods are generally referred to as tandem mass spectrometry (MS or MS/MS) methods and are the basis of the some of the MS based biomolecular sequencing schemes being employed today.

FTICR-MS, like ion trap and quadrupole mass analyzers, allows selection of an ion that may actually be a weak non-covalent complex of a large biomolecule with another molecule (Marshall and Grosshans, Anal. Chem., 1991, 63, A215–A229; Beu et al., J. Am. Soc. Mass Spectrom., 1993, 4, 566–577; Winger et al., J. Am. Soc. Mass Spectrom., 1993,4, 566–577); (Huang and Henion, Anal. Chem., 1991, 63, 732–739), or hyphenated techniques such as LC-MS (Bruins, Covey and Henion, Anal. Chem., 1987, 59, 2642–2646 Huang and Henion, J. Am. Soc. Mass Spectrom., 1990, 1, 158–65; Huang and Henion, Anal. Chem., 1991, 63, 732–739) and CE-MS (Cai and Henion, J. Chromatogr., 1995, 703, 667–692) experiments. FTICR-MS has also been applied to the study of ion-molecule reaction pathways and kinetics.

So-called "Hyphenated" techniques can be used for structure elucidation because they provide the dual features of separation and mass detection. Such techniques have been used for the separation and identification of certain components of mixtures of compounds such as those isolated from natural products, synthetic reactions, or combinatorial chemistry. Hyphenated techniques typically use a separation method as the first step; liquid chromatography methods such as HPLC, microbore LC, microcapillary LC, or capillary electrophoresis are typical separation methods used to separate the components of such mixtures. Many of these separation methods are rapid and offer high resolution of components while also operating at low flow rates that are compatible with MS detection. In those cases where flow rates are higher, the use of 'megaflow' ESI sources and sample splitting techniques have facilitated their implementation with on-line mass spectrometry. The second stage of these hyphenated analytical techniques involves the injection of separated components directly into a mass spectrometer, so that the spectrometer serves as a detector that provides information about the mass and composition of the materials separated in the first stage. While these techniques are valuable from the standpoint of gaining an understanding of the masses of the various components of multicomponent samples, they are incapable of providing structural detail. Some structural detail, however, may be ascertained through the use of tandem mass spectrometry, e.g., hydrogen/deuterium exchange or collision induced disassociation.

Typically, tandem mass spectrometry ($MS^n$) involves the coupled use of two or more stages of mass analysis where both the separation and detection steps are based on mass spectrometry. The first stage is used to select an ion or component of a sample from which further structural information is to be obtained. This selected ion is then fragmented by (CID) or photodissociation. The second stage of mass analysis is then used to detect and measure the mass of the resulting fragments or product ions. The advent of FTICR-MS has made a significant impact on the utility of tandem, $MS^n$ procedures because of the ability of FTICR to select and trap specific ions of interest and its high resolution and sensitivity when detecting fragment ions. Such ion selection followed by fragmentation routines can be performed multiple times so as to essentially completely dissect the molecular structure of a sample. A two-stage tandem MS experiment would be called a MS-MS experiment while an n-stage tandem MS experiment would be referred to as a $MS^n$ experiment. Depending on the complexity of the sample and the level of structural detail desired, $MS^n$ experiments at values of n greater than 2 may be performed.

Ion trap-based mass spectrometers are particularly well suited for such tandem experiments because the dissociation and measurement steps are temporarily rather than spatially separated. For example, a common platform on which tandem mass spectrometry is performed is a triple quadrupole mass spectrometer. The first and third quadrupoles serve as mass filters while the second quadrupole serves as a collision cell for CAD. In a trap based mass spectrometer, parent ion selection and dissociation take place in the same part of the vacuum chamber and are effected by control of the radio frequency wavelengths applied to the trapping elements and the collision gas pressure. Hence, while a triple quadrupole mass analyzer is limited to two stages of mass spectrometry (i.e. MS/MS), ion trap-based mass spectrometers can perform $MS^n$ analysis in which the parent ion is isolated, dissociated, mass analyzed and a fragment ion of interest is isolated, further dissociated, and mass analyzed and so on. A number of $MS^4$ procedures and higher have appeared in the literature in recent years and can be used here. (Cheng et al., Techniques in Protein Chemistry, VII, pp. 13–21).

ESI and MALDI techniques have found application for the rapid and straightforward determination of the molecular weight of certain biomolecules (Feng and Konishi, Anal. Chem., 1992, 64, 2090–2095; Nelson, Dogruel and Williams, Rapid Commun. Mass Spectrom., 1994, 8, 627–631). These techniques have been used to confirm the identity and integrity of certain biomolecules such as peptides, proteins, oligonucleotides, nucleic acids, glycoproteins, oligosaccharides and carbohydrates. Further, these MS techniques have found biochemical applications in the detection and identification of post-translational modifications on proteins. Verification of DNA and RNA sequences that are less than 100 bases in length has also been accomplished using ESI with FTMS to measure the molecular weight of the nucleic acids (Little et al, Proc. Natl. Acad. Sci. USA, 1995, 92, 2318–2322).

ESI tandem MS has been used for the study of high molecular weight proteins, for peptide and protein sequencing, identification of post-translational modifications such as phosphorylation, sulfation or glycosylation, and for the study of enzyme mechanisms (Rossomando et al., Proc. Natl. Acad. Sci. USA, 1992, 89, 5779–578; Knight et al., Biochemistry, 1993, 32, 2031–2035). Covalent enzyme-intermediate or enzyme-inhibitor complexes have been detected using ESI and analyzed by ESI-MS to ascertain the site(s) of modification on the enzyme. The literature has shown examples of protein sequencing where the multiply charged ions of the intact protein are subjected to collisionally activated dissociation to afford sequence informative fragment ions (Light-Wahl et al., Biol. Mass Spectrom., 1993, 22, 112–120). ESI tandem MS has also been applied to the study of oligonucleotides and nucleic acids (Ni et al, Anal. Chem., 1996, 68, 1989–1999; Little, Thannhauser and McLafferty, Proc. Natl. Acad. Sci., 1995, 92, 2318–2322).

While tandem ESI mass spectra of oligonucleotides are of ten complex, several groups have successfully applied ESI tandem MS to the sequencing of large oligonucleotides (McLuckey, Van Berkel and Glish, J. Am. Soc. Mass Spectrom., 1992, 3, 60–70; McLuckey and Habibigoudarzi, J. Am. Chem. Soc.,1993, 115, 12085–12095; Little et al, J. Am. Chem. Soc., 1994, 116, 4893–4897). General rules for the principal dissociation pathways of oligonucleotides, as formulated by McLuckey (McLuckey, Van Berkel and Glish, J. Am. Soc. Mass Spectrom., 1992, 3, 60–70; Mcluckey and Habibigoudarzi, J. Am. Chem. Soc., 1993, 115, 12085–12095), have assisted interpretation of mass spectra of oligonucleotides, and include observations of fragmentation such as, for example, the stepwise loss of base followed by cleavage of the 3'-C—O bond of the relevant sugar. Besides the use of ESI with tandem MS for oligonucleotide sequencing, two other mass spectrometric methods are also available: mass analysis of products of enzymatic cleavage of oligonucleotides (Pieles et al., Nucleic Acids Res., 1993, 21, 3191–3196; Shaler et al, Rapid Commun. Mass Spectrom., 1995, 9, 942–947; Glover et al., Rapid Commun. Mass Spectrom., 1995, 9, 897–901), and the mass analysis of fragment ions arising from the initial ionization/desorption event, without the use of mass selection techniques (Little et al., Anal. Chem., 1994, 66, 2809–2815; Nordhoffet al., J. Mass Spectrom., 1995, 30, 99–112; Little et al., J. Am. Chem. Soc., 1994,116, 4893–4897; Little and McLafferty, J. Am. Chem. Soc., 1995, 117, 6783–6784). While determining the sequence of deoxyribonucleic acids (DNA) is possible using ESI-MS and CED techniques (McLuckey, Van Berkel and Olish, J. Am. Soc. Mass Spectrom., 1992, 3, 60–70; McLuckey and Habibigoudarzi, J. Am. Chem. Soc., 1993, 115, 12085–12095), the determination of RNA sequence is much more difficult. Thus while small RNA, such as 6-mers, have been sequenced (McCloskey et al., J. Am. Chem. Soc., 1993, 115, 12085–1095), larger RNA have been difficult to sequence using mass spectrometry.

Electrospray mass spectrometry has been used to study biochemical interactions of biopolymers such as enzymes, proteins and nucleic acids with their ligands, receptors, substrates or inhibitors. While interactions that lead to covalent modification of the biopolymer have been studied for some time, those interactions that are of a non-covalent nature have been particularly difficult to study heretofore by methods other than kinetic techniques. It is now possible to yield information on the stoichiometry and nature of such non-covalent interactions from mass spectrometry. MS can provide information about the interactions between biopolymers and other molecules in the gas phase; however, experiments have demonstrated that the data so generated can be reflective of the solution phase phenomena from which the mass spectra were generated.

ESI is a gentle ionization method that results in no significant molecular fragmentation and preserves even weakly bound complexes between biopolymers and other molecules so that they are detected intact with mass spectrometry. A variety of non-covalent complexes of biomolecules have been studied using ESI-MS and reported in the literature (Loo, Bioconjugate Chemistry, 1995, 6, 644–665; Smith et al, J. Biol. Mass Spectrom. 1993, 22, 493–501; Li et al., J. Am. Chem. Soc., 1993, 115, 8409–8413). These include the peptide-protein complexes (Busman et al., Rapid Commun. Mass Spectrom., 1994, 8,211–216; Loo, Holsworth and Root-Bernstein, Biol. Mass Spectrom., 1994, 23, 6–12; Anderegg and Wagner, J. Am. Chem. Soc., 1995, 117, 1374–1377; Baczynskyj, Bronson and Kubiak., Rapid Commun. Mass Spectrom., 1994, 8, 280–286), interactions of polypeptides and metals (Loo, Hu and Smith, J. Am. Soc. Mass Spectrom., 1994, 5, 959–965; Hu and Loo, J. Mass Spectrom., 1995, 30, 1076–1079; Witkowska et al, J. Am. Chem. Soc.,1995, 117, 3319–3324; Lane et al., J. Cell Biol., 1994, 125, 929–943), protein-small molecule complexes (Ganem and Henion, ChemTracts-Org. Chem., 1993, 6, 1–22; Henion et al., Ther. Drug Monit., 1993, 15, 563–569; Baca and Kent, J. Am. Chem. Soc., 1992, 114, 3992–3993), the study of the quaternary structure of multimeric proteins (Baca and Kent, J. Am. Chem. Soc., 1992, 114, 3992–3993; Light-Wahl, Schwartz and Smith, J. Am. Chem. Soc., 1994, 116, 5271–5278; Loo, J. Mass Spectrom., 1995, 30, 180–183), and the study of nucleic acid complexes (Light-Wahl et al, J. Am. Chem. Soc., 1993, 115, 803–804; Gale et al, J. Am. Chem. Soc., 1994, 116, 6027–6028; Goodlett et al., Biol. Mass Spectrom., 1993, 22, 181–183; Ganem, Li and Henion, Tet. Lett., 1993, 34, 1445–1448; Doctycz et al., Anal. Chem., 1994, 66, 3416–3422; Bayer et al., Anal. Chem., 1994, 66, 3858–3863; Greig et al., J. Am. Chem. Soc., 1995, 117, 10765–766).

While data generated and conclusions reached from ESI-MS studies for weak non-covalent interactions generally reflect, to some extent, the nature of the interaction found in the solution-phase, it has been pointed out in the literature that control experiments are necessary to rule out the possibility of ubiquitous non-specific interactions (Smith and Light-Wahl, Biol. Mass Spectrorm, 1993, 22, 493–501). Somehave applied the use of ESI-MS and MALDI-MS to the study of multimeric proteins for the gentleness of the electrospray/desorption process allows weakly bound complexes, held together by hydrogen bonding, hydrophobic and/or ionic interactions, to remain intact upon transfer to the gas phase. The literature shows that not only do ESI-MS data from gas-phase studies reflect the non-covalent interactions found in solution, but that the strength of such interactions may also be determined. The binding constants for the interaction of various peptide inhibitors to src SH2 domain protein, as determined by ESI-MS, were found to be consistent with their measured solution phase binding constants (Loo, Hu and Thanabal, Proc. 43$^{rd}$ ASMS Conf. on Mass Spectrom. and Allied Topics, 1995). ESI-MS has also been used to generate Scatchard plots for measuring the binding constants of vancomycin antibiotics with tripeptide ligands (Lim et al., J. Mass Spectrom., 1995, 30, 708–714).

Similar experiments have been performed to study noncovalent interactions of nucleic acids. Both ESI-MS and MALDI-MS have been applied to study the non-covalent interactions of nucleic acids and proteins. While MALDI does not typically allow for survival of an intact non-covalent complex, the use of crosslinking methods to generate covalent bonds between the components of the complex allows for its use in such studies. Stoichiometry of interaction and the sites of interaction have been ascertained for nucleic acid-protein interactions (Jensen et al., Rapid Commun. Mass Spectrom., 1993, 7, 496–501; Jensen et al., 42$^{nd}$ ASMS Conf. on Mass Spectrom. and Allied Topics, 1994, 923). The sites of interaction are typically determined by proteolysis of either the non-covalent or covalently crosslinked complex (Jensen et al., Rapid Commun. Mass Spectrom., 1993, 7, 496–501; Jensen et al., $_{42}{}^{nd}$ASMS Conf on Mass Spectrom. and Allied Topics, 1994, 923; Cohen et al., Protein Sci., 1995, 4, 1088–1099). Comparison of the mass spectra with those generated from proteolysis of the protein alone provides information about cleavage site accessibility or protection in the nucleic acid-protein complex and, therefore, information about the portions of these biopolymers that interact in the complex.

Electrospray mass spectrometry has also been effectively used for the determination of binding constants of noncovalent macromolecular complexes such as those between proteins and ligands, enzymes and inhibitors, and proteins and nucleic acids. Greig et al. (J. Am. Chem. Soc., 1995, 117, 10765–10766) have reported the use of ESI-MS to determine the dissociation constants ($K_D$) for oligonucleotide-bovine serum albumin (BSA) complexes. The $K_D$ values determined by ESI-MS were reported to match solution $K_D$ values obtained using capillary electrophoresis.

Cheng et al. (J. Am. Chem. Soc., 1995, 117, 8859–8860) have reported the use of ESI-FTICR mass spectrometry as a method to determine the structure and relative binding constants for a mixture of competitive inhibitors of the enzyme carbonic anhydrase. Using a single ESI-FTICR-MS experiment these researchers were able to ascertain the relative binding constants for the noncovalent interactions between inhibitors and the enzyme by measuring the relative abundances of the ions of these noncovalent complexes. Further, the $K_D$s so determined for these compounds paralleled their known binding constants in solution. The method was also capable of identifying the structures of tight binding ligands from small mixtures of inhibitors based on the high resolution capabilities and multistep dissociation mass spectrometry afforded by the FTICR technique. In a related study, Gao et al. (J. Med. Chem., 1996, 39, 1949–55) have reported the use of ESI-FTICR-MS to screen libraries of soluble peptides in a search for tight binding inhibitors of carbonic anhydrase II. Simultaneous identification of the structure of a tight binding peptide inhibitor and determination of its binding constant was performed. The binding affinities determined from mass spectral ion abundance were found to correlate well with those determined in solution experiments. Further, the applicability of this technique to drug discovery efforts is limited by the lack of information generated with regards to sites and mode of such noncovalent interactions between a protein and ligands.

Also, these methods discuss, and appear to be limited to, the study of ligand interactions with proteins. The suitability of this method of mass spectrometric analysis of binding and dissociation constants for the study of noncovalent interactions of oligonucleotides, nucleic acids, such as RNA and DNA, and other biopolymers has not been described in the literature.

The drug discovery process has recently been revolutionized by the introduction of high throughput synthesis and combinatorial chemistry which afford collections and mixtures of large numbers of synthetic compounds for the purpose of screening for biological activity. Such large mixtures and pools of compounds pose significant challenges for the bioassay and analytical scientist. The analytical challenge is two-fold: separation of the active component of a mixture, and the identification of its structure. A variety of separation methods are available, including LC, HPLC, and CE. However, from the standpoint of separating biologically active components from a mixture of one or more targets with a combinatorial library necessitates the use and development of methods that select for and separate the complex (usually noncovalent) between the ligands and the target. Affinity column methods have been used to selectively isolate and subsequently analyze binding components of mixtures of compounds. For example, Kassel et al. (Kassel et al., Techniques in Protein Chemistry VI, J. Crabb, Ed., Academic Press, San Diego, 1995, 39–46) have used an immobilized src SH2 domain protein column to separate and then analyze by HPLC-ESI-MS the structure of high affinity binding phosphopeptides.

A similar technique, ACE-ESI-MS, uses affinity capillary electrophoresis to accomplish the separation of noncovalent complexes formed upon mixing a biomolecular target with a combinatorial library or mixture of compounds. The receptor is typically incorporated into the capillary so that those ligands present in the combinatorial mixture interact with the target and are retained or slowed down within the capillary. Once separated, these noncovalent complexes are analyzed on-line by ESI-MS to ascertain the structures of the complexes and bound components. This method incorporates into one, the two steps that were previously performed separately: the compound/noncovalent complex selection, as has previously been demonstrated for vancomycin (Chu et al., Acc. Chem. Res., 1995, 28, 461–468; Chu et al., J. Org. Chem., 1993, 58, 648–52) and the step of compound identification (Cai and Henion, J. Chromatogr., 1995, 703, 667–692). For example, ACE-ESI-MS has been applied to mixtures of vancomycin with peptide libraries (Chu et al., J. Am. Chem. Soc., 1996, 118, 7827–35) to allow rapid screening of noncovalent complexes formed, and the identification of peptides that bind to vancomycin.

Another method for the separation and identification of active components from combinatorial libraries is the use of size-exclusion chromatography (SEC) followed by LC/MS or CE/MS analysis. Size exclusion is a simple yet powerful method to separate a biopolymer target and its complexes with small molecules members of a combinatorial library. Once isolated by SEC, these complexes are dissociated, under denaturing solution conditions, and finally the binding ligands are analyzed by mass spectrometry. This method has been applied to the identification of high affinity ligands for human serum albumin (HSA) from combinatorial library of small molecules (Dunayevskiy et al., Rapid Commun. Mass Spectrom., 1997, 11, 1178–84).

Bio-affinity characterization mass spectrometry (BACMS) is yet another method for the characterization of noncovalent interactions of mixtures of ligands and biomolecular targets (Bruce et al., Rapid Commun. Mass Spectrom., 1995, 9, 644–50). BACMS involves the electrospray ionization of a solution containing both the affinity target and a mixture of ligands (or a combinatorial library), followed by trapping of all the ionic species in the FTICR ion-trap. The complexes of interest are then identified in the mass spectrum and isolated by selected-ion accumulation. This is followed by low energy dissociation. or 'heating' to separate the high binding affinity ligands present in the complex. Finally, collisionally activated dissociation (CAD) is used to provide structural information about the high binding affinity ligand. The greatest advantage of BACMS is that the time-consuming techniques usually needed for the study of libraries, such as affinity chromatography, using solid supports for separation and purification of the complexes, followed by analysis to characterize the selected ligands, are all combined into one FTICR-MS experiment. To date, BACMS has only been applied to the study of protein targets.

None of the foregoing methods, however, have demonstrated applicability to a variety of biomolecular targets. Further, such methods do not provide rapid determination of the site of interaction between a combinatorially derived ligand and biopolymer.

Tandem mass spectrometry, as performed using electrospray ionization (ESI) on FTICR, triple quadrupole, or ion-trap mass spectrometers, has been found to be a powerfill tool for determining the structure of biomolecules. It is known in the art that both small and large (>3000 kbase) RNA and DNA may be transferred from solution into the gas phase as intact ions using electrospray techniques. Further it is known, to those skilled in the art that these ions retain some degree of their solution structures as ions in the gas phase; this is especially useful when studying noncovalent complexes of nucleic acids and proteins, and nucleic acids and small molecules by mass spectrometric techniques.

SUMMARY OF CERTAIN PREFERRED EMBODIMENTS

Studies have demonstrated that oligonucleotides and nucleic acids obey certain fragmentation patterns during collisionally induced dissociation (CID), and that these fragments and patterns can be used to determine the sequence of the nucleic McLuckey, Van Berkel and Glish, J. Am. Soc. Mass Spectrom., 1992, 3, 60–70; Mcluckey and Habibigoudarzi, J. Am. Chem. Soc., 1993, 115, 12085–12095). Electrospray ionization produces several multiply charged ions of the parent nucleic acid, without any significant fragmentation of the nucleic acid. Typically, a single charge state of the nucleic acid is isolated using a triple quadrupole ion trap, or ion cyclotron resonance (ICR) device. This ion is then excited and allowed to collide with a neutral gas such as helium, argon or nitrogen so as to afford cleavage of certain bonds in the nucleic acid ion, or excited and fragmented with a laser pulse. Typically, two series of fragment ions are found to be formed: the a-Base series, and the w-series.

The series of a-Base fragments originates from initial cleavage of the glycosidic bond by simultaneous abstraction of a C-2' proton, followed by the elimination of the 3'-phosphate group and the C-4' proton. This fragmentation scheme results in a residual furan attached to the 3'-phosphate and affords a series of a-Base fragments whose masses increase sequentially from the 5'-terminus of the nucleic acid. Measurement of the masses of these collisionally induced fragments therefore affords the determination of the sequence of the nucleic acid in the 5' to 3' direction. The w series of fragments is generated via cleavage of the nucleic acid in a manner that leaves a 5'phosphate residue on each fragment. Thus monitoring the masses of w-series fragments allows determination of the sequence of the nucleic acid in the 3' to 5' direction. Using the sequence information generated from both series of fragments the sequence of deoxyribonucleic acids (DNA) may be ascertained. Obtaining similar mass spectrometric information for ribonucleic acids (RNA), is a much more difficult task. Collisionally induced dissociation (CID) of RNA is much less energetically favored than is the case for DNA because of the greater strength of the glycosidic bond in RNA. Hence, while small RNA such as 6-mers have been sequenced using CID MS, the sequencing of larger RNA has not been generally successful using tandem MS.

Determination of the structure of biomolecules, such as proteins and nucleic acids, may be attempted using solution biochemical cleavage followed by mass spectrometry. However, these methods are cumbersome and not always successful in that several biochemical cleavage and separation steps need to be performed prior to MS analysis of the cleaved products. Also, the level of information provided with regards to secondary and tertiary structure of biomolecules is limited. Methods available in the scientific literature are therefore greatly limited in terms of the sequence and structural information they provide for biomolecules and biomolecular targets.

One aspect of the present invention provides methods for determining the structure of biomolecular targets such as nucleic acids using mass spectrometry. The structure of nucleic acids, especially RNA, which is often difficult to ascertain, is readily determined using the methods of this invention. The structure of a nucleic acid is determined from the fragmentation pattern observed in $MS^n$ experiments. Directed fragmentation of RNA is facilitated by the selective incorporation of deoxynucleotides or other nucleosidic residues at specific residue locations in the nucleic acid sequence. During CID of such RNA/DNA chimeric nucleic acids, cleavage is facilitated at the sites where deoxynucleotides or the other non-native residues were incorporated. Cleavage is also influenced by the local secondary and tertiary structure of the biomolecule. Therefore, the cleavage patterns observed from a RNA/DNA hybrid reveals the local structure of the nucleic acid, including mismatched base pairs, bulged regions and other features.

Since exposed deoxynucleotide residues are known to be susceptible to CID cleavage in MS experiments, the systematic incorporation of such residues into RNA allows the systematic exploration of the local structure of RNA. Using this embodiment of the invention, it is possible to determine the secondary and tertiary structure of nucleic acids, including features such as mismatched base pairs, loops, bulges, and kink and stem structures.

Determination of the structure of an RNA may be accomplished, using exemplary methods of the invention, as follows. An RNA whose structure is to be determined is synthesized using an automated nucleic acid synthesizer. During RNA synthesis, deoxynucleotides are selectively incorporated into the sequence at specific sites where the structure is to be probed. This RNA/DNA chimeric nucleic acid, which is sensitized to collisional activation, is now used for sequence and structure determination using tandem MS experiments. ESI-MS, followed by trapping of selected ions and subsequent CID of each ion, affords information as to which positions of the nucleic acid hybrid are disordered (or not participating in a higher order structure) and, therefore, available for cleavage. A systematic pattern of deoxynucleotide incorporation into the sequence of the test RNA allows a systematic, mass spectrometric assessment of structure in a certain area of the nucleic acid, or for the entire nucleic acid. Other modified nucleic acid residues may be used instead of a DNA. This, chemically modified nucleic acid subunits such as $Z^1$-modified, e.g. $2^1$-O-Alkyl, base-modified, backbone modified or other residues may serve. Such residues will permit assessment of DNA as well as RNA.

The present invention also provides methods for the determination of the site and nature of interactions between a biomolecular target and abinding ligand. This is information of critical value to the process of drug discovery. Current methods of biomolecular screening do not provide a straightforward means of also determining the nature of the interaction between abinding ligand and the biomolecular target. Information such as the stoichiometry and binding affinity of the interaction often needs to be ascertained from additional biochemical assays, thus slowing down and increasing the cost of drug discovery. It is often the case that binding of a drug or ligand to a biomolecular target, such as a nucleic acid, may lead to a change in conformation of the biomolecule to a different structure. This, too, may contribute to protection of the biomolecule from cleavage.

The present invention provides convenient methods for determining the site or sites on a biomolecular target where a binding ligand interacts. This is accomplished based on the knowledge that collisionally activated dissociation (CID or CAD) of a noncovalent biomolecule-ligand complex may be performed such that cleavage of the complex occurs only( at exposed sites of the biomolecules. Thus cleavage sites present on the biomolecule that are involved in binding with the ligand are protected because of the increased structural order from the binding event during CID. $ESI-MS^n$ spectra generated using this method, in the presence and absence of a binding ligand (or drug), will reveal differential fragmentation patterns due to ligand induced protection of cleavage sites. Comparison of the mass spectra generated in the presence and absence of a binding ligand will, therefore, reveal the positions in the biomolecular sequence where the interactions between ligand and biomolecule are occurring.

These methods for determining the sites of interaction between abinding ligand and a biomolecular target are broadly applicable. The biomolecular targets that may be studied using this method include, but are not limited to, peptides, proteins, antibodies, oligonucleotides, RNA, DNA, other nucleic acids, glycopeptides, and oligosaccharides. It is preferred that the biomolecular target be a nucleic acid. It is further preferred that the biomolecular target be a chimeric RNA/DNA nucleic acid, synthesized to selectively incorporate deoxynucleotides, (or other residues) in the sequence at specific locations. The binding ligand may be one of the groups of molecules including, but not limited to, organic or inorganic, small to large molecular weight individual compounds, mixtures and combinatorial libraries of ligands, inhibitors, agonists, antagonists, substrates, and biopolymers, such as peptides or oligonucleotides.

Determination of the sites on an RNA target where interaction occurs with abinding ligand may be accomplished as follows. An RNA target that is to be studied as a biomolecular target is prepared using an automated synthesizer, and selectively incorporating deoxynucleotides into the sequence at specific sites. An aliquot of this RNA/DNA chimeric is used directly for ESI-MS, followed by CID analysis of selectively accumulated ions, to establish the native structure and cleavage patterns of this biomolecular target. A second aliquot of the RNA/DNA chimeric is mixed with a solution of a drug or ligand that is known to bind to the biomolecular target. The target and ligand are anticipated to interact in solution to form a noncovalent complex. Subjecting this solution of the noncovalent biomolecule-ligand complex to the method of this invention leads to ionization of the complex with a retention of the noncovalent interactions and binding stoichiometries. CID of the complex then leads to cleavage of the biomolecule sequence at fragmentation sites that are exposed. Sites where fragmentation would otherwise occur, but which are involved in binding the ligand to the biomolecule, are protected, such that cleavage at or near these sites is prevented during the CID stage. The differences in the fragmentation patterns of the biomolecule when subjected to the methods of this invention in the presence and absence of binding ligand indicate the site(s) on the biomolecule that is protected and, therefore, are involved in binding the ligand.

Likewise, a systematic pattern of deoxynucleotide incorporation into the sequence of the test RNA will allow for a systematic mass spectrometric assessment of binding sites and interactions in a certain area of the nucleic acid, or for the entire nucleic acid, using the method of this invention. This invention, therefore, also provides a new method of 'footprinting' biomolecular targets especially nucleic acids. This footptinting by mass spectrometry is a straightforward method for mapping the structure of biomolecular targets and the sites of interactions of ligands with these targets.

The nature of interactions between the binding ligand and a biomolecular target are also readily studied using the method of this invention. Thus, the stoichiometry and absolute and relative dissociation constant of the biomolecule-ligand noncovalent complex is readily ascertained using the method of this invention. The ratio of the number of ligand molecules and the number of biomolecular receptors involved in the formation of a noncovalent biomolecule-ligand complex is of significant importance to the biochemist and medicinal chemist. Likewise, the strength of a noncovalent complex, or the binding affinity of the ligand for the biomolecular target, is of significance because it provides an indication of the degree of complementarity between the ligand and the biomolecule. Also, the determination of this binding affinity is important for the rank ordering of different ligands so as to provide structure-activity relationships for a series of ligands, and to facilitate the design of stronger binding ligands for a particular biomolecular target.

The methods of the present invention are also capable of determining both the binding stoichiometry and affinity of a ligand for the biomolecular target being screened in a screening study. Electrospray ionization is known to retain to a significant degree, the solution phase structures of biomolecules and their noncovalent complexes in the gaseous ions it generates. Thus, determination of the stoichiometry of noncovalent complexes simply needs data on the masses of the ligand, biomolecular target and the noncovalent biomolecule-ligand complex. The data needed to accomplish this determination is actually available from the mass spectrometry experiment that may be performed to determine the structure and site of binding of a ligand to the biomolecular target. Based on the knowledge of the structure and sequence of the target biomolecule, MS analysis of the biomolecule-ligand complex reveals the number of ligand and target molecules present in the noncovalent complex. If the noncovalent complex ion observed from the mass spectrum is of an m/z equal to that expected from the addition of the m/z values of one molecule each of the target biomolecule and ligand, then the noncovalent complex must be formed from a 1:1 interaction between the biomolecule and ligand. Simple mathematical operations on the molecular weight and charges of the target and ligand can likewise determine higher levels of interactions between ligand and biomolecule. The high resolution of a FTICR mass spectrometer allows direct identification of the bound ligand based on exact measurement of the molecular mass of the complex relative to unbound nucleic acid.

The use of mass spectrometry, in accordance with this invention can provide information on not only the mass to charge ratio of ions generated from a sample, but also the relative abundance of such ions. Under standardized experimental conditions, it is therefore possible to compare the abundance of anoncovalent biomolecule-ligand complex ion with the ion abundance of the noncovalent complex formed between a biomolecule and a standard molecule, such as a known substrate or inhibitor. Through this comparison, binding affinity of the ligand for the biomolecule, relative to the known binding of a standard molecule, may be ascertained. In addition, the absolute binding affinity can also be determined.

Determination of the nature of the interaction of a ligand with a biomolecular target may be carried out as exemplified for the binding of a small molecule ligand with a nucleic acid target. A chimeric RNA/DNA biomolecular target whose binding to a test ligand is to be studied is first prepared via automated synthesis protocols. An aliquot of a known concentration of chimeric nucleic acid is treated with a known concentration and quantity of a standard compound that is known to bind that nucleic acid, such as the aminoglycoside paromomycin which is known to bind to the 16S A-site of RNA. ESI-MS, followed by CID of the paromomycin-nucleic acid complex, affords a control spectrum for the interactions and complex. A second aliquot of the chimeric nucleic acid is next treated with a test ligand using quantities and concentrations similar to those used for the control experiment. Application of the method of the invention to this nucleic acid-ligand noncovalent complex affords a test spectrum that reveals the nature of the biomolecule-ligand interaction. Analysis of the noncovalent nucleic acid-ligand complex based on the known molecular weights of the two components of the complex allows the determination of the number of nucleic acid molecules and ligands present in the complex. Further, comparison of the abundance of the nucleic acid-ligand complex ion with the abundance of the ion generated from the e.g. paromomycin-nucleic acid complex (or complex with any other known interacting species) provides a convenient and direct estimate of the binding affinity of the test ligand compared to the standard, paromomycin. Since the standard is well characterized, its solution binding affinity should be known from other experiments or literature sources. For example, paromomycin binds to a test 27-mer RNA with a ~1 $\mu$M affinity. Knowing the binding affinity of the test ligand relative to paromomycin from the MS experiment, it is now possible to determine the micromolar binding affinity of the test ligand for the nucleic acid target being studied. Relative binding affinity may also be measured by testing a standard compound and test ligand simultaneously as in a mixture with the target biomolecule, in a single test assay.

Another object of the present invention is to provide general methods for the screening of compounds for drug discovery. The invention provides methods for the screening of a wide variety of biomolecular targets that include, but are not limited to, peptides, proteins, receptors, antibodies, oligonucleotides, RNA, DNA, RNA/DNA hybrids, nucleic acids, oligosaccharides, carbohydrates, and glycopeptides. The molecules that may be screened by using the methods of this invention include, but are not limited to, organic or inorganic, small to large molecular weight individual compounds, mixtures and combinatorial libraries of ligands, inhibitors, agonists, antagonists, substrates, and biopolymers, such as peptides or oligonucleotides.

The primary challenge when screening large collections and mixtures of compounds is not in finding biologically relevant activities, for this has been demonstrated in many different cases, but in identifying the active components from such screens, and often from mixtures and pools of compounds that are found to be active. One solution that has been practiced by the art-skilled in high throughput drug discovery is the iterative deconvolution of mixtures. Deconvolution essentially entails the resynthesis of that combinatorial pool or mixture that was found to be active in screening against a target of interest. Resynthesis may result in the generation of a set of smaller pools or mixtures, or a set of individual compounds. Rescreening and iterative deconvolution are performed until the individual compounds that are responsible for the activity observed in the screens of the parent mixtures are isolated.

However, analytical techniques are limited in their ability to adequately handle the types of mixtures generated in combinatorial efforts. The similarity of members of combinatorial mixtures or pools, and the complexity of such mixtures, prohibit effective analytical assessment until the mixtures have been deconvoluted into individual compounds, or at the very least into pools of only a handful of components. While this process of deconvolution, involving resynthesis, rescreening and analysis, is very cumbersome and time-consuming, it is also very costly. A general method that alleviates these problems by rapidly revealing active mixtures and identifying the active components of such mixtures is clearly needed to save time and money in the drug discovery process.

The present invention solves the need for a method to rapidly assess the activity of combinatorial mixtures against a biomolecular target and also identify the structure of the active components of such mixtures. This is exemplified by the screening of combinatorial mixtures for binding to a nucleic acid target as follows. A chimeric RNA/DNA target of known sequence is selected as the screening target based on biological relevance. This chimeric nucleic acid target is prepared via automated synthesis. An aliquot of the nucleic acid is used at a concentration of 10 $\mu$M and treated with e. q. paromomycin acetate at a concentration of 150 nM. A sample of the mixture is analyzed by the method of the invention to demonstrate binding of the paromomycin by observation of the paromomycin-nucleic acid complex ion. Next, an aliquot of this mixture is treated with a DMSO solution of a combinatorial mixture of compounds such that the final concentration of each component of the mixture is ~150 nM. This sample is then subjected to ESI-MS, and the mass spectrum monitored for the appearance of new signals that correspond to new nucleic acid-liganid noncovalent complexes formed with components of the combinatorial library.

The relative dissociation constants of these new complexes are determined by comparing the abundance of these new ions with the abundance of the paromomycin-nucleic acid complex ion whose binding affinity for the target is known a priori. Algorithmic deconvolution of the new complex ions observed, while taking into account the masses of the target and the components of the combinatorial library, provides the molecular weights of the binding ligands present in the observed noncovalent complexes. Alternatively, the identity of the binding ligand may also be determined by first isolating the newly observed complex ion using a triple quadrupole ion-trap or an ion cyclotron resonance device (ICR) followed by conventional identification by mass spectrometry fragment analysis. For example, upon isolation, a noncovalent complex ion is 'heated' or dissociated into the constituent ligand and biomolecule ions. This MS/MS experiment then can be tuned to study fragmentation of the ligand. This information provides direct evidence of the structure of the bound ligand. This method of the present invention, therefore, provides both the identity and relative binding affinity of members of combinatorial or other mixtures of compounds that bind to the nucleic acid target.

Not only does the present invention provide methods for the determination of the molecular weight and absolute and relative binding affinity of the binding components of a combinatorial or other mixture of compounds, but it also provides valuable information about the site of binding on the biomolecular target. Such information permits the identification of compounds having particular biological activity and gives rise to useful drugs, veterinary drugs, agricultural chemicals, industrial chemicals, diagnostics and other useful compounds. This can also be accomplished as part of the same mass spectrometric procedure by isolating the newly observed complex ions using a triple quadrupole ion-trap or an ion cyclotron resonance device (ICR). For example, upon isolation, a noncovalent complex ion is collisionally activated to cleave the chimeric nucleic acid target at exposed deoxynucleotide sites. This MS/MS procedure, then, can be tuned to study fragmentation of the biomolecular target.

Comparison of the cleavage and fragment patterns so obtained for the nucleic acid component of the noncovalent complex with patterns obtained for the native chimeric nucleic acid alone reveals the locations on the nucleic acid that are protected by the binding of the ligand. This indicates the binding sites for the ligand on the nucleic acid. Comparison of the cleavage patterns to those observed from the CID of the standard-nucleic acid complex ion provide correlations between the sites of binding of the new ligand and standard. In this fashion, ligands that bind to nucleic acid targets may be identified such that they compete for the same binding site on the nucleic acid where the standard binds, or bind at completely different and new sites on the nucleic acid. Both these types of observations are of value from a drug discovery standpoint.

The methods of the present invention can be used to identify metal ion binding sites on any of the biomolecules described herein. Preferably, the metal ion binding site binds alkali metals or alkaline earth metals. More preferably, the metal ions are $Na^+$, $Mg^{++}$ and $Mn^{++}$.

Drug discovery, using any one of a number of different types of biomolecular targets attends use of the methods of this invention which can rapidly screen large combinatorial libraries and mixtures of compounds for binding activity against a specific target.

It is possible that combinatorial libraries and mixtures of compounds being used for screening may contain components that are similar in mass because their elemental compositions are similar while their structures are different, or at the very least, isomeric or enantiomeric. In such instances, a simple algorithmic calculation of the molecular weight of a bound ligand will be insufficient to provide the identity of the ligand for there may be multiple components of the same molecular mass. The methods of the invention are also capable of addressing and resolving such problems of ligand identification. The use of MS/MS experiments to further fragment the bound ligand, following selective ion accumulation of the ligand ion from the noncovalent complex, is a simple technique that provides structural detail of the bound ligand. This mass and structural information provided by the methods of this invention is expected to resolve the vast majority of mass redundancy problems associated with the screening of large combinatorial libraries and mixtures of compounds.

In a preferred embodiment, the present invention also provides method for simultaneously screening multiple biomolecular targets against combinatorial libraries and mixtures or collections of compounds. This is a significant advantage of the present invention over current state-of-the-art techniques in the screening of compounds for such binding. There is believed to be no prior technique that allows the simultaneous and rapid screening of multiple targets, while providing structural detail on the target and binding ligand at the same time. In addition to providing methods for the rapid and simultaneous screening of multiple biomolecular targets, the present invention also provides methods for determining the structure and nature of binding of both the target and binding ligand.

As discussed above, mass spectrometry methods of the present invention provide a direct means for screening and identifying those components of combinatorial mixtures that bind to a target biomolecule in solution. In order to enhance efficiency, it is preferable to multiplex the screening process by simultaneously screening multiple targets for binding activity against a combinatorial library or mixture of compounds. This strategy is normally limited by the distribution of charge states and the undesirable mass/charge overlap that will be generated from all possible noncovalent biomolecule-ligand complexes that could be formed during such a screening assay. This problem of overlapping peaks in the mass spectra is further exacerbated if the biomolecular targets being screened are of similar sequence, composition, or molecular weight. In such instances it would not be possible to ascertain in a rapid and simple operation the composition of biomolecule-ligand complexes because of the extensive mass redundancy present in the pool of biomolecules being studied and possible in the combinatorial library being screened.

The method of the present invention alleviates the problem of biomolecular target mass redundancy through the use of special mass modifying molecular weight tags. These mass modify tags are typically uncharged or positively charged groups such as, but not limited to, alkyl and tetaalkylammonium groups, and polymers such as, but not limited to, polyethylene glycols (PEG), polypropylene, polystyrene, cellulose, sephadex, dextrans, cyclodextrins, peptides, and polyacrylamides. These mass modifying tags may be selected based on their molecular weight contribution and their ionic nature. These mass modifying tags may be attached to the biopolymeric targets at one or more sites including, but not limited to, the 2'-O—, 3'-terminus, 5'-terminus or along the sugar-phosphate backbone of nucleic acid targets. Addition of mass modifying tags to the 5'terminus of synthetic oligonucleotides can be realized either using conventional phosphoramidite chemistry, other conventional chemistry or by biochemical or enzymatic means. Such mass modification of a nucleic acid may be carried out using conventional, manual or automated techniques. Alternatively, addition of mass modifying tags may be performed at the 3'-terminus by the use of appropriately modified polymer or CPG supports for solid-phase synthesis of nucleic acids. Mass modification at the 3'terminus may also be done by biochemical or enzymatic means. It is also possible to attach mass modifying tags to the internucleotide linkages of a nucleic acid. This may be performed via the use of appropriately modified phosphoramidites, or other nucleoside building blocks during nucleic acid synthesis or via post-synthetic modification of the internucleotide linkage. Further, attachment of mass modifying tags to nucleic acid targets may also be accomplished via the use of bifunctional linkers at any functional site on the nucleic acid. Similarly, when working with other classes of biomolecular targets these mass modifying tags may likewise be incorporated at one or more positions on the biomolecule. As will be apparent, inclusion in either target or ligand of isotopic mass labels may also be useful.

Thus, similar nucleic acid and other biological targets may be differentially tagged for rapid mass spectrometric screening by the methods of this invention. When noncovalent complexes are observed from this multiplexed screening of multiple nucleic acid targets with mixtures of small molecular weight combinatorial libraries, the constituent ligand and biomolecule are readily identified using conventional mass analyzers such as quadrupole, ion trap, ICR, magnetic sector, or TOF and followed by MS/MS. This is because the mass modifiing tags make the m/z (mass to charge ratio) of the signal arising from each target biomolecule-ligand complex ion of similar charge, distinct in the mass spectrum, and which results in cleanly separated ion peaks. Mass redundancy and peak overlap are both avoided by the use of mass modifying tags.

The present invention is also highly useful in combination with other techniques for the identification of ligands which interact with molecular interaction sites on RNA and other nucleic acids. Molecular interaction sites attend RNA and are believe to be highly important in the functioning of such RNA. The nucleotide sequences of molecular interaction sites are highly conserved, even among taxonomically diverse species. Moreover, such molecular interaction sites have specific structures which provide opportunities for ligand binding. Ascertaining which ligands bind to such sites as well as determining the relative affinities and specificities for the binding of each ligand provides lead compounds for drug discovery, therapeutics, agricultural chemistry, industrial chemistry and otherwise.

The present mass spectrometric techniques, especially the MASS techniques and those which possess similar analytical robustness and power, are ideally suited for cooperating with drug and other discovery and identification programs such as those which determine ligand binding to molecular interaction sites. The identification of molecular interaction sites in RNA and other nucleic acids and the determination of hierarchies of molecular ligands which likely bind to such molecular interaction sites can be evaluated through the present techniques. Thus, in accordance with preferred embodiments of the present invention, a hierarchy of ligands ranked in accordance with their anticipated or calculated likelihood of binding to a molecular interaction site of an RNA are actually synthesized. Such synthesis is preferably accomplished in an automated or robotized fashion, preferably from instruction sets provided in attendance to the ranked hierarchy of ligands. The compounds may be prepared in a library or mixture since the present mass spectrometric methods can evaluate pluralities of compounds and their complexes with RNA simultaneously.

After the ligands are synthesized, preferably in library form, they are contacted with the RNA having the molecular interaction site of interest. Complexation or binding (conventionally, non-covalent binding) is permitted to occur. The complexed RNA-ligand library is then analyzed by mass spectrometry. A principal object of the analysis is preferably the determination of which ligands bind to the RNA molecular interaction site and, among those, which ones rank more highly in terms of specificity and affinity. Accordingly, it is possible to identify from a mixture or library of compounds, which ones are the most interactive with a particular molecular interaction site so as to be able to modulate it. Such compounds can either be used themselves, or, more likely, be used as lead compounds for modification into drugs, agricultural chemicals, environmental chemicals, industrial and food chemicals and otherwise.

As described above, it is highly desirable to challenge RNAs having molecular interaction sites with libraries of compounds which have already been predicted or calculated to be likely to interact with the interaction sites. It is preferred that such molecules belong to ranked hierarchies so as to give rise to the greatest likelihood of finding highly potent modulators of the target RNA.

While there are a number of ways to identify compounds likely to interact with molecular interaction sites of RNA and other biological molecules, preferred methodologies are described in U.S. patent applications filed on even date herewith and assigned to the assignee of this invention. These application bear U.S. Ser. Nos. (Unknown) and have been assigned attorney docket numbers IBIS-0002, IBIS 0003, IBIS-0004, IBIS-0006 and IBIS-0007. All of the foregoing applications are incorporated by reference herein in their entirety.

One mass spectrometric method which is particularly useful when combined with the techniques of the foregoing commonly owned inventions provides the determination of specificity and affinity of ligands to RNA targets. MASS (multi target affinity/specificity screening) techniques can provide high throughput screening methods to analyze the pecificity and affinity of ligands to molecular interaction sites of nucleic acids, especially RNA. MASS employs high performance electrospray ionization Fourier transform ion cyclotron resonance mass spectrometry (ESI-FTICR-MS) to a) determine exact chemical composition of affinity selected ligands originating from a combinatorial library, b) determine relative dissociation constants (Kd) of ligands complexed to the target(s), and c) determine the location of ligand binding. This information can be gathered from each target(s) or library set in a single assay in less than 15 minutes. This scheme benefits from two unique aspects of the ESI-FTICR combination. The "soft" nature of the electrospray ionization process allows specific noncovalent complexes to be ionized and transferred into the gas phase intact where they are amenable to subsequent characterization by mass spectrometry. The high resolving power afforded by the FTICR platform facilitates the characterization of complex mixtures which, when combined with the high mass accuracy inherent to FTICR, provides unambiguous identification of ligands complexed with the molecular interaction site or sites of a target or targets.

Binding site information can be obtained by comparing the gas phase fragmentation patterns of the free and complexed target and absolute binding affinities while relative binding constants are derived from the relative abundance of complexes using a complex with a known Kd as an internal standard. With knowledge of the specificity and affinity of ligands to the molecular interaction site of a target RNA, the desired lead or ultimate compound for modulation of the RNA can be determined. Therapeutic, agricultural chemical, industrial chemical and other products which benefit from modulation of such RNA attend this result.

The simultaneous screening of a combinatorial library of molecules of mass 700–750, against two nucleic acid targets of the same molecular weight but different sequence, is demonstrated by the use of mass modifying tags. If both nucleic acids targets being studied are 27-mer RNAs of mass 8927, then screening a library of molecules of mass 700–750 could afford a be wildering jumble of noncovalent complex ions in the mass spectrum of the mixture of the two nucleic acids and the library. However if one of the two targets is mass modified, for example by the use of a PEG chain of mass 3575 attached at the 5' terminus of the target, then the mass spectrum will be significantly simplified. It is known that a 27-mer will generate multiply-charged ion signals, following electrospray ionization, of mass/charge values 1486.8, 1784.4, and 2230.8 for the $(M-6H)^{6-}$, $(M-5H)^{5-}$, and the $(M-4H)^{4-}$ charge states. Upon binding to small molecules of mass 700–750, the unmodified RNA-ligand complexes are anticipated to occur in the 1603.2–1611.6, 1924.4–1934.4, and 2405.8–2418.3 m/z range. If the second nucleic acid target were not modified in any way, the signals from its complexes would have occurred in the same regions. However, using the mass modified RNA, bearing the PEG chain of mass 3575, results in the observation of the corresponding mass modified RNA-ligand complexes to occur in the 2199–2207.4, 2639–2649 and 3299–3311 m/z range. Thus all signals from the second mass modified nucleic acid would be cleanly resolved from those of the first RNA. These noncovalent complex ions may be selected e.g. by triple, quadrupole, ion trap or ICR techniques, and studied further by MS/MS to afford detailed understanding of the sites of ligand-RNA interaction, and the nature of these interactions, as has been discussed above.

In a further embodiment, the methods of this invention are applicable for the determination of the specificity of binding interactions between a ligand and a biomolecular target. By simultaneously screening multiple biomolecular targets with one or more compounds, using the methods of this invention, it is possible to ascertain whether a ligand binds specifically to only one target biomolecule, or whether the binding observed with the target is reproduced with control biomolecules as well, and is therefore non-specific. This is an important distinction to be made when screening large libraries and collections of compounds for binding to biomolecular targets. It is desirable to quickly distinguish those ligands that are selective or specific for the biomolecular target of interest from those that are non-specific and bind to any and all targets. From the standpoint of drug discovery, it is most often the case that undesirable biological activities arise from the indiscriminate, non-specific binding of molecules to unrelated biomolecules. The present invention provides a valuable and straightforward method for assessing the specificity of interactions between a ligand and a panel of targets.

The use of mass modifying tags for the simultaneous screening of multiple biomolecular targets is applicable to the determination of binding specificity of a ligand as well. Mass modifing tags may be used to differentiate several biomolecular targets that serve as a control panel for screening a combinatorial library of individual compounds against a specific biomolecular target. When simultaneously screening multiple biomolecular targets using the mass spectrometric methods of this invention, it is necessary to ensure good separation of the ions that result from each target and its complex with the binding ligand. This peak overlap is easily eliminated by the facile introduction of different mass modifying tags onto the different biomolecular targets being studied. A mixture of the biomolecular target and the control panel is mixed with the ligand being evaluated. This solution is then ionized by ESI-MS, and the noncovalent complex ions observed may be directly identified as having resulted from the binding of the ligand to a specific target from the several biomolecular targets present in the mixture. In this way, a qualitative indication of specificity or selectivity of binding for the desired target versus the control biomolecules may be obtained. This selectivity may also be quantitated through the use of appropriate standards of known binding affinity and comparison of the ligand-biomolecule complex ion abundance to the abundance of the standard-biomolecule abundance. Further, details on the nature of the specific or non-specific interaction of the ligand with the different biomolecules may also be obtained following ion-selection and subsequent MS/MS experiments, as discussed above.

Likewise, it is also possible to determine the proportional binding of a ligand to two or more biomolecular targets using the methods of this invention. Thus by the use of appropriate mass modifying tags on the different biomolecular targets, the different noncovalent complexes formed via differential binding of the ligand can be readily distinguished in the mass spectrometer. Quantitation of the binding is possible by measuring the abundance of these ions. Comparing the relative abundances of these ions provides a means to determine the proportional binding of the ligand to the different biomolecular targets.

Yet another application of the methods of the present invention is to determine the differential binding of ligands to biomolecular targets of different origin. When studying the binding of small molecule ligands to RNA targets, it is straightforward to distinguish between the noncovalent ligand-RNA complexes generated from binding to the two different RNA targets, even though both may be screened simultaneously as a mixture in the same assay. Further, it is also possible to determine specificity and selectivity of the ligand for one versus the other RNA, and to determine the relative affinities of binding to each RNA target.

The methods of the present invention are applicable to the study of a wide variety of biomolecular targets that include, but are not limited to, peptides, proteins, receptors, antibodies, oligonucleotides, RNA, DNA, RNA/DNA hybrids, nucleic acids, modified oligonucleotides, peptide-nucleic acids (PNAs), oligosaccharides, carbohydrates, and glycopeptides. Further these biomolecular targets may be synthetic or isolated from natural sources. Biomolecular targets of natural origin include, but are not limited to, those obtained from microbial, plant, animal, viral or human materials, such as, but not limited to, cells, cell extracts, fluids, tissues and organs.

The molecules that may be screened by using the methods of this invention include, but are not limited to, organic or inorganic, small to large molecular weight individual compounds, and combinatorial mixture or libraries of ligands, inhibitors, agonists, antagonists, substrates, and biopolymers, such as peptides or oligonucleotides.

Combinatorial mixtures include, but are not limited to, collections of compounds, and libraries of compounds. These mixtures may be generated via combinatorial synthesis of mixtures or via admixture of individual compounds. Collections of compounds include, but are not limited to, sets of individual compounds or sets of mixtures or pools of compounds. These combinatorial libraries may be obtained from synthetic or from natural sources such as, for example to, microbial, plant, marine, viral and animal materials. Combinatorial libraries include at least about twenty compounds and as many as a thousands of individual compounds and potentially even more. When combinatorial libraries are mixtures of compounds these mixtures typically contain from 20 to 5000 compounds preferably from 50–1000, more preferably from 50–100. Combinations of from 100–500 are usefull as are mixtures having from 500–1000 individual species. Typically, members of combinatorial libraries have molecular weight less than about 5000 Da.

The mass spectrometry techniques that may be used in the methods of this invention include all of the techniques and systems described herein or are subsequently developed. Tandem techniques are also useful, including combinations of all of the foregoing and LC/MS. The mass spectrometers used in the methods of this invention may be a single quadrupole, triple quadrupole, magnetic sector, quadrupole ion trap, time-of-flight instrument, and FTICR. Future modifications to mass spectrometry are expected to give rise to improved techniques which may also be useful herein.

In another embodiment of the present invention, binding of mixtures of aminoglycosides can be measured simultaneously against multiple RNA targets of identical length and similar (or identical) molecular weight. Addition of a neutral mass tag to one of the RNA targets shifts those to a higher mass/charge ratio, where complexes with small molecules can be identified unambiguously. An appropriately placed neutral mass tag does not alter RNA-ligand binding. Preferably, this method is demonstrated with model RNAs corresponding to the decoding region of the prokaryotic and eukaryotic small subunit rRNAs and a mixture of compounds, such as, for example, five aminoglycosides. In the examples set forth below, complexes are observed between the aminoglycoside library and the prokaryotic rRNA model, while no aminoglycoside was observed to bind to the mass tagged eukaryotic rRNA model. The differential binding data is consistent with the eukaryotic A-site rRNA having a different confirmation compared to the prokaryotic A-site that prevents entry and binding of neomycin-class aminoglycosides. Mass spectrometric analysis of neutral mass-tagged macromolecular targets represents a new high throughput screening paradigm in which the interaction of multiple targets against a collection of small molecules can be evaluated in parallel.

Figure 24:
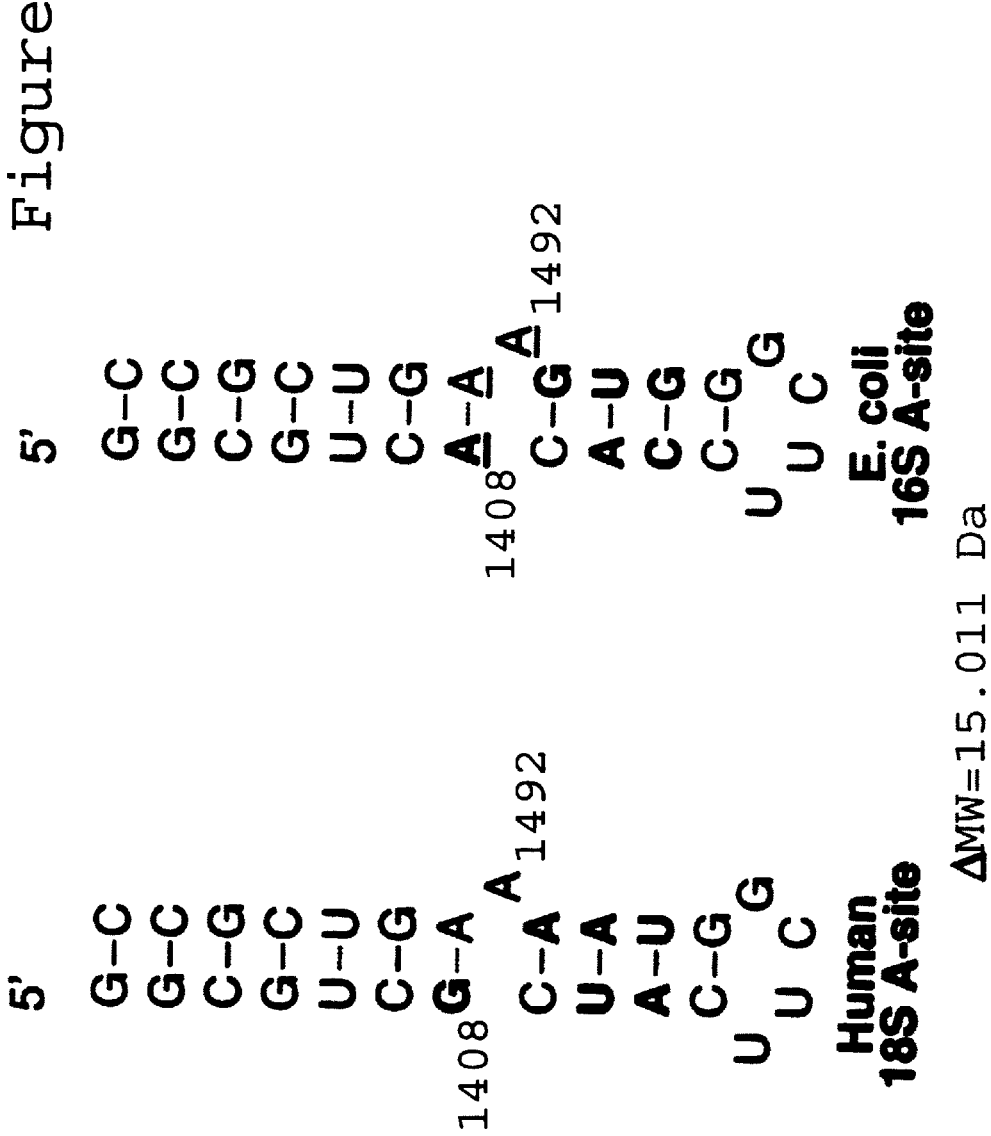
FIG. 24 depicts secondary structures of the 27 base RNA models used in this work corresponding to the 18S (eukaryotic) and 16S (prokaryotic) A-sites.

The preferred model system employed herein comprises a library comprised of five 2-deoxystreptamine aminoglycoside antibiotics which have a range of binding affinities for the decoding sites of the prokaryotic and eukaryotic ribosomal RNA ranging from ~28 nM to ~1.5 mM. FIG. 24 illustrates the secondary structures for the 27-nucleotide models of the 16S and 18S rRNA decoding sites. These constructs consist of a 7 base pair stem structure containing a non-canonical U-U and a purine-adenosine mismatch base pair adjacent to a bulged adenosine residue closed by a UUCG tetraloop. NMR studies of a complex between 16S and paromomycin show that the RNA makes primary hydrogen bond, electrostatic, and stacking contacts with the aminoglycoside (Fourmy, et al., *Science*, 1996, 274, 1367–1371) and that paromomycin binds in the major groove of the model A-site RNA within the pocket created by the A-A base pair and the single bulged adenine. The masses for the two RNA models differ by only 15.011 Da and the $(M-5H^+)^{5-}$ species of these constructs differ by only 3 m/z units. While the high resolution capabilities of the FTICR mass spectrometer can easily resolve these species, mass spectra from a solution containing both RNAs are complicated by overlap among the signals from free RNA ions and their sodium and potassium-adducted species.

Methods to increase the separation between the associated signals in the mass spectra due to overlap among signals from RNAs 16S and 18S are described herein. RNA targets modified with additional uncharged functional groups conjugated to their 5'-termini have been synthesized. Such a synthetic modification is referred to herein as a neutral mass tag. The shift in mass, and concomitant m/z, of a mass-tagged macromolecule moves the family of signals produced by the tagged RNA into a resolved region of the mass spectrum.

When simultaneously screening of untagged 16S and untagged 18S against a combinatorial library of small molecules, if a complex were observed at 515.011 Da higher than 16S, it would not be possible to directly determine (without tandem MS methods) whether the complex corresponded to a ligand weighing 515.011 Da complexed to the 16S target or a ligand weighing 500.000 Daltons complexed to 18S. Furthermore, because positively charged ligands can have non-specific interactions with RNA oligomers, it is often desirable to assay libraries for specific and non-specific binding by screening against two or more RNA targets simultaneously (e.g. a structured target sequence and an unstructured control sequence) in a single ESI-MS experiment. This multiplex advantage can be further exploited in the RNA-drug discovery arena in which libraries are to be assayed against multiple RNA targets of similar, or identical, mass. A single analysis in which 5 RNA targets are screened against a combinatorial library of 200 components facilitates the direct evaluation of 1000 RNA-ligand interactions from the acquisition of a single mass spectrum.

While the ability to shift the m/z range of closely related macromolecules is highly desirable as described above, it is preferably desired that the mass tag does not alter key physical properties of the target or the ligand binding properties. Preferably, an 18-atom mass tag ($C_{12}H_{25}O_9$) attached to the 5'-terminus of the RNA oligomer through a phosphodiester linkage can be employed. This mass tag has no appreciable affect on oligonucleotide solubility, ionization efficiency, or UV absorbance, and does not alter RNA-ligand binding. This latter attribute is evidenced by the data in FIG. 25 that illustrates the conserved ratio of free:bound RNA for the untagged and tagged RNA models of the bacterial decoding site under competitive binding conditions with paromomycin.

Aminoglycoside antibiotics inhibit bacterial growth by disrupting essential prokaryotic RNA-protein and RNA-RNA interactions. In vivo, a therapeutic effect is realized because paromomycin alters essential RNA interactions in prokaryotes (by binding to the 16S A-site with high affinity) but does appreciably disrupt the function of the eukaryotic RNA complexes (owing to the low affinity of paromomycin for the 18S A-site). A compound that binds both the 16S and 18S A-sites with similar affinity would likely inhibit bacterial growth but might also have deleterious cytotoxic effects in eukaryotic cells and would not make a suitable therapeutic agent. Thus, the 16S/18S model RNA system can serve not only as an interesting target for new generation antibiotics, but as a well characterized control for our mass spectrometry based RNA-ligand affinity assay.

Figure 26:
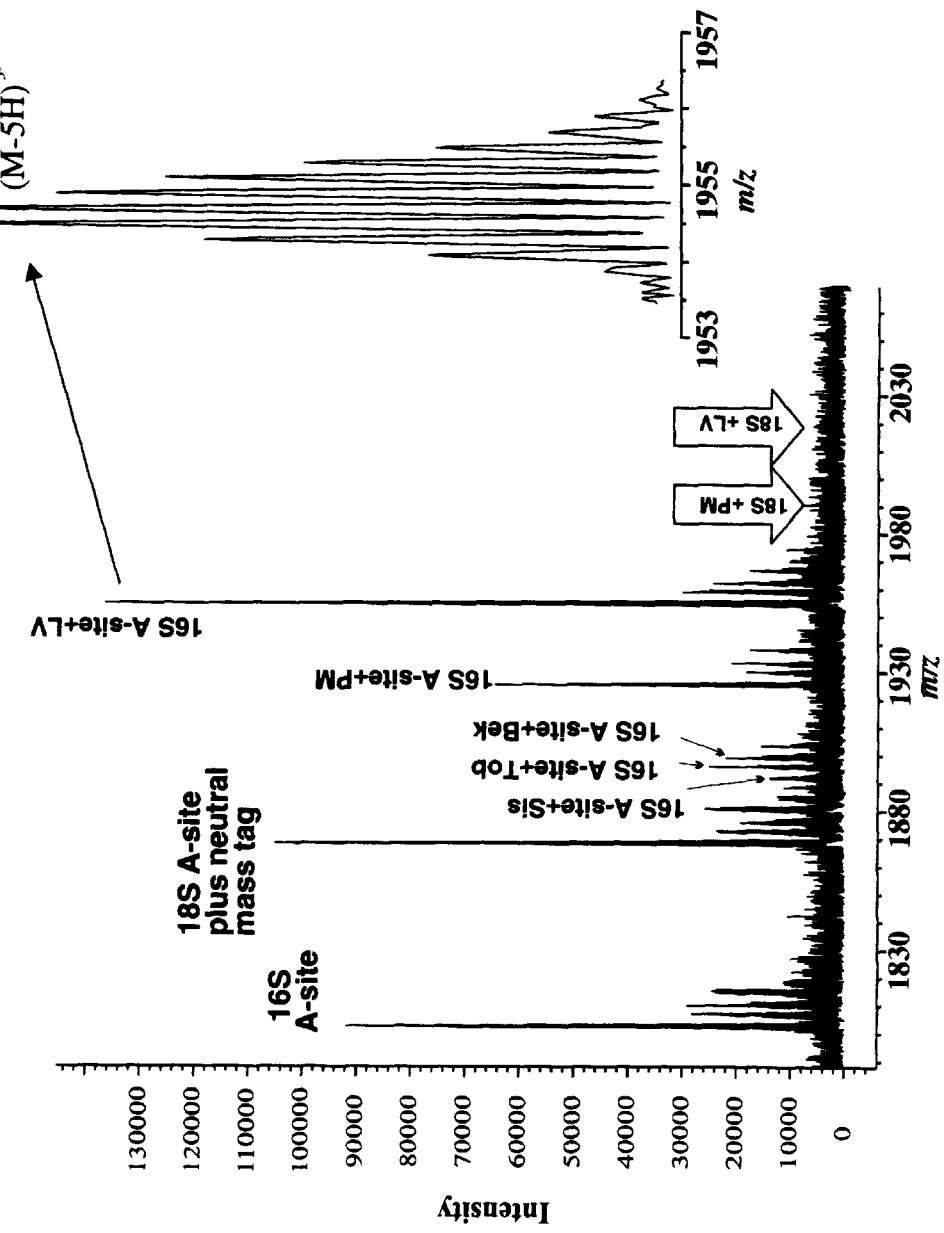
FIG. 26 depicts mass spectra from simultaneous screening of 16S A-site and 18S A-site Model RNAs against a mixture of aminoglycosides.

The ESI-FTICR mass spectrum depicted in FIG. 26 was acquired from a 10 mM mixture of untagged 16S and tagged 18S in the presence of an equimolar mixture of five aminoglycosides. It is to be understood that other biomolecules may be used in place of the aminoglycosides. The aminoglycosides have been selected from two classes of 2-deoxystreptamines: 4,5-disubstituted (paromomycin, and lividomycin), and 4,6-disubstituted (tobramycin, sisomicin, and bekanamycin), present at 500 nM each. Complexes corresponding to 1:1 binding of individual aminoglycosides were observed between 16S and all members of the aminoglycoside mixture, with the apparent affinities estimated from the abundances of the respective complexes differing substantially. Signal intensities from the complexes with paromomycin (m/z 1925.572) and lividomycin (m/z 1954.790) are consistent with MS-measured dissociation constants of 110 nM and 28 nM, respectively. The intensities of 16S complexes with tobramycin (m/z 1895.960), bekanamycin (m/z 1899.171), and sisomicin (m/z 1891.972) were reduced, consistent with solution dissociation constants of 1.5 mM. Wang, et al., *Biochemistry*, 1997, 36, 768–779. Hence, under these assay conditions, the MS-observed ion abundances reflect the solution dissociation constants. The inset in FIG. 26 demonstrates the ability to resolve the isotopic envelope for each complex and allows mass differences to be calculated from homo-isotopic species, thus, measuring the difference in m/z between the RNA target and the RNA-ligand complex allows precise mass determination of the ligand. The spectrum is calibrated using multiple isotope peaks of the $(M-5H^+)^{5-}$ and $(M-4H^+)^{4-}$ charge states of the free RNA as internal mass standards which brackets the m/z range in which complexes are observed. The average mass measurement error obtained for the complexes in FIG. 26 is 2.1 ppm when m/z differences are measured between the most bundant (4 $^{13}$C) isotope peak of 16S and each complex. This post calibration scheme is easily automated which enables rapid, high precision mass measurements of affinity selected ligands against multiple targets in a high throughput mode.

The enhanced affinity of lividomycin for 16S relative to the affinity of paromomycin or 16S is interesting. While lividomycin is believed to bind to the 16S ribosomal subunit, the exact site of interaction has not been established. Lividomycin has two significant structural differences from paromomycin. First, the additional mannopyranosyl ring could generate new macromolecular contacts with the RNA. However, the orientation of paromomycin ring IV is disordered in the NMR-derived structure for the complex with 16S. In addition, a hydroxyl group on ring I that makes a contact with A1492 is missing. The relatively high abundance of the 16S-lividomycin complex suggests that lividomycin binds at or near the 16S A-site, and generates additional contacts that enhance the binding affinity nearly 4-fold. Perhaps the most striking feature of the spectrum in FIG. 26 is the complete absence of complexes between 18S and paromomycin or lividomycin. This result suggests there must be poor shape and electrostatic complementarity between the 4,5-disubstituted 2-DOS class of aminoglycoside and the conserved architecture of the eukaryotic ribosomal decoding site.

Thus, according to the invention, RNA targets with similar (or identical) molecular masses can be labeled with small neutral molecules to measure binding between the targets and ligands using mass spectrometry. By screening multiple targets against ligand mixtures simultaneously, the information content of the assay is enhanced, resulting in a dramatic reduction in the number of analyses required. Although the increased complexity of the multi-substrate/ligand mixtures places high demands on the mass analyzer, the methods described herein facilitate the simultaneous analysis of numerous targets under identical solution conditions and ligand concentrations, further enhancing the high-throughput nature of the screening strategy and allowing direct comparisons of binding affinities for closely related targets. This concept of "rational" target design should also be applicable in studies of proteins that differ in amino acid sequence.

EXAMPLES

Example 1

Determining the Structure of a 27-mer RNA Corresponding to the 16S rRNA A Site

In order to study the structure of the 27-mer RNA corresponding to the 16S rRNA A site, of sequence 5'-GGC- GUC-ACA-CCU-UCG-GGU-GAA-GUC-GCC-3' (SEQ ID NO:1) a chimeric RNA/DNA molecule that incorporates three deoxyadenosine (dA) residues at positions 7, 20 and 21 was prepared using standard nucleic acid synthesis protocols on an automated synthesizer. This chimeric nucleic acid of sequence 5'-GGC-GUC-dACA-CCU-UCG-GGU-GdAdA-GUC-GCC-3' (SEQ ID NO:2) was injected as a solution in water into an electrospray mass spectrometer. Electrospray ionization of the chimeric afforded a set of multiply charged ions from which the ion corresponding to the $(M-5H)^{5-}$ form of the nucleic acid was further studied by subjecting it to collisionally induced dissociation (CID). The ion was found to be cleaved by the CID to afford three fragments of m/z 1006.1, 1162.8 and 1066.2. These fragments correspond to the $w_7^{(2-)}$, $w_8^{(2-)}$ and the $a_7\text{-}B^{(2-)}$ fragments re that are formed by cleavage of the chimeric nucleic acid adjacent to each of the incorporated dA residues.

The observation that cleavage and fragmentation of the chimeric RNA/DNA has occurred adjacent to all three dA sites indicates that the test RNA is not ordered around the locations where the dA residues were incorporated. Therefore, the test RNA is not structured at the 7, 20 and 21 positions.

A systematic series of chimeric RNA/DNA molecules is synthesized such that a, variety of molecules, each incorporating deoxy residues at different site(s) in the RNA. All such RNA/DNA members are comixed into one solution. MS analysis, as described above, are conducted on the comixture to provide a complete map or 'footprint' that indicates the residues that are involved in secondary or tertiary structure and those residues that are not involved in any structure. See FIG. 1.

Example 2

Determining the Binding Site for Paromomycin on a 27-mer RNA Corresponding to the 16S rRNA A Site In order to study the binding of paromomycin to the RNA of example 1, the chimeric RNA/DNA molecule of example I was synthesized using standard automated nucleic acid synthesis protocols on an automated synthesizer. A sample of this nucleic acid was then subjected to ESI followed by CID in a mass spectrometer to afford the fragmentation pattern indicating a lack of structure at the sites of dA incorporation, as described in Example 1. This indicated the accessibility of these dA sites in the structure of the chimeric nucleic acid.

Next, another sample of the chimeric nucleic acid was treated with a solution of paromomycin and the resulting mixture analyzed by ESI followed by CID using a mass spectrometer. The electrospray ionization was found to produce a set of multiply charged ions that was different from that observed for the nucleic acid alone. This was also indicative of binding of the paromomycin to the chimeric nucleic acid, because of the increased mass of the observed ion complex. Further, there was also observed, a shift in the distribution of the multiply charged ion complexes which reflected a change in the conformation of the nucleic acid in the paromomycin-nucleic acid complex into a more compact structure.

Figure 2:
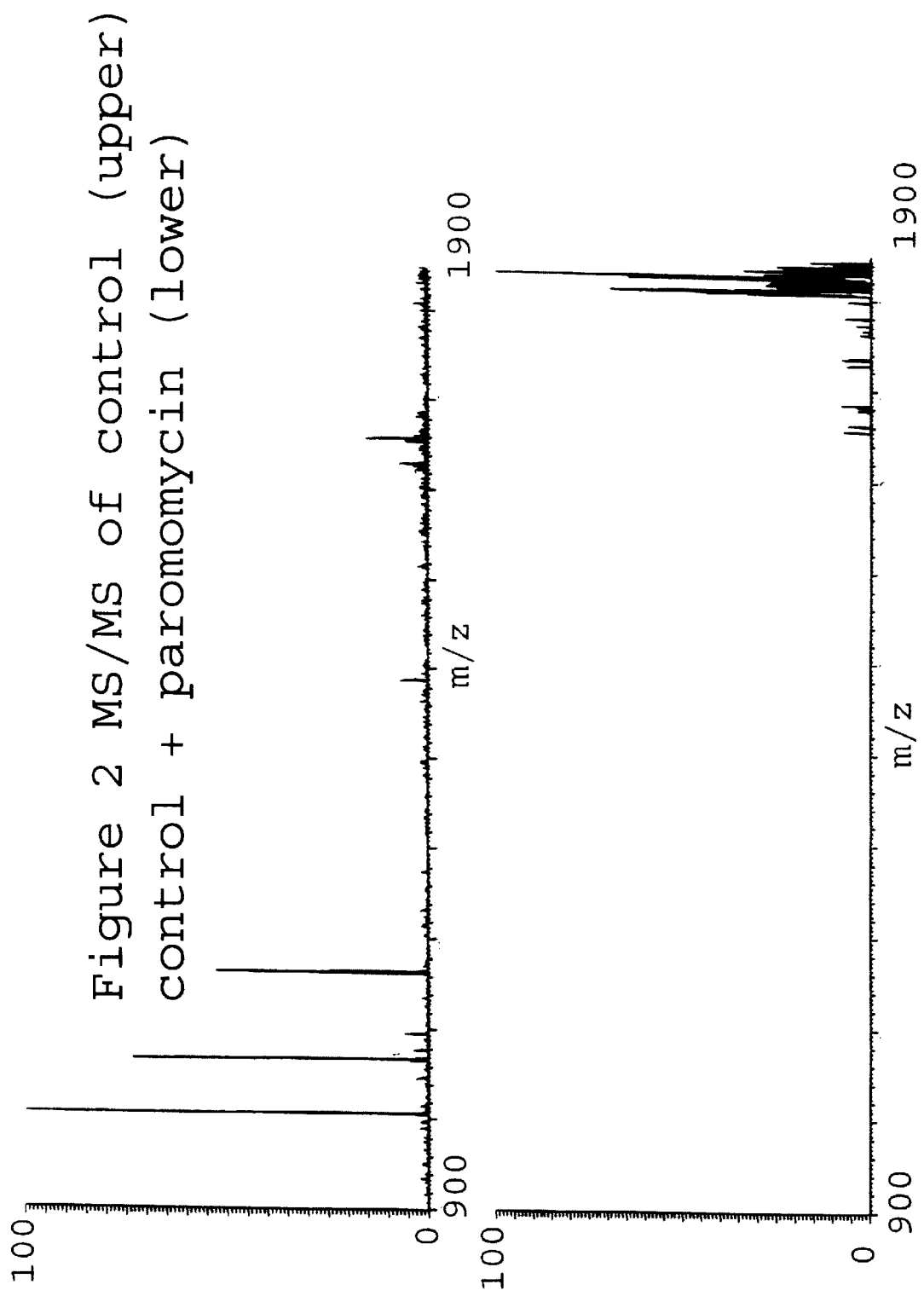
FIG. 2 shows the ESI-CID-MS of a 27-mer RNA/DNA hybrid in the presence and absence of paromomycin.

Cleavage and fragmentation of the complex by CID afforded information regarding the location of binding of the paromomycin to the chimeric nucleic acid. CID was found to produce no fragmentation at the dA sites in the nucleic acid. Thus paromomycin must bind at or near all three dA residues. Paromomycin therefore is believed to bind to the dA bulge in this RNA/DNA chimeric target, and induces a conformational change that protects all three dA residues from being cleaved during mass spectrometry. See FIG. 2.

Example 3

Determining the Identity of Members of a Combinatorial Library that Bind to a Biomolecular Target 1 mL (0.6 O.D.) of a solution of a 27-mer RNA containing 3 dA residues (from Example 1) was diluted into 500 µL of 1:1 isopropanol:water and adjusted to provide a solution that was 150 mM in ammonium acetate, pH 7.4 and wherein the RNA concentration was 10 mM. To this solution was added an aliquot of a solution of paromomycin acetate to a concentration of 150 nM. This mixture was then subjected to ESI-MS and the ionization of the nucleic acid and its complex monitored in the mass spectrum. A peak corresponding to the $(M-5H)^{5-}$ ion of the paromomycin-27 mer complex is observed at an m/z value of 1907.6. As expected, excess 27-mer is also observed in the mass spectrum as its $(M-5H)^{5-}$ peak at about 1784. The mass spectrum confirms the formation of only a 1:1 complex at 1907.6 (as would be expected from the addition of the masses of the 27-mer and paromomycin) and the absence of any bis complex that would be expected to appear at an m/z of 2036.5.

To the mixture of the 27-mer RNA/DNA chimeric and paromomycin was next added 0.7 mL of a 10 µM stock solution of a combinatorial library such that the final concentration of each member of the combinatorial library in this mixture with 27-mer target was 150 nM. This mixture of the 27-mer, paromomycin and combinatorial compounds was next infused into an ESI-MS at a rate of 5 mL/min. and a total of 50 scans were summed (4 microscans each), with 2 minutes of signal averaging, to afford the mass spectrum of the mixture.

Figure 3:
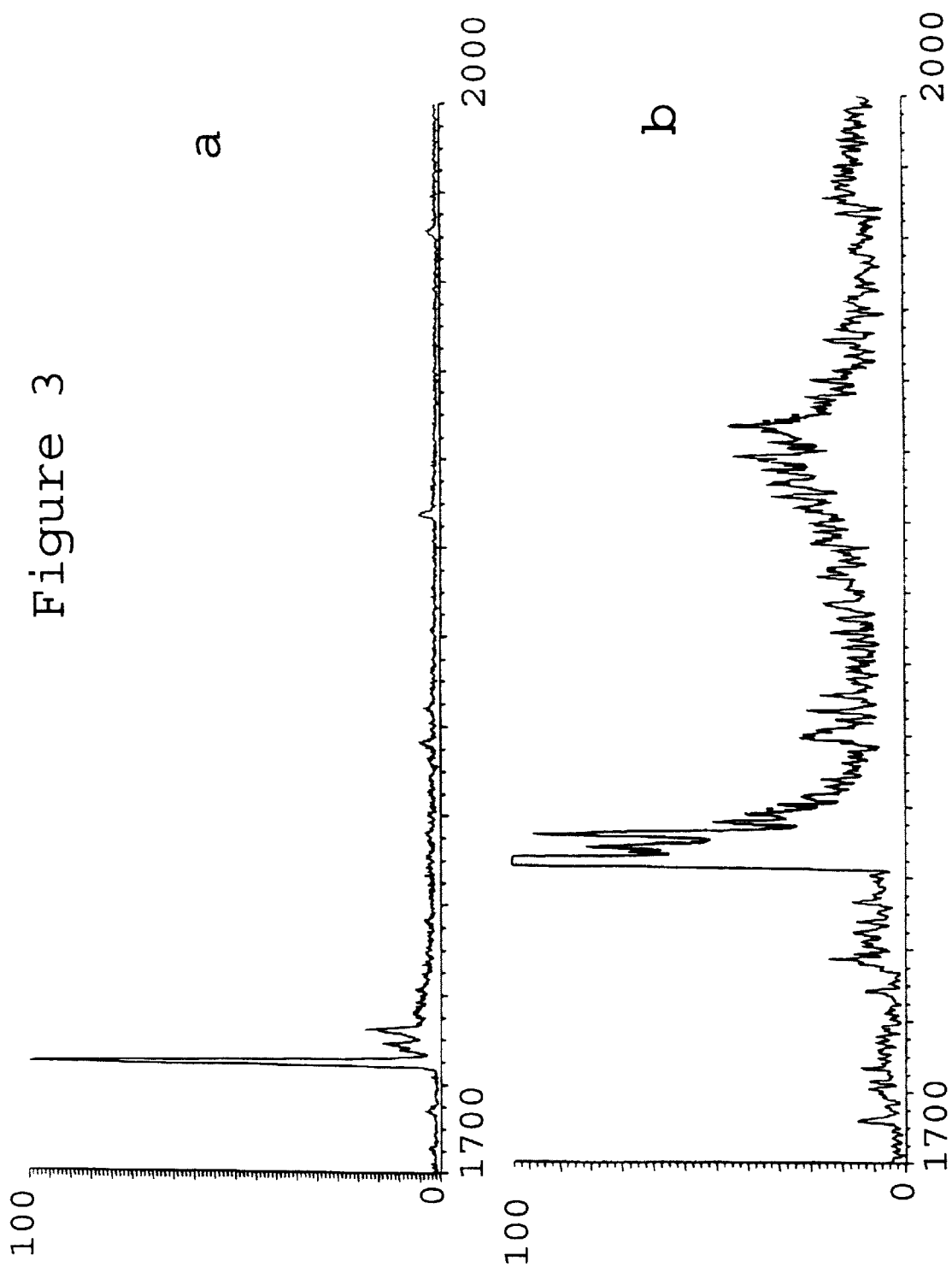
FIG. 3 shows the ESI-MS of a 27-mer RNA/DNA hybrid target in the presence of paromomycin alone (panel a), and in the presence of both paromomycin and a combinatorial library (panel b).

The ESI mass spectrum so obtained, shown in FIG. 3, demonstrated the presence of new signals for the $(M-5H)^{5-}$ ions at m/z values of 1897.8, 1891.3 and 1884.4. Comparing these new signals to the ion peak for the 27-mer alone the observed values of m/z of those members of the combinatorial library that are binding to the target can be calculated. The masses of the binding members of the library were determined to be 566.5, 534.5 and 482.5, respectively. Knowing the structure of the scaffold, and substituents used in the generation of this library, it was possible to determine what substitution pattern (combination of substituents) was present in the binding molecules.

It was determined that the species of m/z 482.5, 534.5 and 566.5 would be the library members that bore the acetic acid+MPAC groups, the aromatic+piperidyl guanidine groups and the MPAC+guanidylethylamide groups, respectively. In this manner, if the composition of the combinatorial library is known a priori, then the identity of the binding components is straightforward to elucidate.

The use of FTMS instrumentation in such a procedure enhances both the sensitivity and the accuracy of the method. With FTMS, this method is able to significantly decrease the chemical noise observed during the electrospray mass spectrometry of these samples, thereby facilitating the detection of more binders that may be much weaker in their binding affinity. Further, using FTMS, the high resolution of the instrument provides accurate assessment of the mass of binding components of the combinatorial library and therefore direct determination of the identity of these components if the structural make up of the library is known.

Example 4

Determining the Site of Binding for Members of a Combinatorial Library that Bind to a Biomolecular Target The mixture of 27-mer RNA/DNA chimeric nucleic acid, as target, with paromomycin and the combinatorial library of compounds from Example 3 was subjected to the same ESI-MS method as described in Example 3. The ESI spectrum from Example 2 showed new signals arising from the complexes formed from binding of library members to the target, at m/z values of 1897.8, 1891.3 and 1884.4. Theparomomycin-27mer complex ion was observed at an m/z of 1907.3.

Two complex ions were selected from this spectrum for further resolution to determine the site of binding of their component ligands on the 27-mer RNA/DNA chimeric. First, the ions at 1907.3, that correspond to the paromomycin-27 mer complex, were isolated via an ion-isolation procedure and then subjected to CID. No cleavage was found to occur and no fragmentation was observed in the mass spectrum. This indicates that the paromomycin binds at or near in the bulged region of this nucleic acid where the three dA residues are present. Paromomycin therefore protects the dA residues in the complex from fragmentation by CID.

Figure 4:
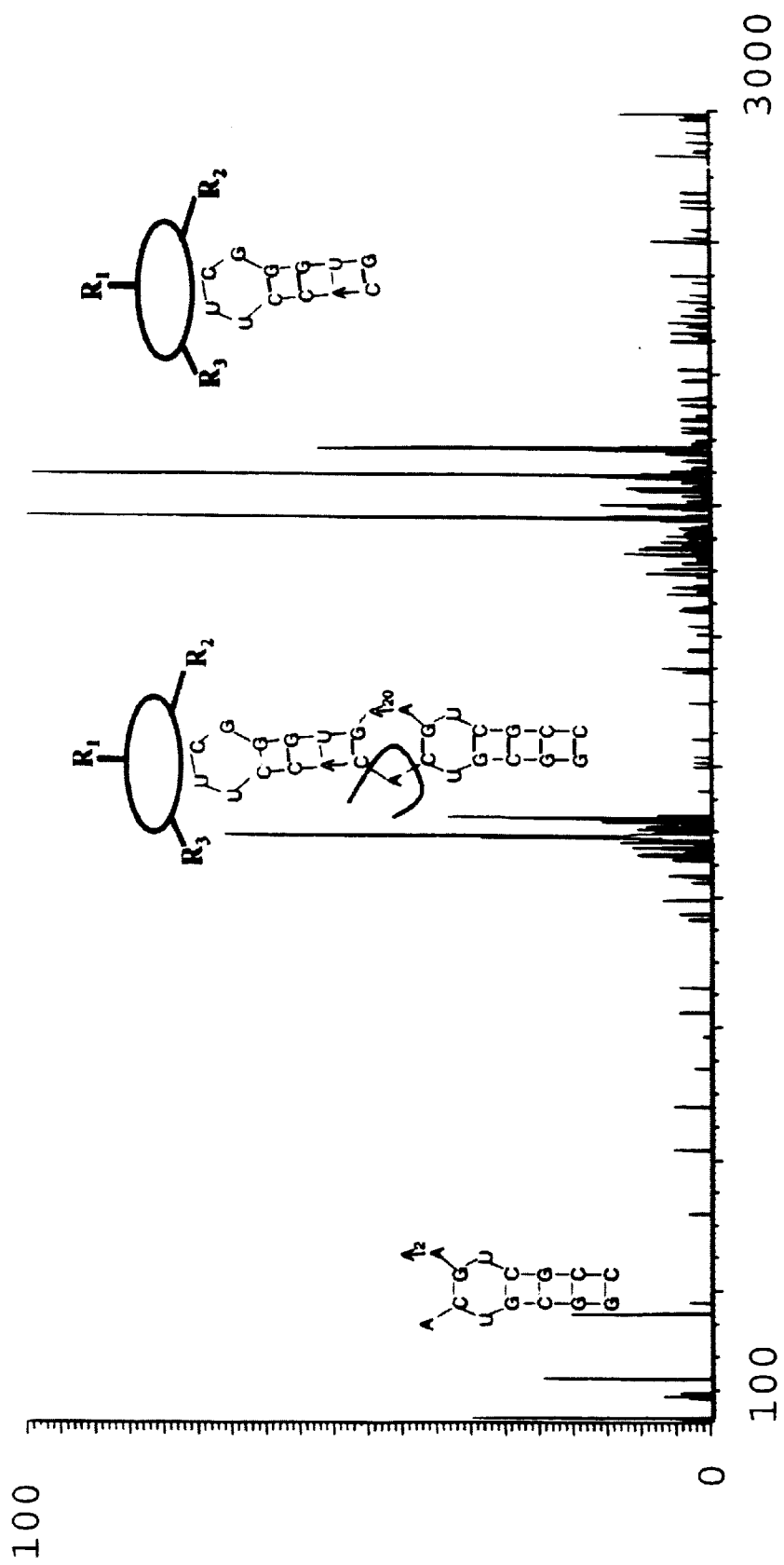
FIG. 4 shows the ESI-CID-MS spectrum of a combinatorial library member-27 mer RNA/DNA hybrid noncovalent complex ion of m/z 1919.0.
Figure 5:
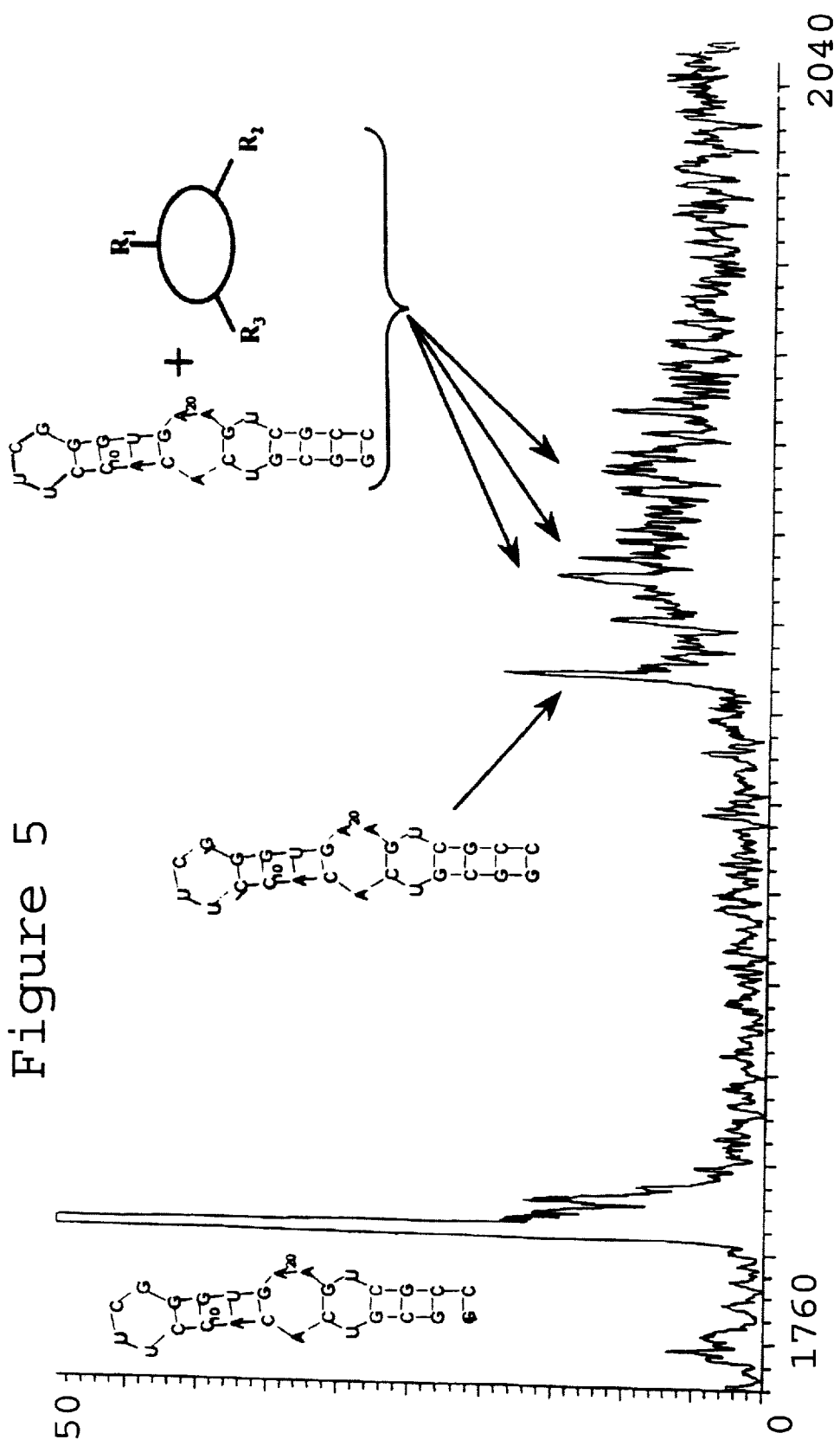
FIG. 5 shows the ESI-MS of a combinatorial library screened against a 27 mer RNA/DNA hybrid.

Similarly, the ions at m/z 1897.8, that correspond to the complex of a library member with the 27 mer target, were isolated via an ion-isolation procedure and then subjected to CID using the same conditions used for the previous complex, and the data was averaged for 3 minutes. The resulting mass spectrum (FIG. 4) revealed six major fragment ions at m/z values of 1005.8, 1065.6, 1162.8, 2341.1, 2406.3 and 2446.0. The three fragments at m/z 1005.8, 1065.6 and 1162.8 correspond to the $w_6^{(2-)}$, $a_7\text{-}B^{(2-)}$ and $w_7^{(2-)}$ ions from the nucleic acid target. The three ions at higher masses of 2341.1, 2406.3 and 2446.0 correspond to the $a_{20}\text{-}B^{(3-)}$ ion+566 Da, $w_{21}^{(3-)}$ ion+566 Da and the $a_{21}\text{-}B^{(3-)}$ ion+566 Da. The data demonstrates at least two findings: first, since only the nucleic acid can be activated to give fragment ions in this ESI-CID experiment, the observation of new fragment ions indicates that the 1897.8 ion peak results from a library member bound to the nucleic acid target. Second, the library member has a molecular weight of 566. This library member binds to the GCUU tetraloop or the four base pairs in the stem structure of the nucleic acid target (the RNAIDNA chimeric corresponding to the 16S rRNA A site) and it does not bind to the bulged A site or the 6-base pair stem that contains the U*U mismatch pair of the nucleic acid target.

Further detail on the binding site of the library member can be gained by studying its interaction with and influence on fragmentation of target nucleic acid molecules where the positions of deoxynucleotide incorporation are different.

Example 5

Determining the Identity of a Member of a Combinatorial Library that Binds to a Biomolecular Target and the Location of Binding to the Target A 10 mM solution of the 27-mer RNA target, corresponding to the 16S rRNA A-site that contains 3 dA residues (from Example 1), in 100 mM ammonium acetate at pH 7.4 was treated with a solution of paromomycin acetate and an aliquot of a DMSO solution of a second combinatorial library to be screened. The amount of paromomycin added was adjusted to afford a final concentration of 150 nM. Likewise, the amount of DMSO solution of the library that was added was adjusted so that the final concentration of each of the 216 member components of the library was ~150 nM. The solution was infused into a Finnigan LCQ ion trap mass spectrometer and ionized by electrospray. A range of 1000–3000 m/z was scanned for ions of the nucleic acid target and its complexes generated from binding with paromomycin and members of the combinatorial library. Typically 200 scans were averaged for 5 minutes. The ions from the nucleic acid target were observed at m/z 1784.4 for the $(M\text{-}5H)^{5-}$ ion and 2230.8 for the $(M\text{-}4H)^{4-}$ ion. The paromomycin-nucleic acid complex was also observed as signals of the $(M\text{-}5H)^{5-}$ ion at m/z 1907.1 and the $(M\text{-}4H)^{4-}$ ion at m/z 2384.4 u.

Analysis of the spectrum for complexes of members of the combinatorial library and the nucleic acid target revealed several new signals that arise from the noncovalent binding of members of the library with the nucleic acid target. At least six signals for such noncovalent complexes were observed in the mass spectrum. Of these the signal at the lowest m/z value was found to be a very strong binder to the nucleic acid target. Comparison of the abundance of this ligand-nucleic acid complex ion with the abundance of the ion derived from the paromomycin-nucleic acid complex revealed a relative binding affinity (apparent $K_D$) that was similar to that for paromomycin.

MS/MS experiments, with ~6 minutes of signal averaging, were also performed on this complex to further establish the molecular weight of the bound ligand. A mass of 730.0±2 Da was determined, since the instrument performance was accurate only to ±1.5 Da. Based on this observed mass of the bound ligand and the known structures of the scaffold and substituents used in generating the combinatorial library, the structure of the ligand was determined to bear either of three possible combinations of substituents on the PAP5 scaffold. The MS/MS analysis of this complex also revealed weak protection of the dA residues of the hybrid RNA/DNA from CID cleavage. Observation of fragments with mass increases of 730 Da showed that the molecule binds to the upper stem-loop region of the rRNA target.

Example 6

Determining the Identity of Members of a Combinatorial Library that Bind to a Biomolecular Target and the Location of Binding to the Target A 10 mM solution of the 27-mer RNA target, corresponding to the 16S rRNA A-site that contains 3 dA residues (from Example 1), in 100 mM anunonium acetate at pH 7.4 was treated with a solution of paromomycin acetate and an aliquot of a DMSO solution of a third combinatorial library to be screened. The amount of paromomycin added was adjusted to afford a final concentration of 150 nM. Likewise, the amount of DMSO solution of the library that was added was adjusted so that the final concentration of each of the 216 member components of the library was ~150 nM. The solution was infused into a Finnigan LCQ ion trap mass spectrometer and ionized by electrospray. A range of 1000–3000 m/z was scanned for ions of the nucleic acid target and its complexes generated from binding with paromomycin and members of the combinatorial library. Typically 200 scans were averaged for 5 minutes. The ions from the nucleic acid target were observed at m/z 1784.4 for the $(M\text{-}5H)^{5-}$ ion and 2230.8 for the $(M\text{-}4H)^{4-}$ ion. The paromomycin-nucleic acid complex was also observed as signals of the (M-5H)$^{5-}$ ion at m/z 1907.1 and the (M-4H)$^{4-}$ ion at m/z 2384.4 u.

Analysis of the spectrum for complexes of members of the combinatorial library and the nucleic acid target revealed several new signals that arise from the noncovalent binding of members of the library with the nucleic acid target. At least two major signals for such noncovalent complexes were observed in the mass spectrum. MS/MS experiments, with ~6 minutes of signal averaging, were also performed on these two complexes to further establish the molecular weights of the bound ligands.

The first complex was found to arise from the binding of a molecule of mass 720.2±2 Da to the target. Two possible structures were deduced for this member of the combinatorial library based on the structure of the scaffold and substituents used to build the library. These include a structure of mass 720.4 and a structure of mass 721.1. MS/MS experiments on this ligand-target complex ion using CID demonstrated strong protection of the A residues in the bulge structure of the target. Therefore this ligand must bind strongly to the bulged dA residues of the RNA/DNA target.

Figure 6:
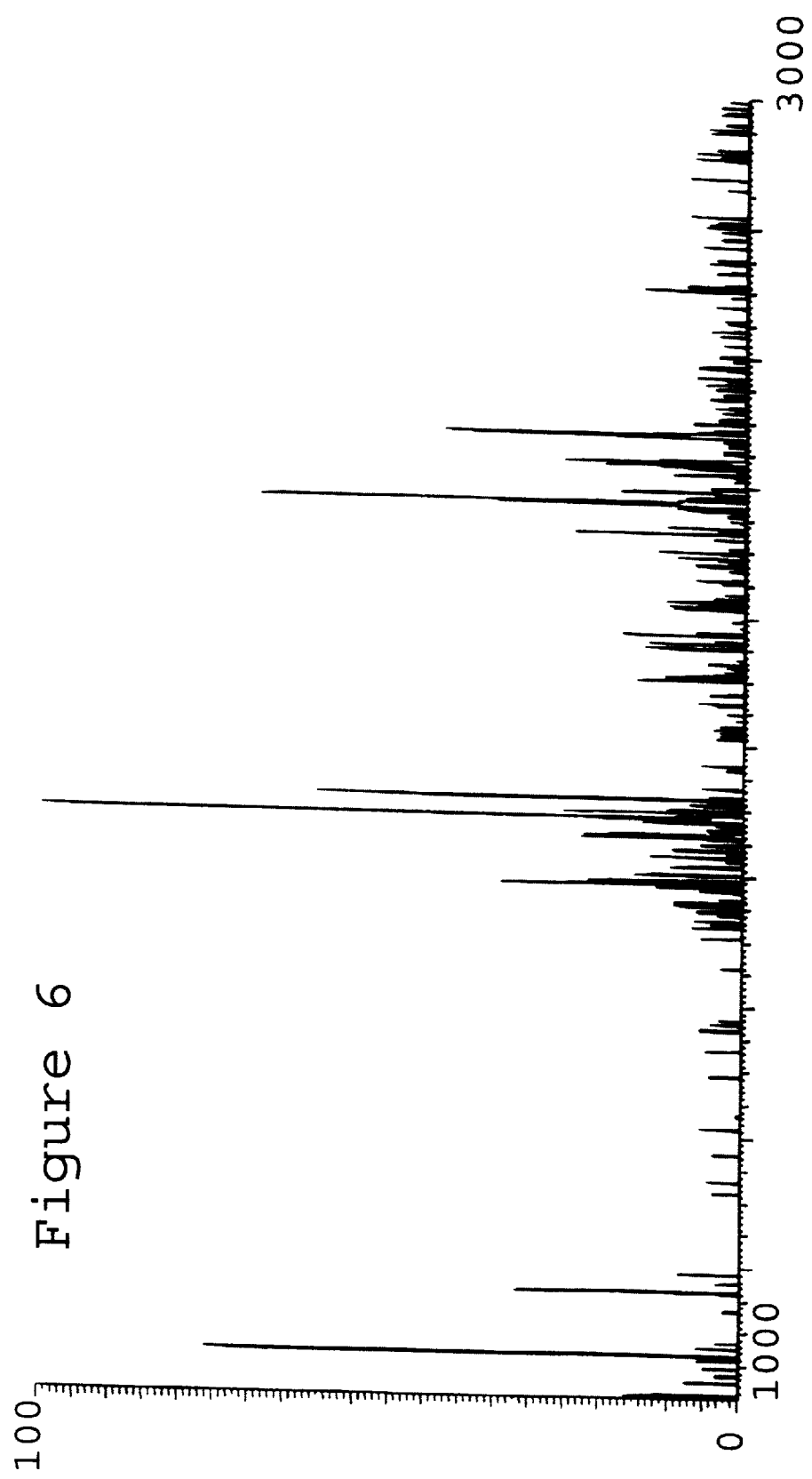
FIG. 6 shows the ESI-MS-MS analysis of the signal of m/z 1917.8 u arising from the binding of a member of mass 665 from another combinatorial library.
Figure 7:
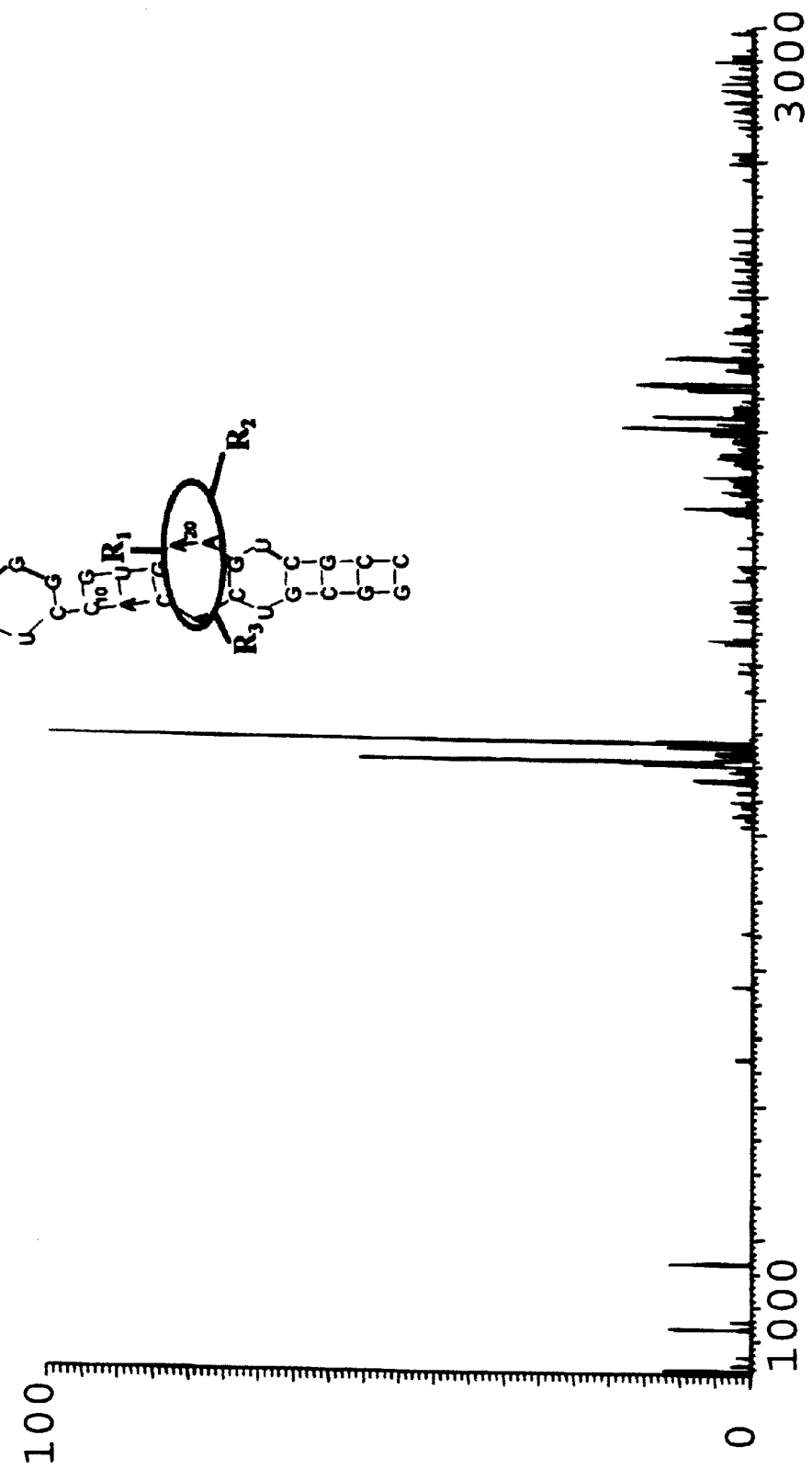
FIG. 7 shows the ESI-MS-MS analysis of the signal of m/z 1934.3 u arising from the binding of a member of mass 720 from a library.

The second major complex observed from the screening of this library was found to arise from the binding of a molecule of mass 665.2±2 Da to the target. Two possible structures were deduced for this member of the library based on the structure of the scaffold and substituents used to build the library. MS/MS experiments on this ligand-target complex ion using CID demonstrated strong fragmentation of the target. Therefore this ligand must not bind strongly to the bulged dA residues of the RNA/DNA target. Instead the fragmentation pattern, together with the observation of added mass bound to fragments from the loop portion of the target, suggest See FIG. 6. that this ligand must bind to residues in the loop region of the RNA/DNA target.

Example 7

Simultaneous Screening of a Combinatorial Library of Compounds Against Two Nucleic Acid Targets The two RNA targets to be screened are synthesized using automated nucleic acid synthesizers. The first target (A) is the 27-mer RNA corresponding to the 16S rRNA A site and contains 3 dA residues, as in Example 1. The second target (8) is the 27-mer RNA bearing 3 dA residues, and is of identical base composition but completely scrambled sequence compared to target (A). Target (B) is modified in the last step of automated synthesis by the addition of a mass modifiing tag, a polyethylene glycol (PEG) phosphoramidite to its 5'-terminus. This results in a mass increment of 3575 in target (B), which bears a mass modifying tag, compared to target (A).

A solution containing 10 mM target (A) and 10 mM mass modified target (B) is prepared by dissolving appropriate amounts of both targets into 100 mM ammonium acetate at pH 7.4. This solution is treated with a solution of paromomycin acetate and an aliquot of a DMSO solution of the combinatorial library to be screened. The amount of paromomycin added is adjusted to afford a final concentration of 150 nM. Likewise, the amount of DMSO solution of the library that is added is adjusted so that the final concentration of each of the 216 member components of the library is ~150 nM. The library members are molecules with masses in the 700–750 Da range. The solution is infused into a Finnigan LCQ ion trap mass spectrometer and ionized by electrospray. A range of 1000–3000 m/z is scanned for ions of the nucleic acid target and its complexes generated from binding with paromomycin and members of the combinatorial library. Typically 200 scans are averaged for 5 minutes.

The ions from the nucleic acid target (A) are observed at m/z 1486.8 for the (M-6H)$^{6-}$ ion, 1784.4 for the (M-5H)$^{5-}$ ion and 2230.8 for the (M-4H)$^{4-}$ ion. Signals from complexes of target (A) with members of the library are expected to occur with m/z values in the 1603.2–1611.6, 1924.4–1934.4 and 2405.8–2418.3 ranges.

Signals from complexes of the nucleic acid target (B), that bears a mass modifying PEG tag, with members of the combinatorial library are observed with m/z values in the 2199–2207.4, 2639–2649 and 3299–3311 ranges. Therefore, the signals of noncovalent complexes with target (B) are cleanly resolved from the signals of complexes arising from the first target (A). New signals observed in the mass spectrum are therefore readily assigned as arising from binding of a library member to either target (A) or target (B).

Extension of this mass modifying technique to larger numbers of targets via the use of unique, high molecular weight neutral and cationic polymers allows for the simultaneous screening of more than two targets against individual compounds or combinatorial libraries.

Example 8

Simultaneous Screening of a Combinatorial Library of Compounds Against Two Peptide Targets The two peptide targets to be screened are synthesized using automated peptide synthesizers. The first target (A) is a 27-mer polypeptide of known sequence. The second target (B) is also a 27-mer polypeptide that is of identical amino acid composition but completely scrambled sequence compared to target (A). Target (B) is modified in the last step of automated synthesis by the addition of a mass modifying tag, a polyethylene glycol (PEG) chloroformate to its amino terminus. This results in a mass increment of ~3600 in target (B), which bears a mass modifying tag, compared to target (A).

A solution containing 10 mM target (A) and 10 mM mass modified target (B) is prepared by dissolving appropriate amounts of both targets into 100 mM ammonium acetate at pH 7.4. This solution is treated an aliquot of a DMSO solution of the combinatorial library to be screened. The amount of DMSO solution of the library that is added is adjusted so that the final concentration of each of the 216 member components of the library is ~150 nM. The library members are molecules with masses in the 700–750 Da range. The solution is infused into a Finnigan LCQ ion trap mass spectrometer and ionized by electrospray. A range of 1000–3000 m/z is scanned for ions of the polypeptide target and its complexes generated from binding with members of the combinatorial library. Typically 200 scans are averaged for 5 minutes.

The ions from the polypeptide target (A) and complexes of target (A) with members of the library are expected to occur at much lower m/z values that the signals from the polypeptide target (B), that bears a mass modifying PEG tag, and its complexes with members of the combinatorial library Therefore, the signals of noncovalent complexes with target (B) are cleanly resolved from the signals of complexes arising from the first target (A). New signals observed in the mass spectrum are therefore readily assigned as arising from binding of a library member to either target (A) or target (B). In this fashion, two or more peptide targets may be readily screened for binding against an individual compound or combinatorial library.

Example 9

Gas-phase Dissociation of Nucleic Acids for Determination of Structure

Nucleic acid duplexes can be transferred from solution to the gas phase as intact duplexes using electrospray ionization and detected using a Fourier transform, ion trap, quadrupole, time-of-flight, or magnetic sector mass spectrometer. The ions corresponding to a single charge state of the duplex can be isolated via resonance ejection, off-resonance excitation or similar methods known to those familiar in the art of mass spectrometry. Once isolated, these ions can be activated energetically via blackbody irradiation, infrared multiphoton dissociation, or collisional activation. This activation leads to dissociation of glycosidic bonds and the phosphate backbone, producing two series of fragment ions, called the w-series (having an intact 3'-terminus and a 5'-phosphate following internal cleavage) and the a-Base series (having an intact 5'-terminus and a 3'-furan). These product ions can be identified by measurement of their mass/charge ratio in an MS/MS experiment.

Figure 8:
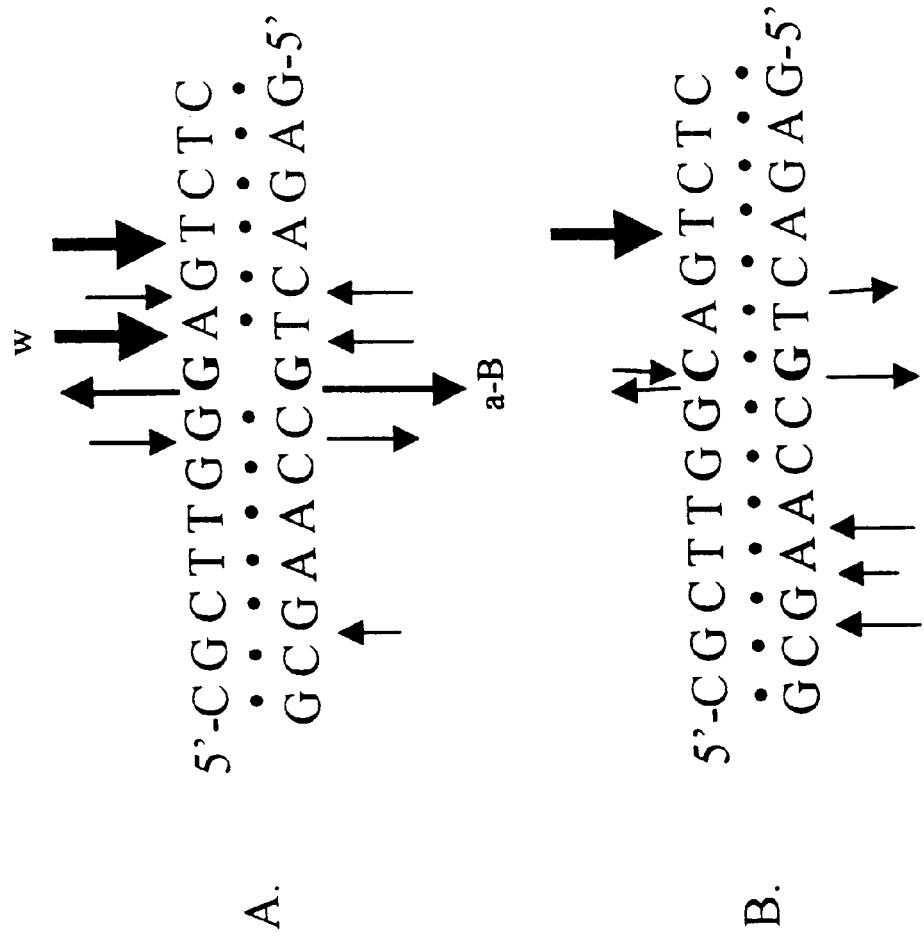
FIGS. 8 and 9 show graphical representations of the abundances of w and a-Base ions resulting from (CID) of ions from a DNA:DNA duplex.
Figure 9:
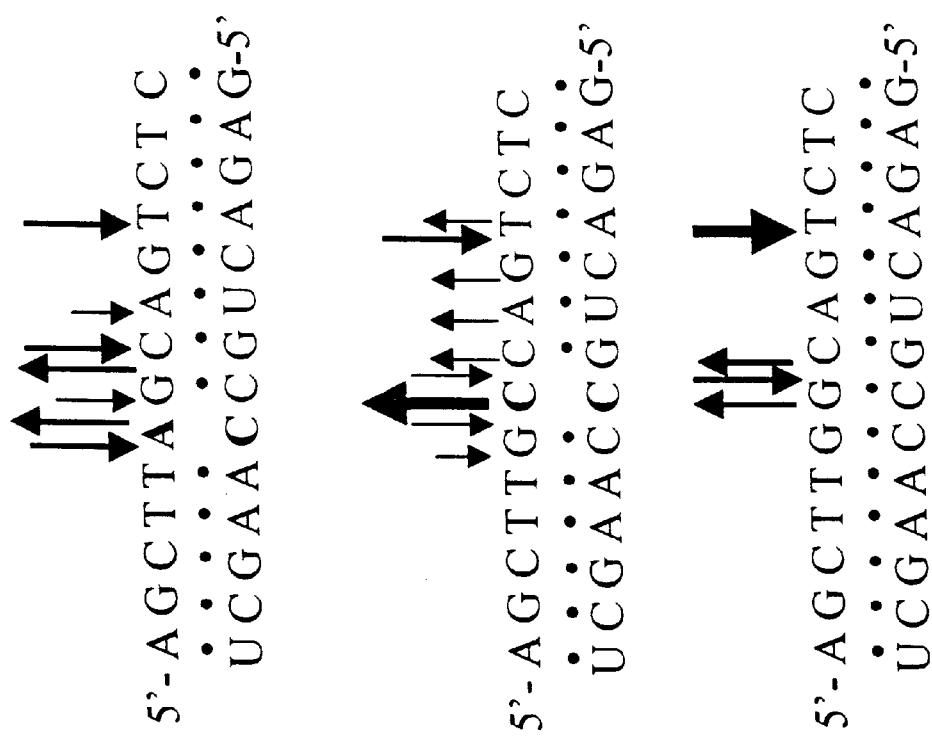

An example of the power of this method is presented in FIGS. 8 and 9. Shown in FIG. 8 part A is a graphical representation of the abundances of the w and a-Base ions resulting from collisional activation of the $(M-5H)^{5-}$ ions from a DNA:DNA duplex containing a G-G mismatch base pair. The w series ions are highlighted in black and point toward the duplex, while the a-Base series ions are highlighted in gray and point away from the duplex. The more abundant the fragment ion, the longer and thicker the respective arrow. Substantial fragmentation is observed in both strands adjacent to the mismatched base pair. The results obtained following collisional activation of the control DNA:DNA duplex ion is shown in FIG. 8 part B. Some product ions are common, but the pattern of fragmentation differs significantly from the duplex containing the mismatched base pair. Analysis of the fragment ions and the pattern of fragmentation allows the location of the mismatched base pair to be identified unambiguously. In addition, the results suggest that the gas phase structure of the duplex DNA ion is altered by the presence of the mismatched pair in a way which facilitates fragmentation following activation.

A second series of experiments with three DNA:RNA duplexes are presented in FIG. 9 In the upper figure, an A-C mismatched pair has been incorporated into the duplex. Extensive fragmentation producing w and a-Base ions is observed adjacent to the mismatched pair. However, the increased strength of the glycosidic bond in RNA limits the fragmentation of the RNA strand. Hence, the fragmentation is focused onto the DNA strand. In the central figure, a C-C mismatched base pair has been incorporated into the duplex, and enhanced fragmentation is observed at the site of the mismatched pair. As above, fragmentation of the RNA strand is reduced relative to the DNA strand. The lower figure contains the fragmentation observed for the control RNA:DNA duplex containing all complementarybase pairs. A common fragmentation pattern is observed between the G5-T4 bases in all three cases. However, the extent of fragmentation is reduced in the complementary duplexes relative to the duplexes containing base pair mismatches.

Example 10

Figure 10:
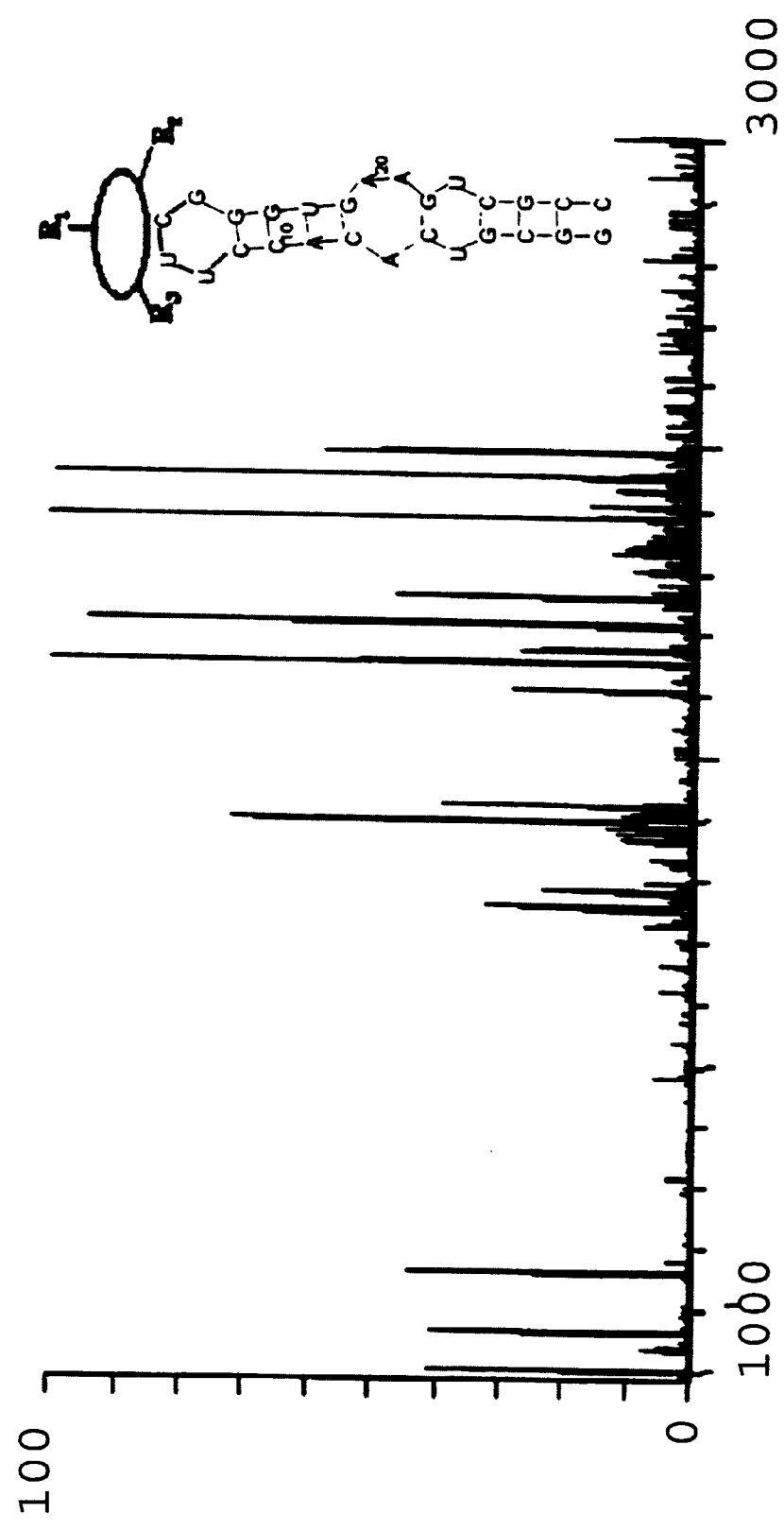
FIGS. 10, 11 and 12 depict MASS analyses to determine the binding of ligands to a molecular interaction site.
Figure 11:
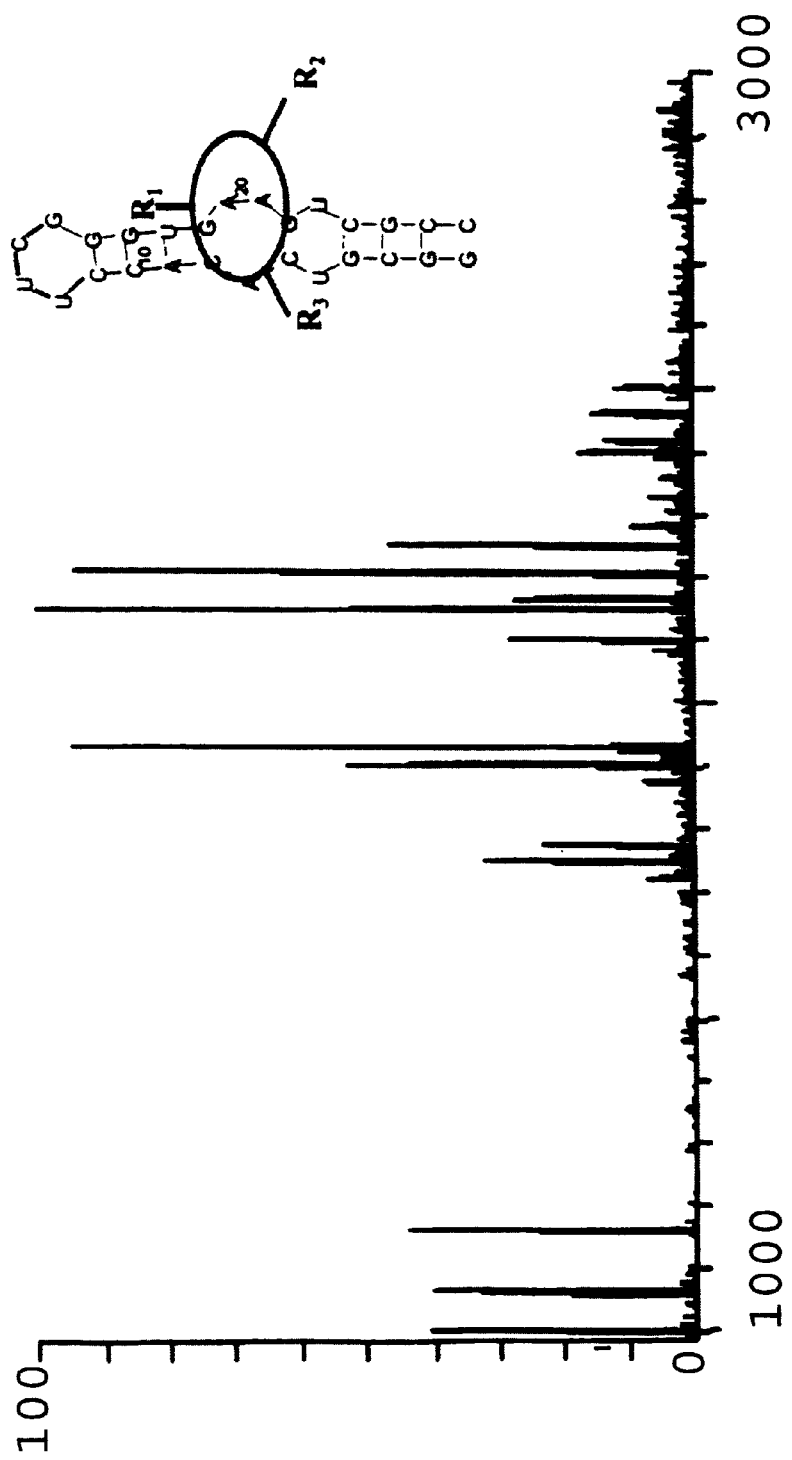

MASS Analysis of RNA—Ligand Complex to Determine Binding of Ligand to Molecular Interaction Site The ability to discern through mass spectroscopy whether or not a proposed ligand binds to a molecular interaction site of an RNA can be shown. FIGS. 10 and 11 depict the mass spectroscopy of an RNA segment having a stem-loop structure with a ligand, schematically illustrated by an unknown, functionalized molecule. The ligand is combined with the RNA fragment under conditions selected to facilitate binding and the result in complex is analyzed by a multi target affinity/specificity screening (MASS) protocol. This preferably employs electrospray ionization Fourier transform ion cyclotron resonance mass spectrometry as described hereinbefore and in the references cited herein. "Mass chromatography" as described above permits one to focus upon one bimolecular complex and to study the fragmentation of that one complex into characteristic ions. The situs of binding of ligand to RNA can, thus, be determined through the assessment of such fragments; the presence of fragments corresponding to molecular interaction site and ligand indicating the binding of that ligand to that molecular interaction site.

FIG. 10 depicts a MASS Analysis of a Binding Location for a non-A Site Binding molecule. The isolation through "mass chromatography" and subsequent dissociation of the (M-5H)5–complex is observed at m/z 1919.8. The mass shift observed in select fragments relative to the fragmentation observed for the free RNA provides information about where the ligand is bound. The (2–) fragments observed below m/z 1200 correspond to the stem structure of the RNA; these fragments are not mass shifted upon Complexation. This is consistent with the ligand not binding to the stem structure.

FIG. 11 shows a MASS Analysis of Binding Location for the non-A Site Binding molecule. Isolation (i.e. "mass chromatography") and subsequent dissociation of the (M-5H)5–complex observed at m/z 1929.4 provides significant protection from fragmentation in the vicinity of the A-site. This is evidenced by the reduced abundance of the w and a-base fragment ions in the 2300–2500 m/z range. The mass shift observed in select fragments; relative to the fragmentation observed for the free RNA provides information about where the ligand is bound. The exact molecular mass of the RNA can act as an internal or intrinsic, mass label for identification of molecules bound to the RNA. The (2–) fragments observed below m/z 1200 correspond to the stem structure of the RNA. These fragments are not mass shifted upon Complexation—consistent with ligand not being bound to the stem structures. Accordingly, the location of binding of ligands to the RNA can be determined.

Example 11

Determination of Specificity and Affinity of Ligand Libraries to RNA Targets A preferred first step of MASS screening involves mixing the RNA target (or targets) with a combinatorial library of ligands designed to bind to a specific site on the target molecule(s). Specific noncovalent complexes formed in solution between the target(s) and aly library members are transferred into the gas phase and ionized by ESI. As described herein, from the measured mass difference between the complex and the free target, the identity of the binding ligand can be determined. The dissociation constant of the complex can be determined in two ways: if a ligand with a known binding affinity for the target is available, a relative Kd can be measured by using the known ligand as an internal control and measuring the abundance of the unknown complex to the abundance of the control, alternatively, if no internal control is available, Kd's can be determined by making a series of measurements at different ligand concentrations and deriving a Kd value from the "titration" curve.

Because screening preferably employs large numbers of similar, preferably combinatorially derived, compounds, it is preferred that in addition to determining whether something from the library binds the target, it is also determined which compound(s) are the ones which bind to the target. With highly precise mass measurements, the mass identity of an unknown ligand can be constrained to a unique elemental composition. This unique mass is referred to as the compound's "intrinsic mass label." For example, while there are a large number of elemental compositions which result in a molecular weight of approximately 615 Da, there is only one elemental composition ($C_{23}H_{45}N_5O_{14}$) consistent with a monoisotopic molecular weight of 615.2963012 Da. For example, the mass of a ligand (paromomycin in this example) which is noncovalently bound to the 16S A-site was determined to be 615.2969±0.0006 (mass measurement error of 1 ppm) using the free RNA as an internal mass standard. A mass measurement error of 100 ppm does not allow unambiguous compound assignment and is consistent with nearly 400 elemental compositions containing only atoms of C, H, N, and O. The isotopic distributions shown in the expanded views are primarily a result of the natural incorporation of 13C atoms; because high performance FTICR can easily resolve the 12C–13C mass difference we can use each component of the isotopic cluster as an internal mass standard. Additionally, as the theoretical isotope distribution of the free RNA can be accurately simulated, mass differences can be measured between "homoisotopic" species (in this example the mass difference is measured between species containing four 13C atoms).

Once the identity of a binding ligand is determined, the complex is isolated in the gas phase (i.e. "mass chromatography") and dissociated. By comparing the fragmentation patterns of the free target to that of the target complexed with a ligand, the ligand binding site can be determined. Dissociation of the complex is performed either by collisional activated dissociation (CAD) in which fragmentation is effected by high energy collisions with neutrals, or infrared multiphoton dissociation (IRMPD) in which photons from a high power IR laser cause fragmentation of the complex.

Figure 12:
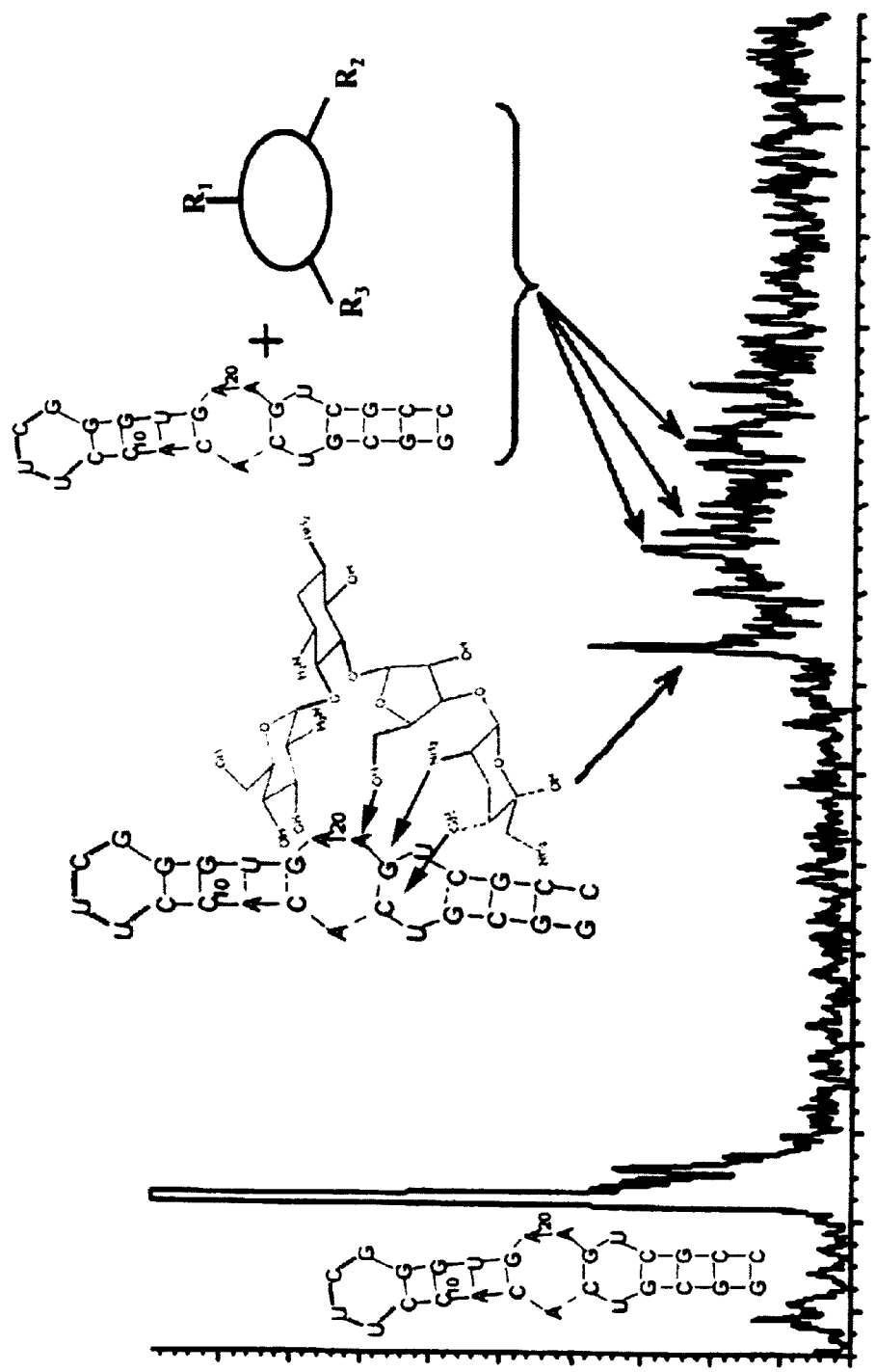

A 27-mer RNA containing the A-site of the 16S rRNA was chosen as a target fir validation experiments. See FIG. 12. The aminoglycoside paromomycin is known to bind to the unpaired adenosine residues with a Kd of 200 nM and was used as an internal standard. The target was at an initial concentration of 10 mM while the paromomycin and each of the 216 library members were at an initial concentration of 150 nM. While this example was performed on a quadrupole ion trap which does not afford the high resolution or mass accuracy of the FTICR, it serves to illustrate the MASS concept. Molecular ions corresponding to the free RNA are observed at m/z 1784.4 (M-5H+)5- and 2230.8 4 (M-4H+) 4-. The signals from the RNA-paromomycin internal control are observed at m/z 1907.1 4 (M-5H+)5- and 2384.4 4 (M-4H+)4-. In addition to the expected paromomycin complex, a number of complexes are observed corresponding to binding of library members to the target. See FIG. 13.

One member of this library (MW=675.8+1.5) forms a strong complex with the target but MS/MS studies reveal that the ligand does not offer protection of A-site fragmentation and therefore binds to the loop region. Another member of Isis 113069 having an approximate mass of 743.8+1.5 demonstrates strong binding to the target and, as evidenced by MS/MS experiments provides protection of the unpaired A residues, consistent with binding at the A-site.

The rapid and parallel nature of the MASS approach allows large numbers of compounds to be screened against multiple targets simultaneously, resulting in greatly enhanced sample throughput and information content. In a single assay requiring less than 15 minutes, MASS can screen 10 targets against a library containing over 500 components and report back which compounds bind to which targets, where they bind, and with what binding affinity.

Example 12

High Precision ESI-FTICR Mass Measurement Of 16S A Site RNA/Paromomycin Complex

Figure 13:
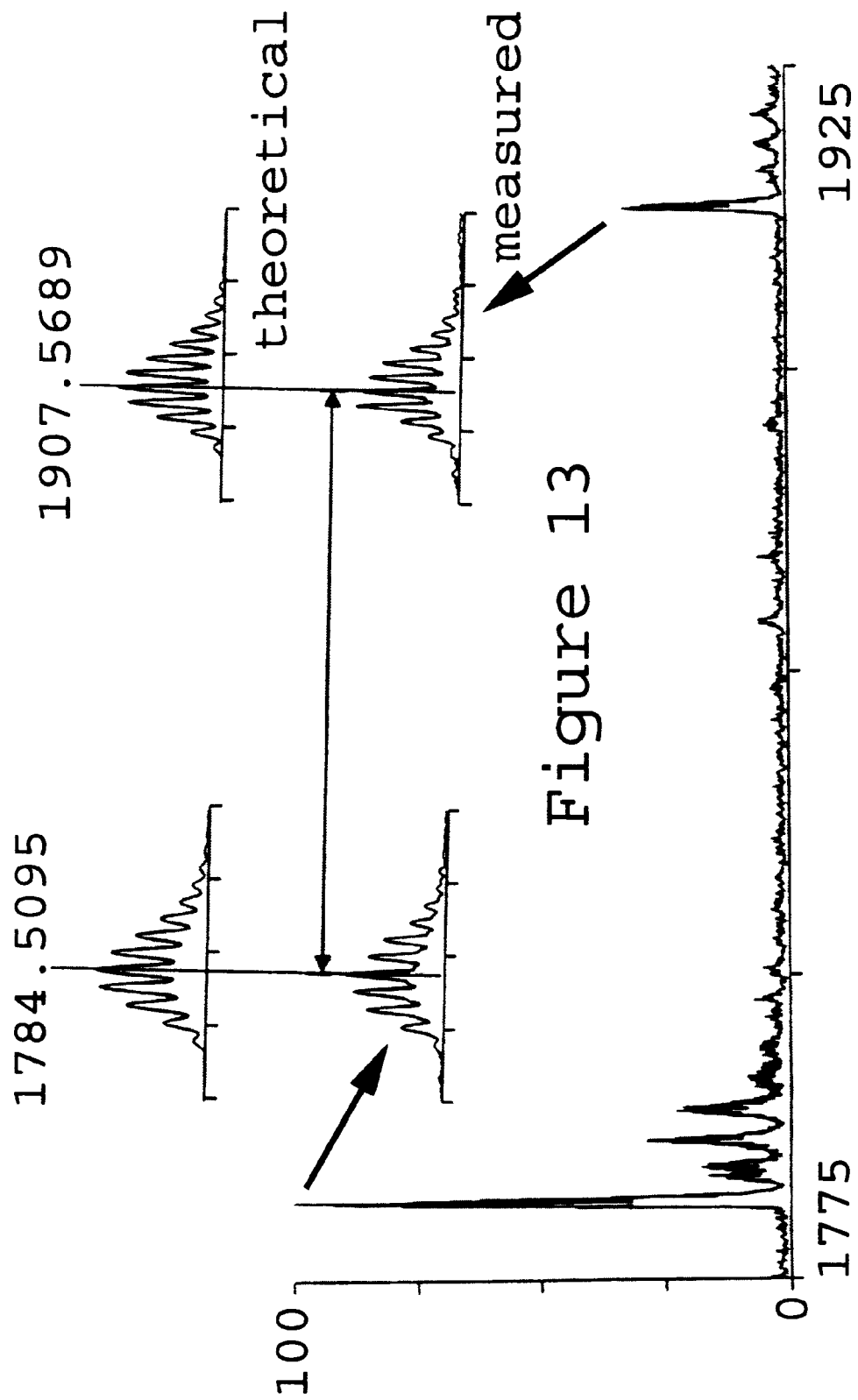
FIG. 13 depicts high precision ESI-FTICR mass measurement of the interaction of the 16S A site of an RNA complexed with paromomycin.

Electrospray ionization Fourier transform ion cyclotron resonance mass spectrometry was performed on a solution containing 5 mM 16S RNA (the 27-mer construct shown in FIG. 24) and 500 nM paromomycin is depicted in FIG. 13. A 1:1 complex was observed between the paromomycin and the RNA consistent with specific aminoglycoside binding at the A-site. The insets show the measured and calculated isotope envelopes of the (M-5H+)5- species of the free RNA and the RNA-paromomycin complex. High precision mass measurements were acquired using isotope peaks of the $(M-5H^+)^{5-}$ and $(M-4H^+)^{4-}$ charge states of the free RNA as internal mass standards and measuring the m/z difference between the free and bound RNA.

Example 13

Mass of 60-Member Library Against 16S A-Site RNA

Figure 14:
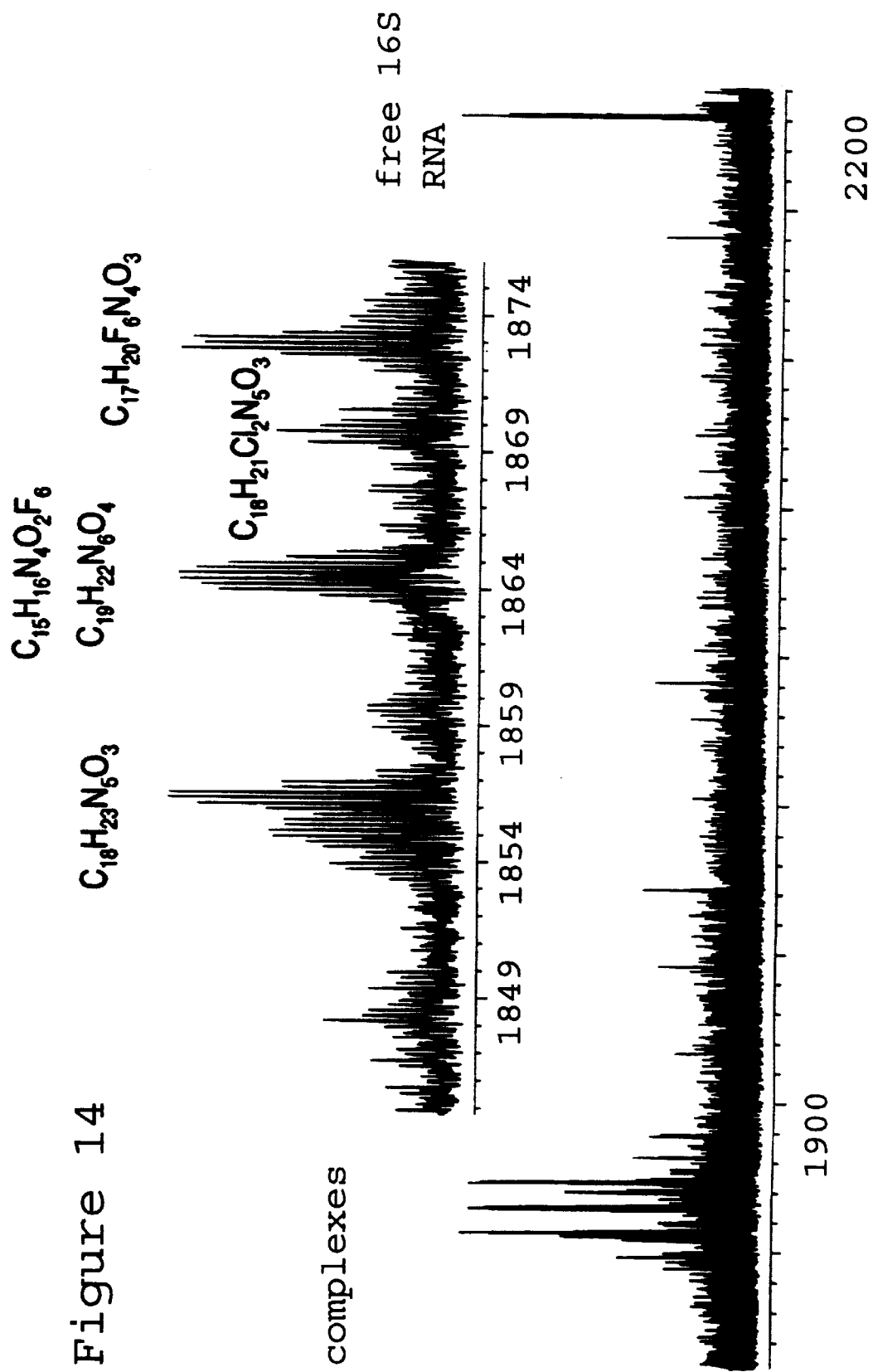
FIG. 14 depicts FTMS spectrum obtained from a mixture of a 16S RNA model (10 $\mu$M) and a 60-member combinatorial library.

FTMS spectrum was obtained from a mixture of a 16S RNA model (10 mM) and a 60-member combinatorial library. Signals from complexes are highlighted in the insert. Binding of a combinatorial library containing 60 members to the 16S RNA model have been examined under conditions where each library member was present at 5-fold excess over the RNA. As shown in FIG. 14, complexes between the 16S RNA and ~5 ligands in the library were observed.

Figure 15:
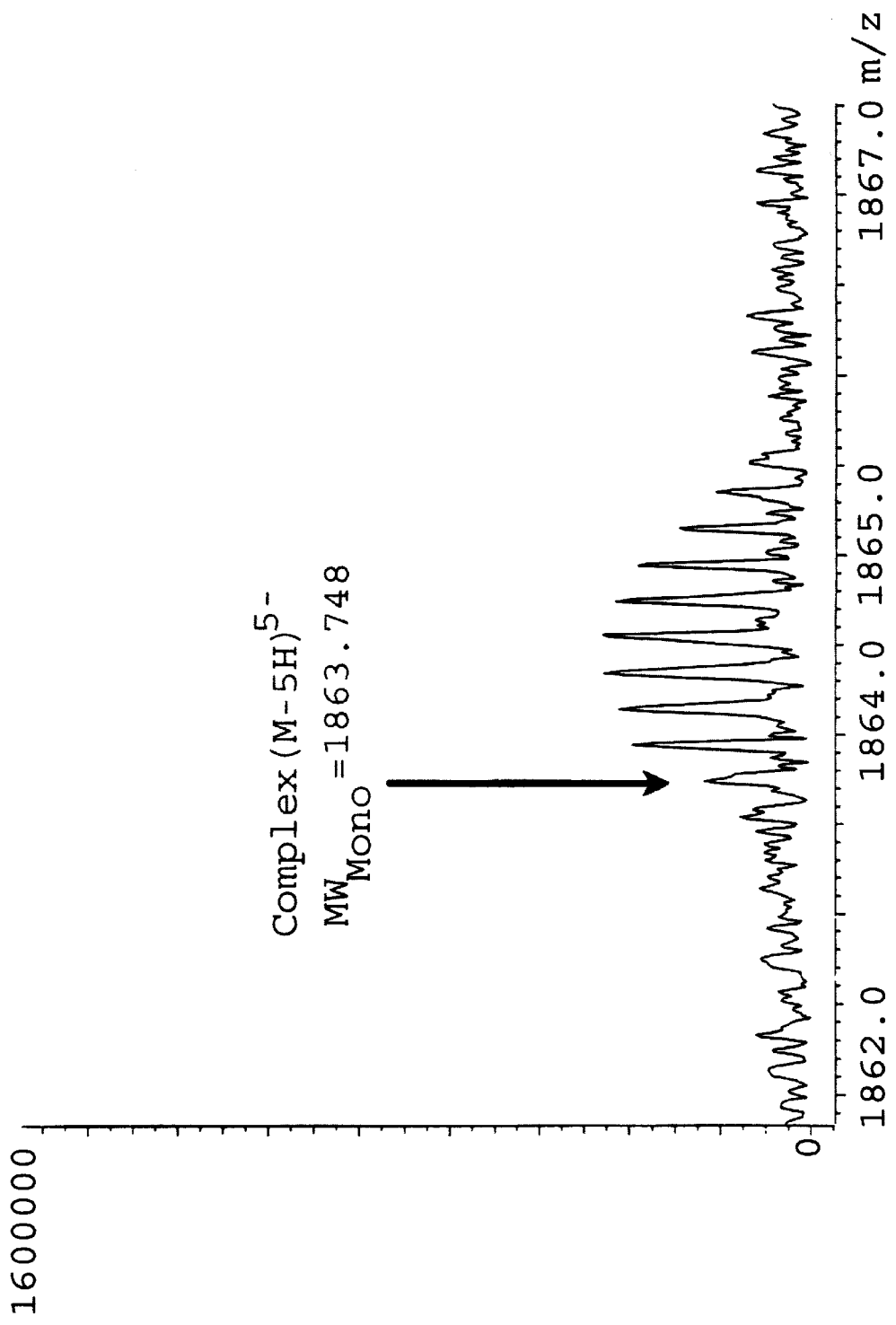
FIG. 15 depicts an expanded view of the 1863 complex from FIG. 15.

An expanded view of the 1863 complex from FIG. 14 is shown in FIG. 15. Two of the compounds in the library had a nominal mass of 398.1 Da. Their calculated molecular weights based on molecular formulas indicate that they differ in mass by 46 mDa. Accurate measurement of the molecular mass for the respective monoisotopic (all $^{12}C$, $^{14}N$, and $^{16}O$) $[M-5H]^{5-}$ species of the complex (m/z 1863.748) and the free RNA (m/z 1784.126) allowed the mass of the ligand to be calculated as 398.110±009 Da.

Figure 16:
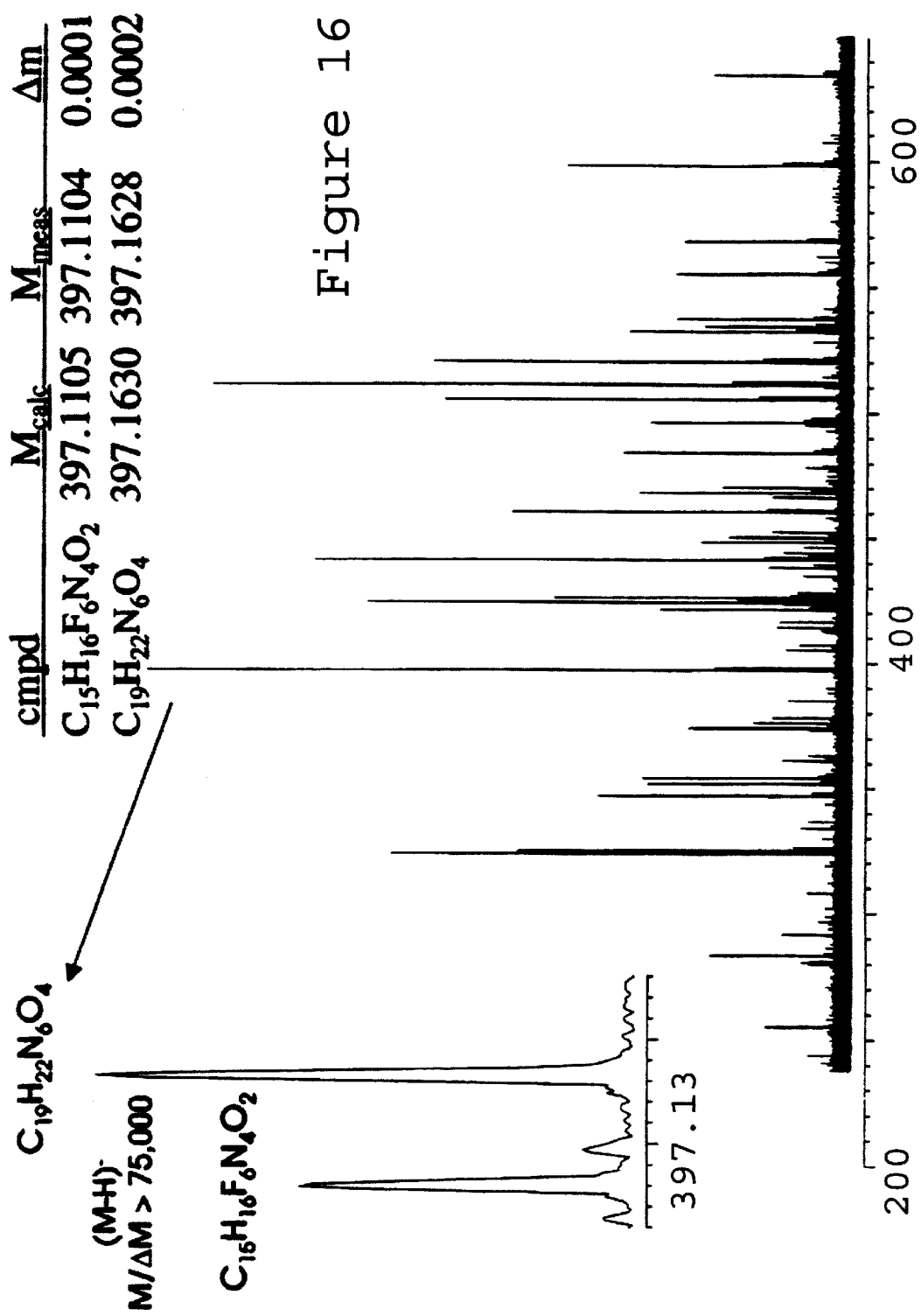
FIG. 16 depicts mass of a binding ligand determined from a starting library of compounds.

FIG. 16 shows high resolution ESI-FTICR spectrum of the library used in FIGS. 14 and 15, demonstrating that both library members with animal molecular weight of 398.1 were present in the synthesized library.

Example 14

Compound Identification From a 60-Member Combinatorial Library with MASS

Figure 17:
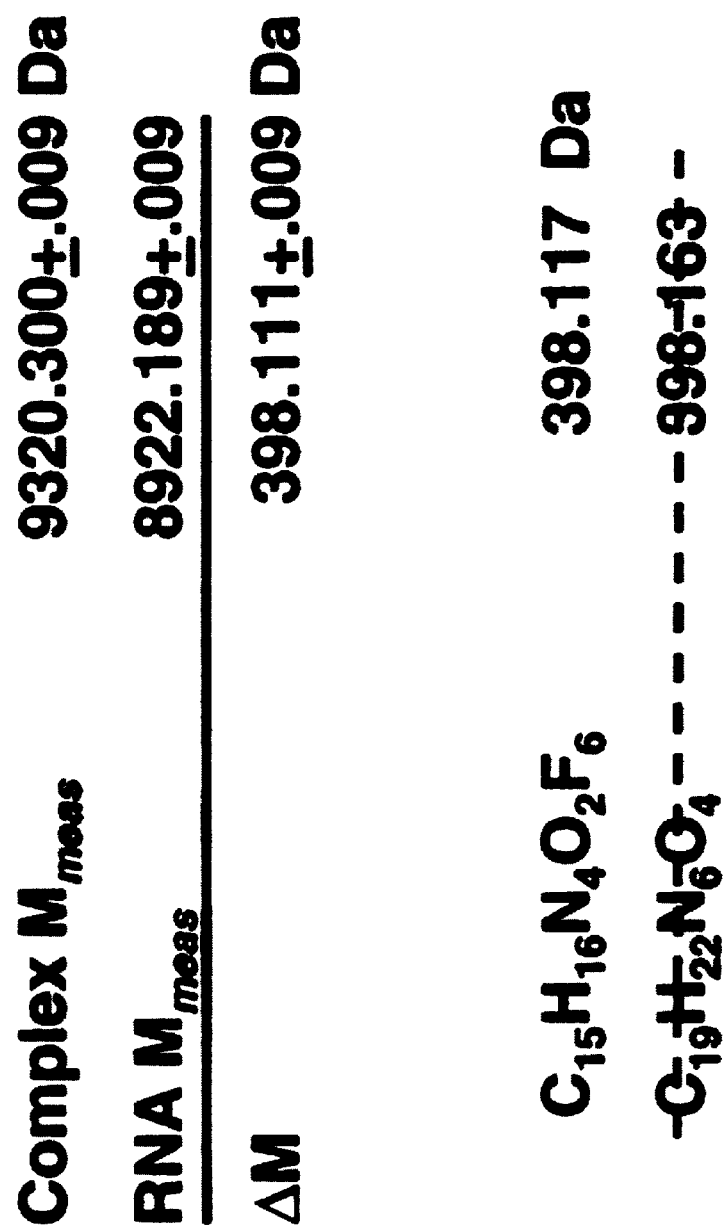
FIG. 17 depicts high resolution ESI-FTICR spectrum of the library used in FIGS. 15 and 16.

Based on the high precision mass measurement of the complex, the mass of the binding ligand was determined to be consistent with the library member having a chemical formula of $C_{15}H_{16}N_4O_2F_6$ and a molecular weight of 398.117 Da (FIG. 17). Thus, the identity of the binding ligand was unambiguously established.

Example 15

Elemental Composition Constraints

Figure 18:
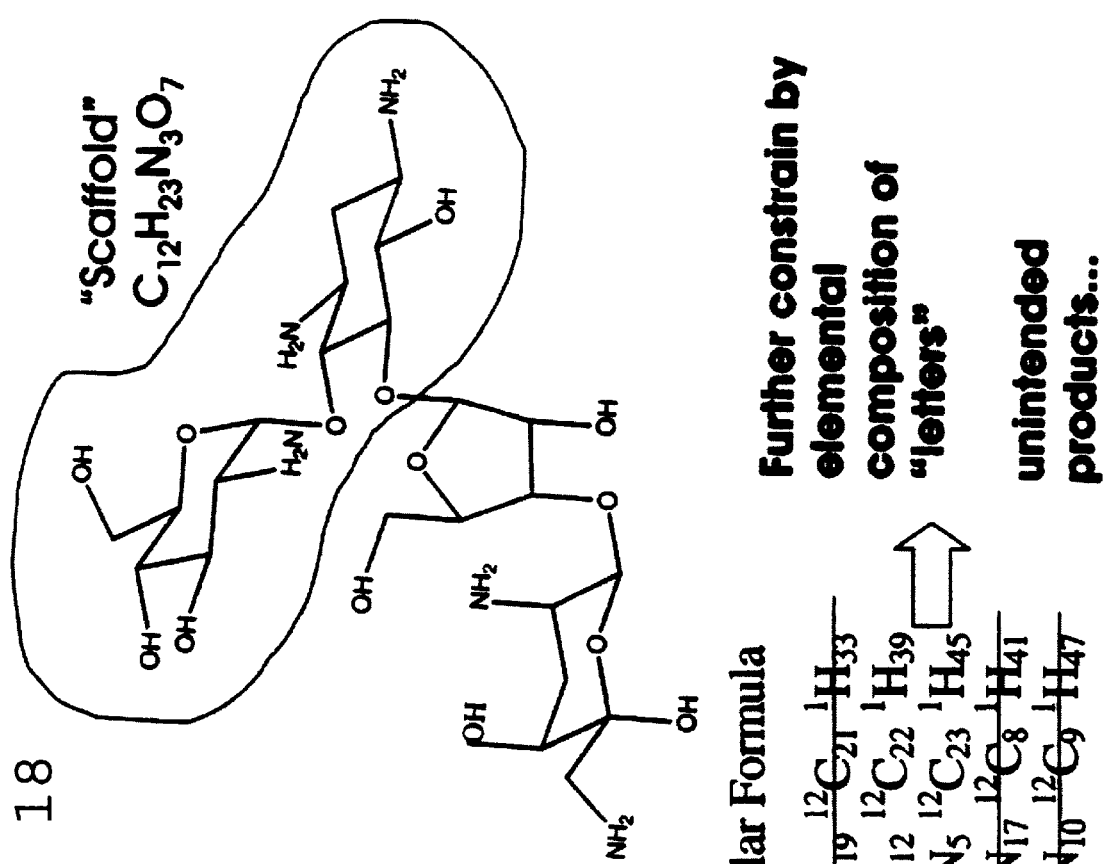
FIG. 18 depicts use of exact mass measurements and elemental constraints to determine the elemental composition of an exemplary "unknown" binding ligand.

Use of exact mass measurements and elemental constraints can be used to determine the elemental composition of an "unknown" binding ligand. General constraints on the type and number of atoms in an unknown molecule, along with a high precision mass measurement, allow determination of a limited list of molecular formulas which are consistent with the measured mass. Referring to FIG. 18, the elemental composition is limited to atoms of C, H, N, and O and further constrained by the elemental composition of a "known" moiety of the molecule. Based on these constraints, the enormous number of atomic combinations which result in a molecular weight of 615.2969±0.0006 are reduced to two possibilities. In addition to unambiguously identifying intended library members, this technique allows one skilled in the art to identify unintended synthetic by-products which bind to the molecular target.

Example 16

Determination of the MASS $K_d$ for 16S-Paromomycin

Figure 19:
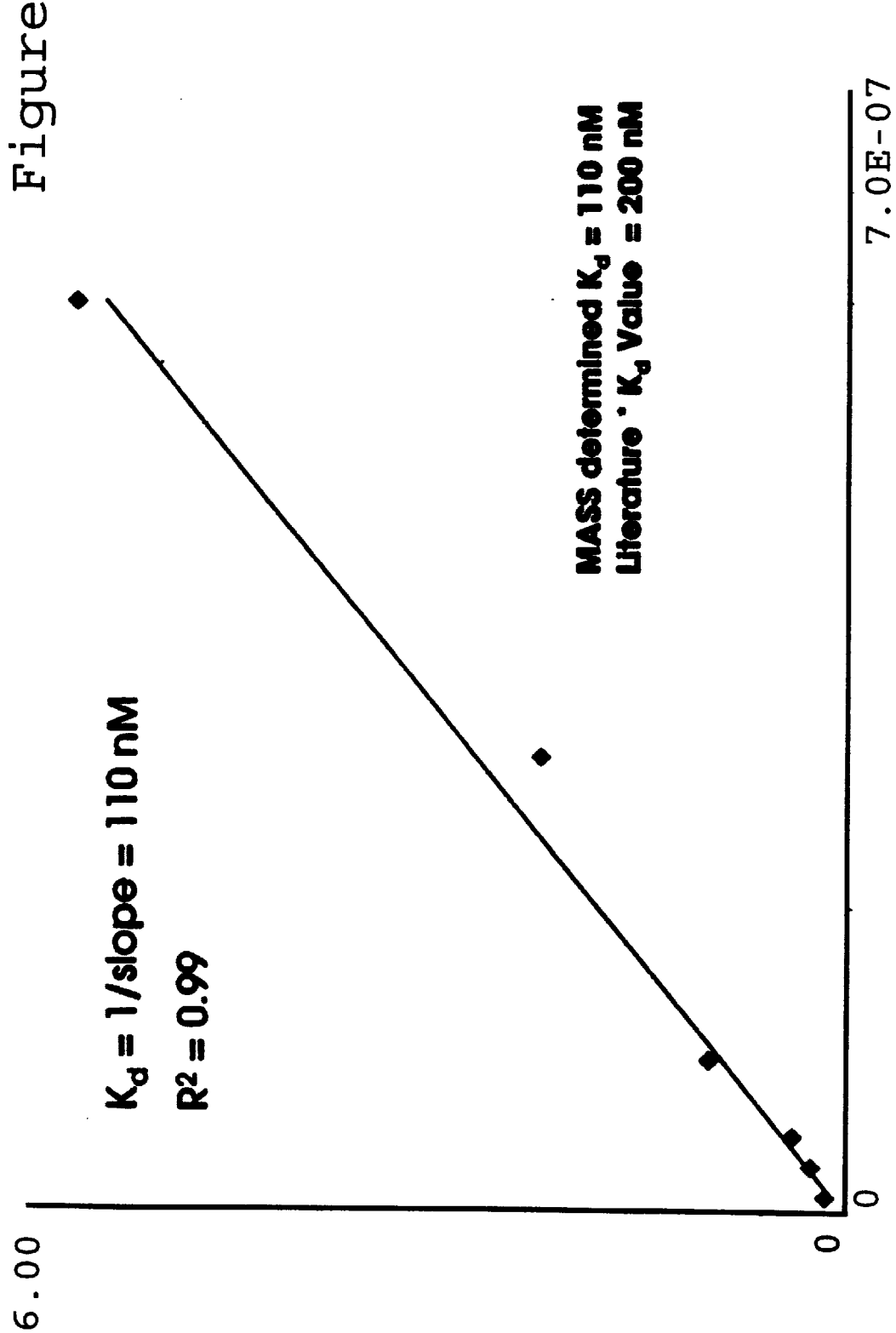
FIG. 19 depicts ESI-MS measurements of a solution containing a fixed concentration of RNA at different concentrations of ligand.

The results of direct determination of solution phase dissociation constants (Kd's) by mass spectrometry is shown in FIG. 19. ESI-MS measurements of a solution containing a fixed concentration of RNA at different concentrations of ligand were obtained. By measuring the ratio of bound:unbound RNA at varying ligand concentrations, the Kd was determined by 1/slope of the "titration curve". The MS derived value of 110 nM is in good agreement with previously reported literature value of 200 nM.

Example 17

Multi-Target Affinity/Specificity Screening

Figure 20:
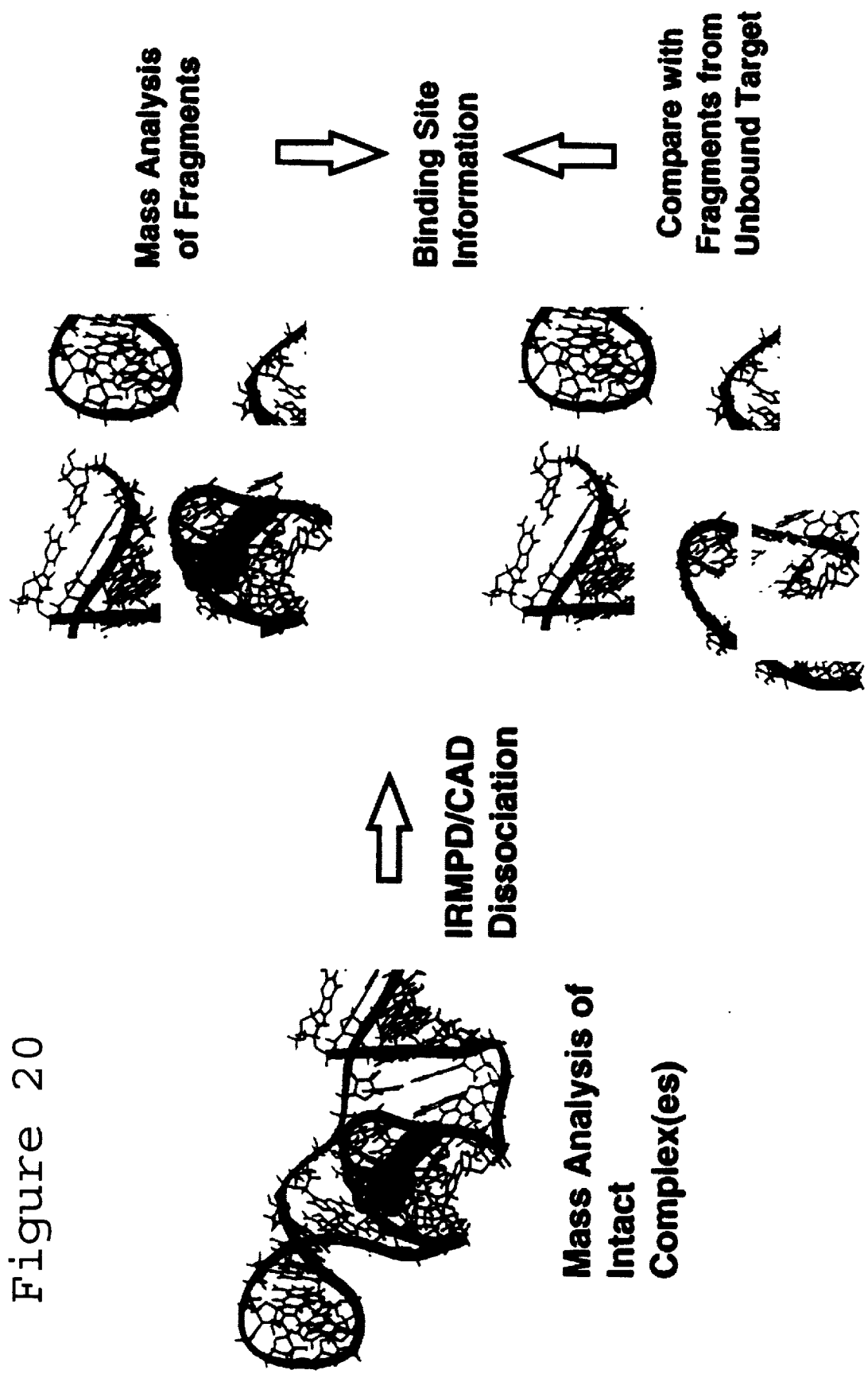
FIG. 20 depicts a preferred schematic representation for the determination of ligand binding site by tandem mass spectrometry.

A schematic representation for the determination of ligand binding site by tandem mass spectrometry is shown in FIG. 20. A solution containing the molecular target or targets is mixed with a library of ligands and given the opportunity to form noncovalent complexes in solution. These noncovalent complexes are mass analyzed. The noncovalent complexes are subsequently dissociated in the gas phase via IRMPD or CAD. A comparison of the fragment ions formed from dissociation of the complex with the fragment ions formed from dissociation of the free RNA reveals the ligand binding site.

Example 18

MASS Analysis of 27-Member Library with 16S A-Site RNA

Figure 21:
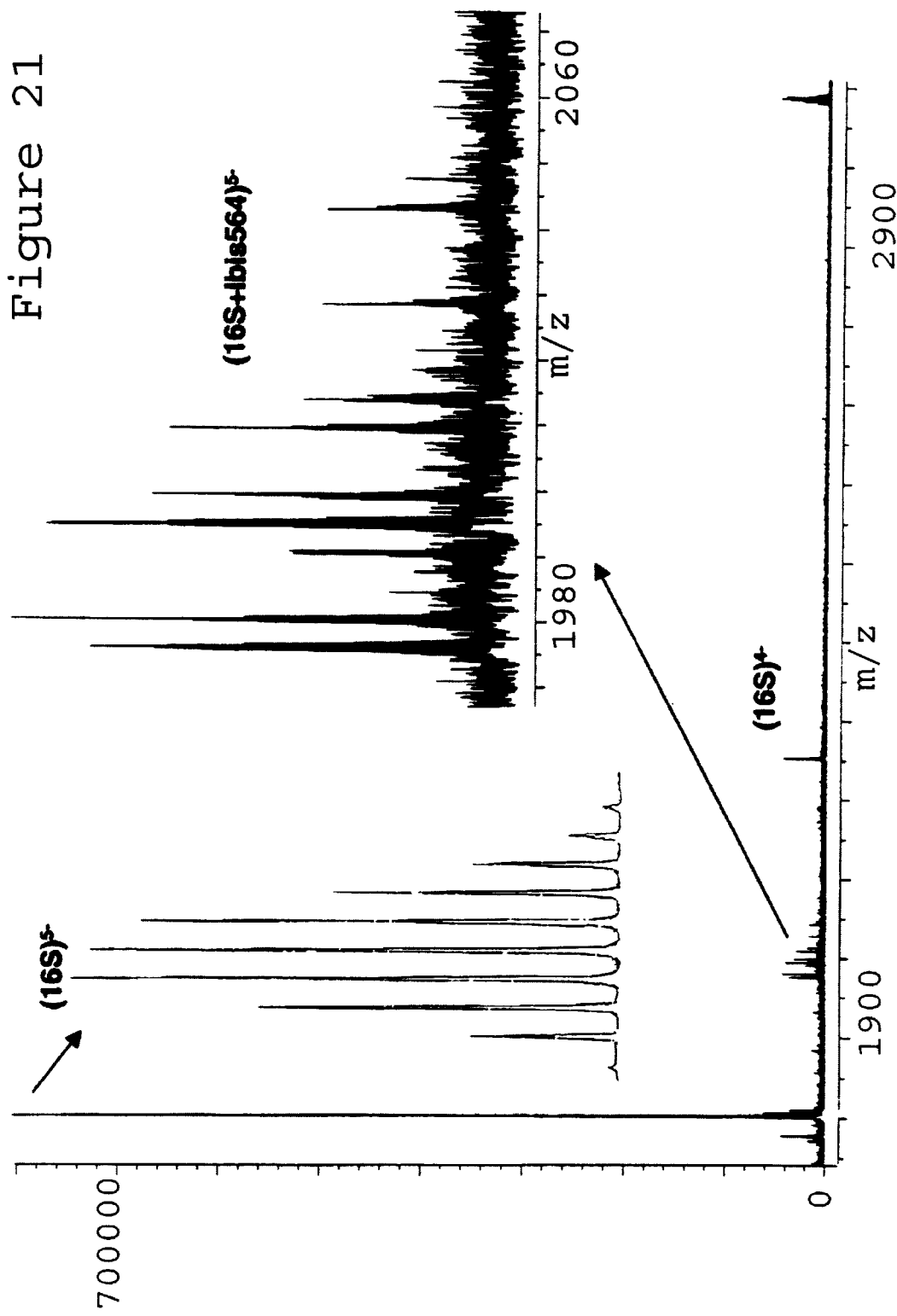
FIG. 21 depicts MASS screening of a 27 member library against a 27-mer RNA construct representing the prokaryotic 16S A-site.

FIG. 21 shows MASS screening of a 27 member library against a 27-mer RNA construct representing the prokaryotic 16S A-site. The inset reveals that a number of compounds formed complexes with the 16S A-site.

Example 19

MASS Protection Assay

Figure 22:
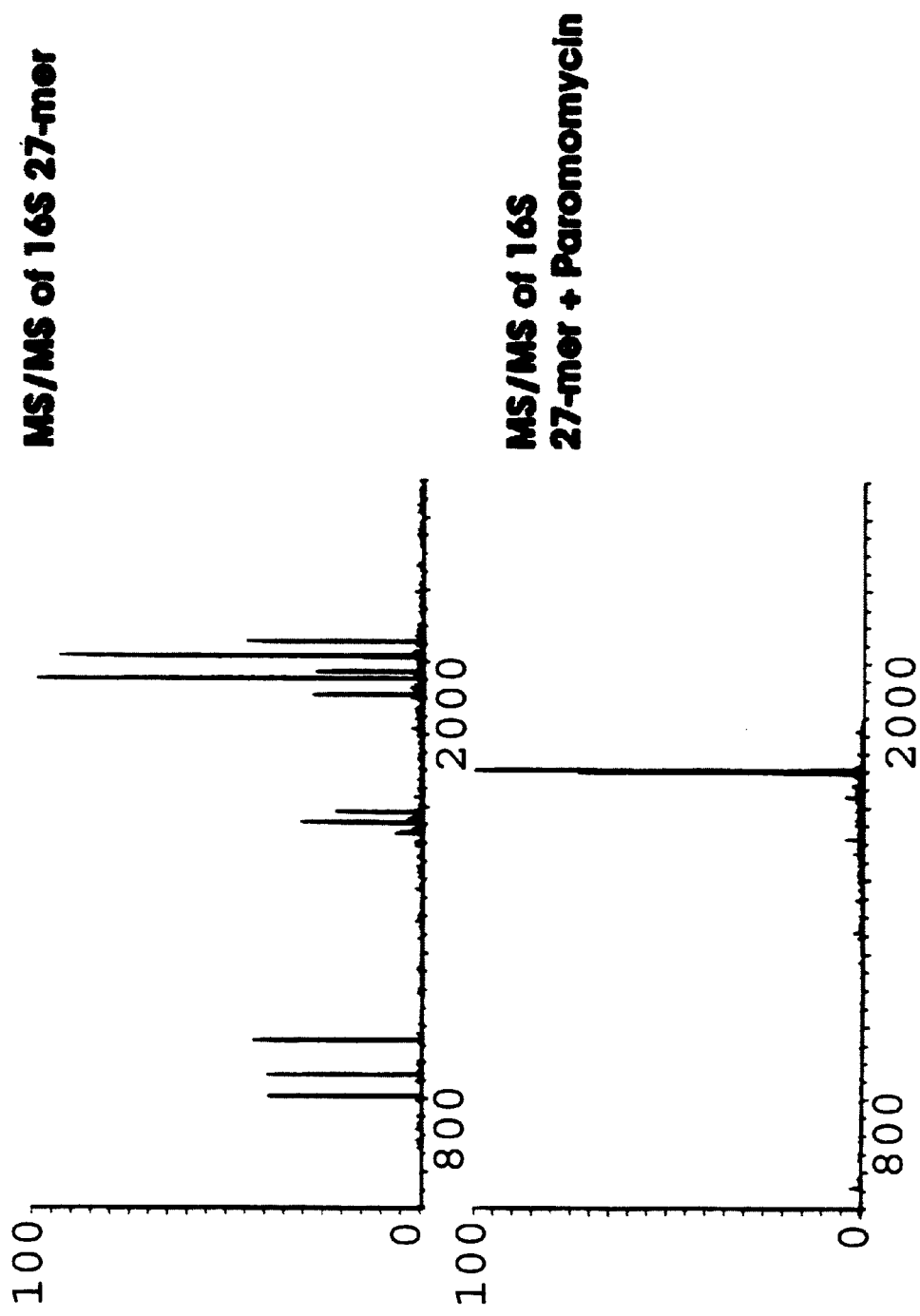
FIG. 22 depicts MS/MS of a 27-mer RNA construct representing the prokaryotic 16S A-site containing deoxyadenosine residues at the paromomycin binding site.

MS/MS of a 27-mer RNA construct representing the prokaryotic 16S A-site containing deoxyadenosine residues at the paromomycin binding site is shown in FIG. 22. The top spectrum was acquired by CAD of the [M-5H]5− ion (m/z 1783.6) from uncomplexed RNA and exhibits significant fragmentation at the deoxyadenosine residues. The bottom spectrum was acquired from by CAD of the [M-5H]5− ion of the 16S-paromomycin complex (m/z 1907.5) under identical activation energy as employed in the top spectrum. No significant fragment ions are observed in the bottom spectrum consistent with protection of the binding site by the ligand.

Figure 23:
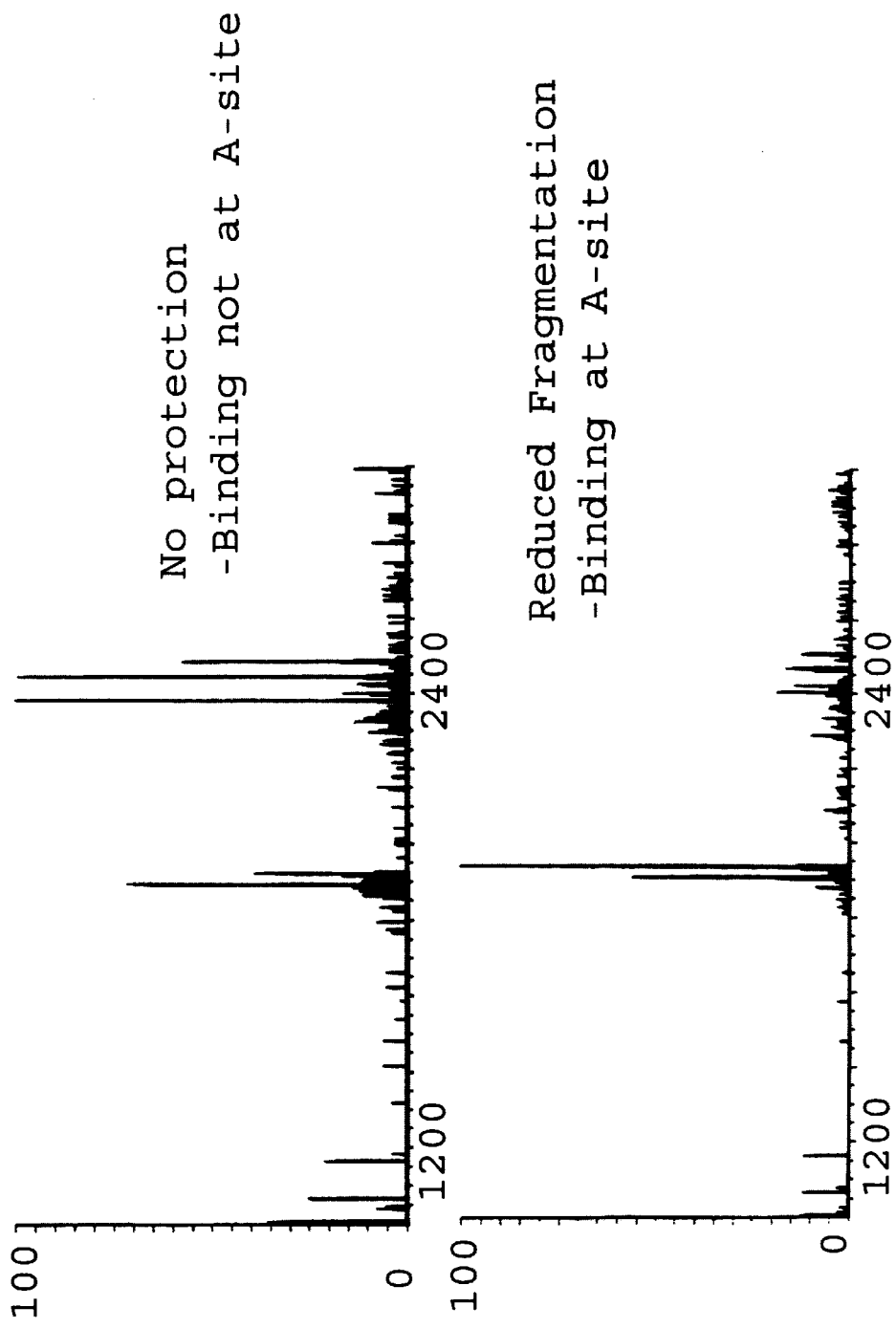
FIG. 23 depicts MS-MS spectra obtained from a mixture of a 27-mer RNA construct representing the prokaryotic 16S A-site containing deoxyadenosine residues at the paromomycin binding and the 216 member combinatorial library.

Two combinatorial libraries containing 216 tetraazacyclophanes dissolved in DMSO were mixed with a buffered solution containing 10 mM 16S RNA (see FIG. 24) such that each library member was present at 100 nM. The resulting mass spectra, shown in FIG. 23 reveal >10 complexes between 16S RNA and library members with the same nominal mass. MS-MS spectra obtained from a mixture of a 27-mer RNA construct representing the prokaryotic 16S A-site containing deoxyadenosine residues at the paromomycin binding and the 216 member combinatorial library. In the top spectrum, ions from the most abundant complex from the first library ([M-5H];5− m/z 1919.0) were isolated and dissociated. Dissociation of this complex generates three fragment ions at m/z 1006.1, 1065.6, and 1162.4 that result from cleavage at each dA residue. More intense signals are observed at m/z 2378.9, 2443.1, and 2483.1. These ions correspond to the w21(3−), a20-B(3−), and a21-B(3−) fragments bound to a library member with a mass of 676.0±0.6 Da. The relative abundances of the fragment ions are similar to the pattern observed for uncomplexed RNA, but the masses, of the ions from the lower stem and tetraloop are shifted by complexation with the ligand. This ligand of fers little protection of the deoxyadenosine residues, and must bind to the lower stem-loop. The library did not inhibit growth of bacteria. In the bottom spectrum, dissociation of the most abundant complex from a mixture of 16S RNA and the second library having m/z 1934.3 with the same collisional energy yields few fragment ions, the predominant signals arising from intact complex and loss of neutral adenine. The reduced level of cleavage and loss of adenine for this complex is consistent with binding of the ligand at the model A site region as does paromomycin. The second library inhibits transcription/translation at 5 mM, and has an MIC of 2–20 mM against E. coli(imp−) and S. pyogenes.

Example 20

Neutral Mass Tag of Eukaryotic and Prokaryotic A-Sites

FIG. 24 shows secondary structures of the 27 base RNA models used in this work corresponding to the 18S (eukaryotic) and 16S (prokaryotic) A-sites. The base sequences differ in seven positions (bold), the net mass difference between the two constructs is only 15.011 Da. Mass tags were covalently added to the 5' terminus of the RNA constructs using tradition phosphoramadite coupling chemistry.

Figure 25:
FIG. 25 depicts ESI-FTICR spectrum of a mixture of 27-base representations of the 16S A-site with (7 $\mu$M) and without (1 $\mu$M) an 18 atom neutral mass tag attached to the 5-terminus in the presence of 500 nM paromomycin.

Methodology to increase the separation between the associated signals in the mass spectra was developed in view of the overlap among signals from RNAs 16S and 18S. RNA targets modified with additional uncharged functional groups conjugated to their 5'-termini were synthesized. Such a synthetic modification is referred to herein as a neutral mass tag. The shift in mass, and concomitant m/z, of a mass-tagged macromolecule moves the family of signals produced by the tagged RNA into a resolved region of the mass spectrum. ESI-FTICR spectrum of a mixture of 27-base representations of the 16S A-site with (7 mM) and without (1 mM) an 18 atom neutral mass tag attached to the 5-terminus in the presence of 500 nM paromomycin is shown in FIG. 25. The ratio between unbound RNA and the RNA-paromomycin complex was equivalent for the 16S and 16S+tag RNA targets demonstrating that the neutral mass tag does not have an appreciable effect on RNA-ligand binding.

Example 21

Simultaneous Screening of 16S A-Site and 18S A-Site Model RNAs Against Aminoglycoside Mixture Paromomycin, lividomycin (MW=761.354 Da), sisomicin (MW=447.269 Da), tobramycin (MW=467.2591 Da), and bekanamycin (MW=483.254 Da) were obtained from Sigma (St. Louis, Mo.) and ICN (Costa Mesa, Calif.) and were dissolved to generate 10 mM stock solutions. 2' methoxy analogs of RNA constructs representing the prokaryotic (16S) rRNA and eukaryotic (18S) rRNA A-site (FIG. 24) were synthesized in house and precipitated twice from 1 M ammonium acetate following deprotection with ammonia PH 8.5). The mass-tagged constructs contained an 18-atom mass tag ($C_{12}H_{25}O_9$) attached to the 5'-terminus of the RNA oligomer through a phosphodiester linkage.

All mass spectrometry experiments were performed using an Apex II 70e electrospray ionization Fourier transform ion cyclotron resonance mass spectrometer (Brukcer Daltonics, Billerica) employing an actively shielded 7 tesla superconducting magnet. RNA solutions were prepared in 50 mM $NH_4OAc$ (pH 7), mixed 1:1 v:v with isopropanol to aid desolvation, and infused at a rate of 1.5 mL/min using a syringe pump. Ions were formed in a modified electrospray source (Analytica, Branford) employing an of f axis, grounded electrospray probe positioned ca. 1.5 cm from the metalized terminus of the glass desolvation capillary biased at 5000 V. A counter-current flow of dry oxygen gas heated to 225° C. was employed to assist in the desolvation process. Ions were accumulated in an external ion reservoir comprised of an RF-only hexapole, a skimmer cone, and an auxiliary electrode for 1000 ms prior to transfer into the trapped ion cell for mass analysis. Each spectrum was the result of the coaddition of 16 transients comprised of 256 datapoints acquired over a 90,909 kHz bandwidth resulting in a 700 ms detection interval. All aspects of pulse sequence control, data acquisition, and post acquisition processing were performed using a Bruker Daltonics datastation running XMASS version 4.0 on a Silicon Graphics (San Jose, Calif.) R5000 computer.

Mass spectrometry experiments were performed in order to detect complex formation between a library containing five aminoglycosides (Sisomicin (Sis), Tobramycin (Tob), Bekanomycin (Bek), Paromomycin (PM), and Livodomycin (LV)) and two RNA targets simultaneously. Signals from the $(M-5H^+)^{5-}$ charge states of free 16S and 18S RNAs are detected at m/z 1801.515 and 1868.338, respectively. As shown in FIG. 26, the mass spectrometric assay reproduces the known solution binding properties of aminoglycosides to the 16S A site model and an 18S A site model with a neutral mass linker. Consistent with the higher binding affinity of theses aminoglycosides for the 16S A-site relative to the 18S A-site, aminoglycoside complexes are observed only with the 16S rRNA target. Note the absence of 18S-paromomycin and 18S-lividomycin complexes, which would be observed at the m/z's indicated by the arrows. The inset demonstrates the isotopic resolution of the complexes. Using multiple isotope peaks of the $(M-5H^+)^{5-}$ and $(M-4H^+)^{4-}$ charge states of the free RNA as internal mass standards, the average mass measurement error of the complexes is 2.1 ppm. High affinity complexes were detected between the 16S A site 27mer RNA and paromomyc in and lividomycin, respectively. Weaker complexes were observed with sisomycin, tobramycin and bekamycin. No complexes were observed between any of the aminoglycosides and the 18S A site model. Thus, this result validates the mass spectrometric assay for identifying compounds that will bind specifically to the target RNAs. No other type of high throughput assay can provide information on the specificity of binding for a compound to two RNA targets simultaneously. The binding of lividomycin to the 16S A site had been inferred from previous biochemical experiments. The mass spectrometer has been used herein to measure a $K_D$ of 28 nM for lividomycin and 110 nM for paromomycin to the 16S A site 27 mer. The solution $K_D$ for paromomycin has been estimated to be between 180 nM and 300 nM.

Example 22

Targeted Site-Specific Gas-Phase Cleavage of Oligoribonucleotides—Application in Mass Spectrometry-Based Identification of Ligand Binding Sites Fragmentation of oligonucleotides is a complex process, but appears related to the relative strengths of the glycosidic bonds. This observation is exploited by incorporating deoxy-nucleotides selectively into a chimeric 2'-O-methylribonucleotide model of the bacterial rRNA A site region. Miyaguchi, et al., *Nucl. Acids Res.*, 1996, 24, 3700–3706; Fourmy, et al., *Science*, 1996, 274, 1367–1371; and Fourmy, et al, *J. Mol. Biol.*, 1998, 277, 333–345. During CAD, fragmentation is directed to the more labile deoxy-nucleotide sites. The resulting CAD mass spectrum contains a small subset of readily assigned complementary fragment ions. Binding of ligands near the deoxyadenosine residues inhibits the CAD process, while complexation at remote sites does not affect dissociation and merely shifts the masses of specific fragment ions. These methods are used to identify compounds from a combinatorial library that preferentially bind to the RNA model of the A site region.

Figure 27:
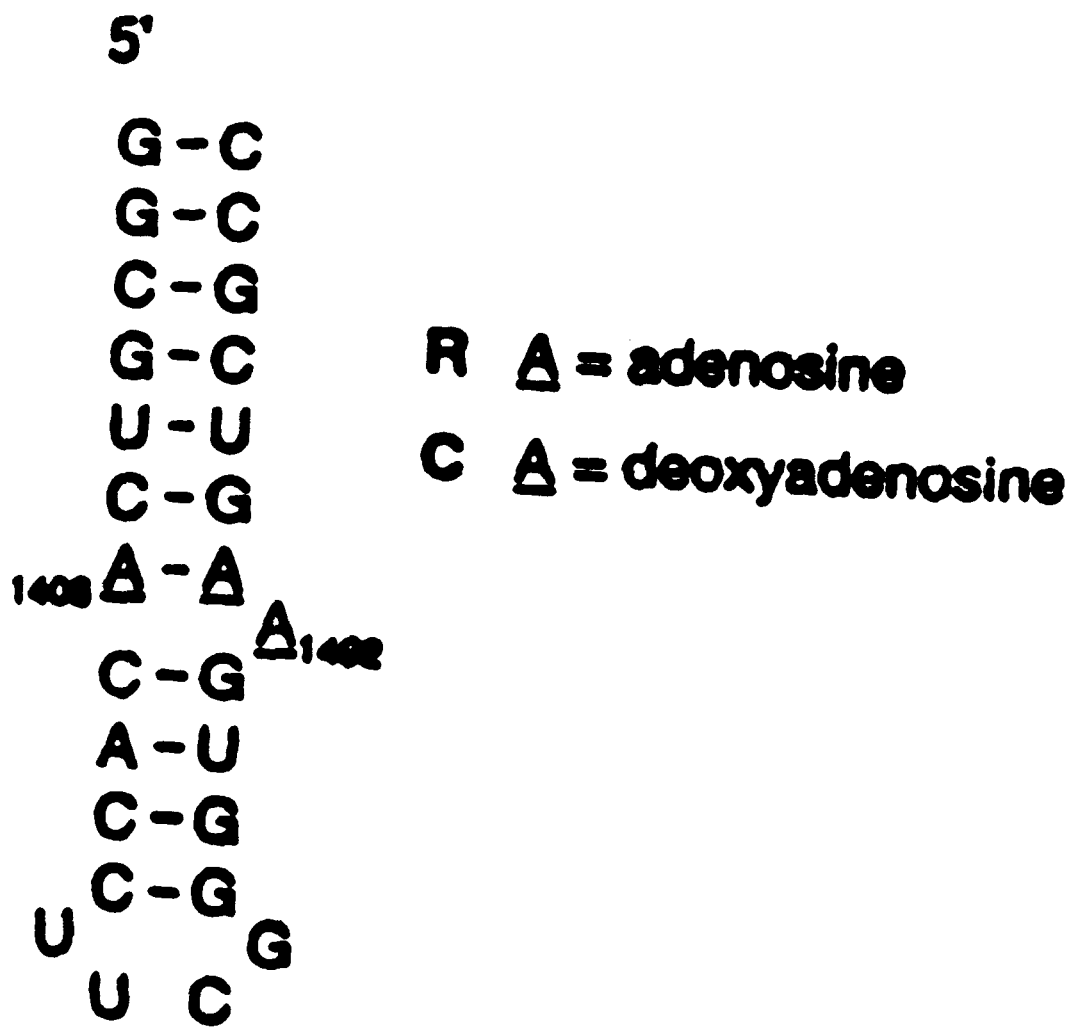
FIG. 27 depicts sequences and structures for oligonucleotides R and C.

The 27-mer model of a segment of the bacterial A site region has been prepared as a full ribonucleotide (see FIG. 27, compound R), and as a chimeric 2'-O-methylribonucleotide containing three deoxyadenosine residues (see FIG. 27, compound C). RNAs R and C have been prepared using conventional phosphoramidite chemistry on solid support. Phosphoramidites were purchased from Glen Research and used as 0.1 M solutions in acetonitrile. RNA R was prepared following the procedure given in Wincott, et al, *Nucl. Acids Res.*, 1995, 23, 2677–2684, the disclosure of which is incorporated herein by reference in its entirety. RNA C was prepared using standard coupling cycles, deprotected, and precipitated from 10 M $NH_4OAc$. The aminoglycoside paromomycin binds to both R and C with kD values of 0.25 and 0.45 micromolar, respectively. The reported kD values are around 0.2 µM. Recht, et al., *J. Mol. Biol.*, 1996, 262, 421–436, Wong, et al., *Chem. Biol.*, 1998, 5, 397–406, and Wang, et al., *Biochemistry*, 1997, 36, 768–779. Paromomycin has been shown previously to bind in the major groove of the 27 mer model RNA and induce a conformational change, with contacts to A1408, G1494, and G1491. Miyaguchi, et al, *Nucl. Acids Res.*, 1996, 24, 3700–3706; Fourmy, et al., *Science*, 1996, 274, 1367–1371; and Fourmy, et al., *J. Mol. Biol*, 1998, 277, 333–345.

Figure 28:
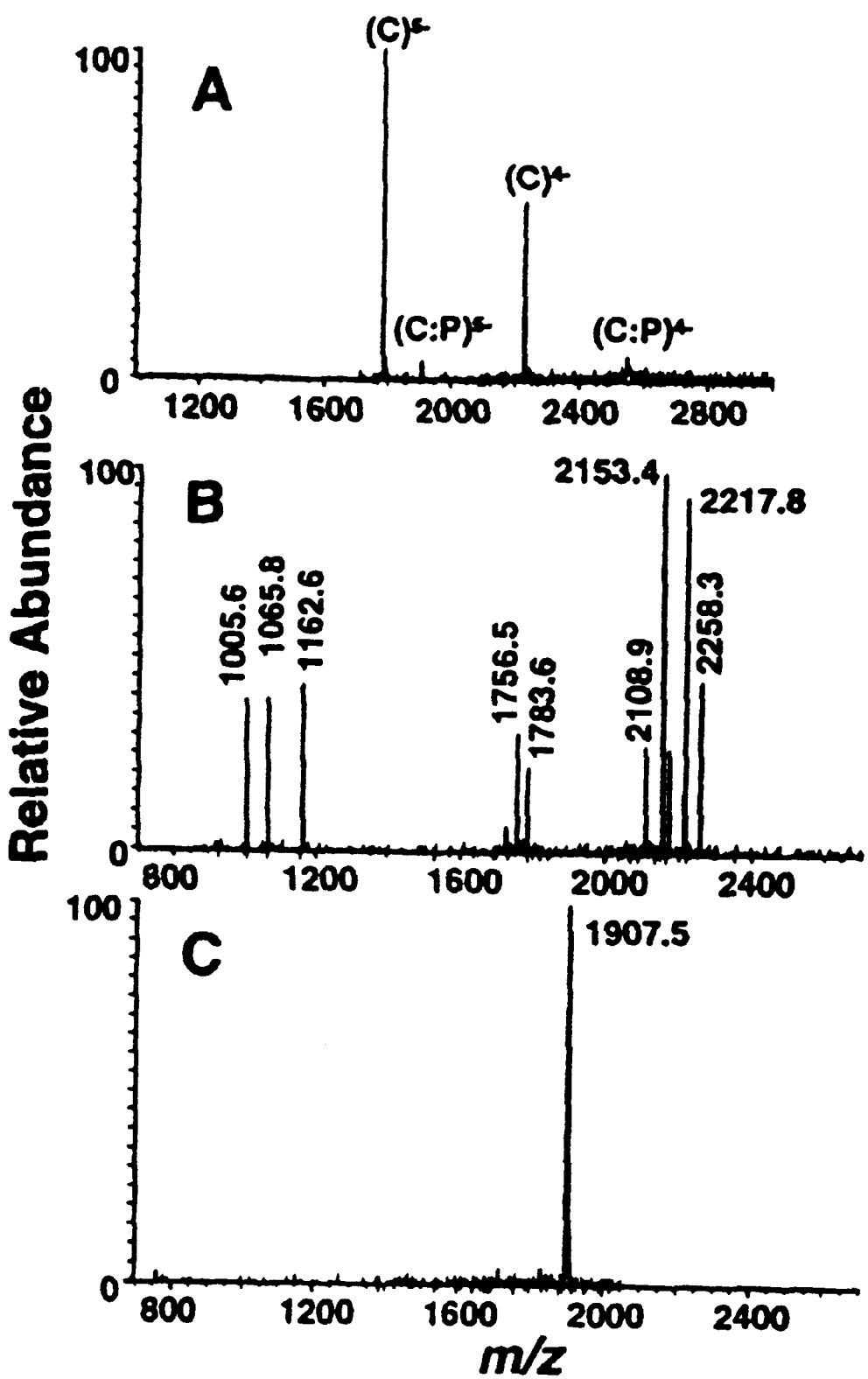
FIG. 28A depicts mass spectrum obtained from a mixture of 5 $\mu$M C and 125 nM paromomycin.
FIG. 28B depicts MS-MS spectrum obtained following isolation of $[M-5H]^{5-}$ ions (m/z 1783.6) from uncomplexed C.
FIG. 28C depicts MS-MS spectrum obtained following isolation of $[M-5H]^{5-}$ ions (m/z 1907.5) from C complexed with paromomycin.

The mass spectrum obtained from a 5 µM solution of C mixed with 125 nM paromomycin (FIG. 28A) contains [M-5H]5- ions from free C at m/z 1783.6 and the [M-5H]5- ions of the paromomycin-C complex at m/z 1907.3. Mass spectrometry experiments have been performed on an LCQ quadrupole ion trap mass spectrometer (Finnigan; San Jose, Calif.) operating in the negative ionization mode. RNA and ligand were dissolved in a 150 mM ammonium acetate buffer at pH 7.0 with isopropyl alcohol added (1:1 v:v) to assist the desolvation process. Parent ions have been isolated with a 1.5 m/z window, and the AC voltage applied to the end caps was increased until about 70% of the parent ion dissociates. The electrospray needle voltage was adjusted to −3.5 kV, and spray was stabilized with a gas pressure of 50 psi (60:40 N2:02). The capillary interface was heated to a temperature of 180° C. The He gas pressure in the ion trap was 1 mTorr. In MS-MS experiments, ions within a 1.5 Da window having the desired m/z were selected via resonance ejection and stored with q) 0.2. The excitation RF voltage was applied to the end caps for 30 ms and increased manually to 1.1 Vpp to minimize the intensity of the parent ion and to generate the highest abundance of fragment ions. A total of 128 scans were summed over m/z 700–2700 following trapping for 100 ms. Signals from the [M-4H]4− ions of C and the complex are detected at m/z 2229.8 and 2384.4, respectively. No signals are observed from more highly charged ions as observed for samples denatured with tripropylarnine. In analogy with studies of native and denatured proteins, this is consistent with a more compact structure for C and the paromomycin complex. The CAD mass spectrum obtained from the [M-5H]5− ion of C is presented in FIG. 28B. Fragment ions are detected at m/z 1005.6 (w6)2−, 1065.8 (a7-B)2−, 1162.6 (w7)2−, 1756.5 (M-Ad)5−, 2108.9 (w21-Ad)3−, 2153.4 (a20-B)3−, 22 and 2258.3 (a21-B)3−. McLuckey, et al., *J. Am. Soc. Mass Spectrum.*, 1992, 3,60–70 and McLuckey, et al., *J. Am. Chem. Soc.*, 1993, 115, 12085–12095. These fragment ions all result from loss of adenine from the three deoxyadenosine nucleotides, followed by cleavage of the 3'-C—O sugar bonds. The CAD mass spectrum for the [M-5H]5− ion of the complex between C and paromomycin obtained with the same activation energy is shown in FIG. 28C. No fragment ions are detected from strand cleavage at the deoxyadenosine sites using identical dissociation conditions of FIG. 28B. The change in fragmentation pattern observed upon binding of paromomycin is consistent with a change in the local charge distribution, conformation, or mobility of A1492, A1493, and A1408 that precludes collisional activation and dissociation of the nucleotide.

Figure 29:
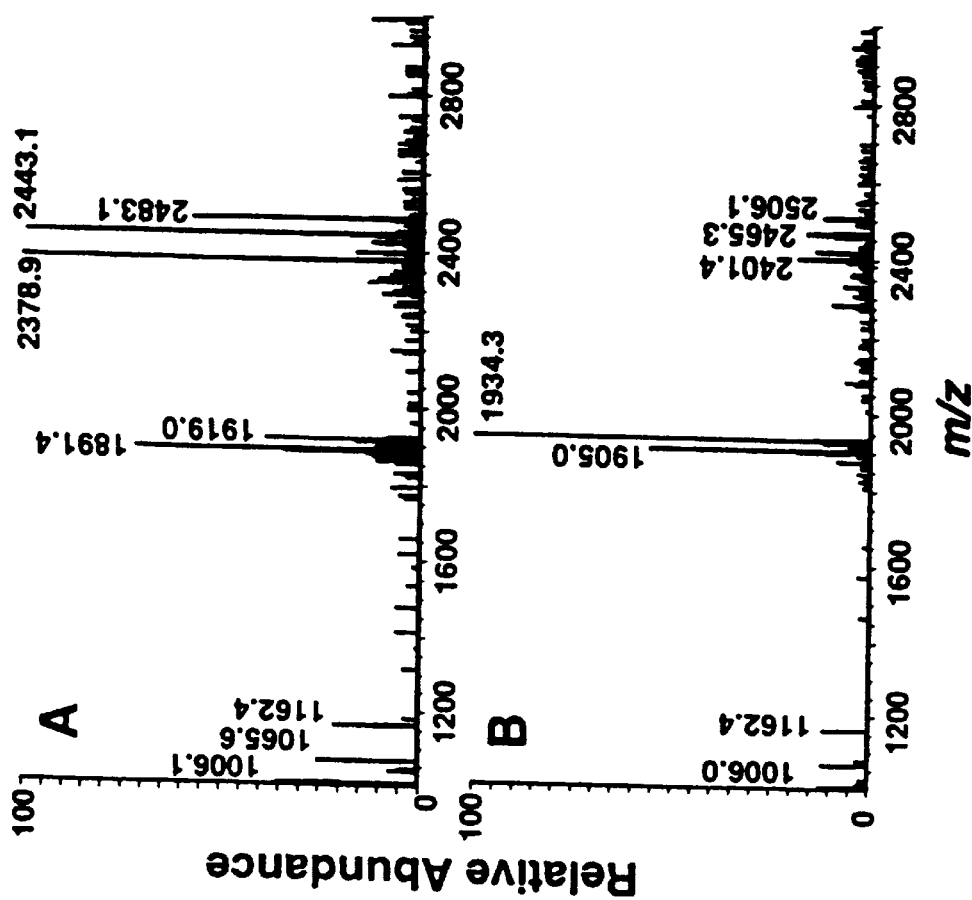
FIG. 29A depicts MS-MS spectrum obtained from a mixture of 10 $\mu$M C and a 216 member combinatorial library following isolation of $[M-5H]^{5-}$ ions (m/z 1919.0) from C complexed with ligands of mass 676.0±0.6.
FIG. 29B depicts MS-MS spectrum obtained from a mixture of 10 $\mu$M C and a 216 member combinatorial library following isolation of $[M-5H]^{5-}$ ions (m/z 1934.3) from C complexed with ligands of mass 753.5±0.6.

Two combinatorial libraries containing 216 tetraazacyclophanes dissolved in DMSO ere mixed with a buffered solution containing 10 μM C such that each library member is present at 100 nM. The resulting mass spectra reveal >10 complexes between C and library members with the same nominal mass. Ions from the most abundant complex from the first library ([M-5H]$_5^{5-}$ m/z 1919.0) were isolated and dissociated. As shown in FIG. 29A, dissociation of this complex generates three fragment ions at m/z 1006.1, 1065.6, and 1162.4 that result from cleavage at each dA residue. More intense signals are observed at m/z 2378.9, 2443,1, and 2483.1. These ions correspond to the $w_{21}^{(3-)}$, $a_{20}$-B$^{(3-)}$, and $a_{21}$-B$^{(3-)}$ fragments bound to a library member with a mass of 676.0=0.6 Da. The relative abundances of the fragment ions are similar to the pattern observed for uncomplexed C, but the masses of the ions from the lower stem and tetraloop are shifted by complexation with the ligand. This ligand of fers little protection of the deoxyadenosine residues, and must bind to the lower stem-loop. The libraries have been synthesized from a mixture of charged and aromatic functional groups, and are described as libraries 25 and 23 in: An, et al., *Bioorg. Med. Chem. Lett.*, 1998, in press. Dissociation of the most abundant complex from a mixture of C and the second library having m/z 1934.3 with the same collisional energy (FIG. 29B) yields few fragment ions, the predominant signals arising from intact complex and loss of neutral adenine. The mass of the ligand (753.5 Da) is consistent with six possible compounds in the library having two combinations of functional groups. The reduced level of cleavage and loss of adenine from this complex is consistent with binding of the ligand at the model A site region as does paromomycin. The second library inhibits transcription/translation at 5 μm, and has an MIC of 2–20 μM against *E. coli* (imp-) and *S. pyogenes*.

Mass spectrometry-based assays provide many advantages for identification of complexes between RNA and small molecules. All constituents in the assay mixture carry an intrinsic mass label, and no additional modifications with radioactive or fluorescent tags are required to detect the formation of complexes. The chemical composition of the ligand can be ascertained from the measured molecular mass of the complex, allowing rapid deconvolution of libraries to identify leads against an RNA target. Incorporation of deoxynucleotides into a chimeric oligoribonucleotide generates a series of labile sites where collisionally-activated dissociation is favored. Binding of ligands at the labile sites affords protection from CAD observed in MS-MS experiments. This mass spectrometry-based protection methods of the invention can be used to establish the binding sites for small molecule ligands without the need for additional chemical reagents or radiobabeling of the RNA. The methodology can also be used in DNA sequencing and identification of genomic defects.

In accordance with preferred embodiments of the present invention, enhanced accuracy of determination of binding between target biomolecules and putative ligands is desired. It has been found that certain mass spectrometric techniques can give rise to such enhancement. As will be appreciated, the target biomolecule will always be present in excess in samples to be spectroscopically analyzed. The exact composition of such target will, similarly, be known. Accordingly, the isotopic abundances of the parent (and other) ions deriving from the target will be known to precision.

In accordance with preferred embodiments, mass spectrometric data is collected from a sample comprising target biomolecule (or biomolecules) which has been contacted with one or more, preferably a mixture of putative or trial ligands. Such a mixture of compounds may be quite complex as discussed elsewhere herein. The resulting mass spectrum will be complex as well, however, the signals representative of the target biomolecule(s) will be easily identified. It is preferred that the isotopic peaks for the target molecule be identified and used to internally calibrate the mass spectrometric data thus collected since the M/e for such peaks is known with precision. As a result, it becomes possible to determine the exact mass shift (with respect to the target signal) of peaks which represent complexes between the target and ligands bound to it. Given the exact mass shifts, the exact molecular weights of said ligands may be determined. It is preferred that the exact molecular weights (usually to several decimal points of accuracy) be used to determine the identity of the ligands which have actually bound to the target.

In accordance with other preferred embodiments, the information collected can be placed into a relational or other database, from which firther information concerning ligand binding to the target biomolecule can be extracted. This is especially true when the binding affinities of the compounds found to bind to the target are determined and included in the database. Compounds having relatively high binding affinities can be selected based upon such information contained in the database.

It is preferred that such data collection and database manipulation be achieved through a general purpose digital computer. An exemplary software program has been created and used to identify the small molecules bound to an RNA target, calculate the binding constant, and write the results to a relational database. The program uses as input a file that lists the elemental formulas of the RNA and the small molecules which are present in the mixture under study, and their concentrations in the solution. The program first calculates the expected isotopic peak distribution for the most abundant charge state of each possible complex, then opens the raw FTMS results file. The program performs a fast Fourier transform of the raw data, calibrates the mass axis, and integrates the signals in the resulting spectrum such as the exemplary spectrum shown in FIG. 30. The peaks in the spectrum are preferably identified via centroiding as shown in FIG. 31, are integrated, and preferably stored in a database. An exemplary data file is shown in FIG. 32). The expected and observed peaks are correlated, and the integrals converted into binding constants based on the intensity of an internal standard. The compound identity and binding constant data are written to a relational database. This approach allows large amounts of data that are generated by the *S mass spectrometer to be analyzed without human intervention, which results in a significant savings in time.

Figure 30:
FIG. 30 depicts electrospray ionization Fourier transform ion cyclotron resonance mass spectrometry of a target/putative ligand mixture.
Figure 31:
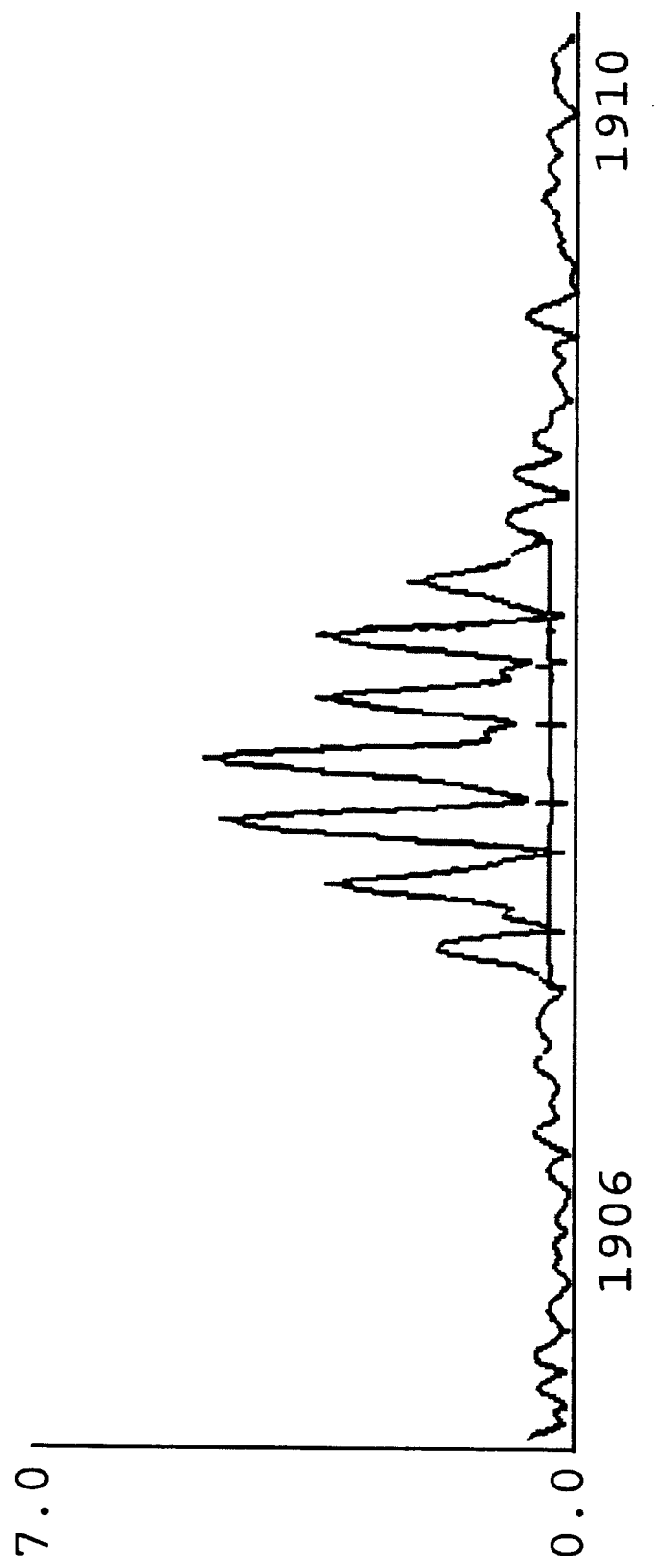
FIG. 31 shows isotope clusters from the spectrum of FIG. 30.

FIG. 30 depicts electrospray ionization Fourier transform ion cyclotron resonance mass spectrometry of a solution which is 5 mM in 16S RNA (Ibis 16628) and 500 nM in the ligand Ibis10019. The raw time-domain data set is automatically apodized and zerofilled twice prior to Fourier transformation. The spectrum is automatically post-calibrated using multiple isotope peaks of the $(M-5H^+)^{5-}$ and $(M-4H^+)^{4-}$ charge states of the free RNA as internal mass standards and measuring the m/z difference between the free and bound RNA. The isotope distribution of the free RNA is calculated a priori and the measured distribution is fit to the calculated distribution to ensure that m/z differences are measured between homoisotopic species (e.g. monoisotopic peaks or isotope peaks containing 4 $^{13}C$ atoms).

Figure 33:
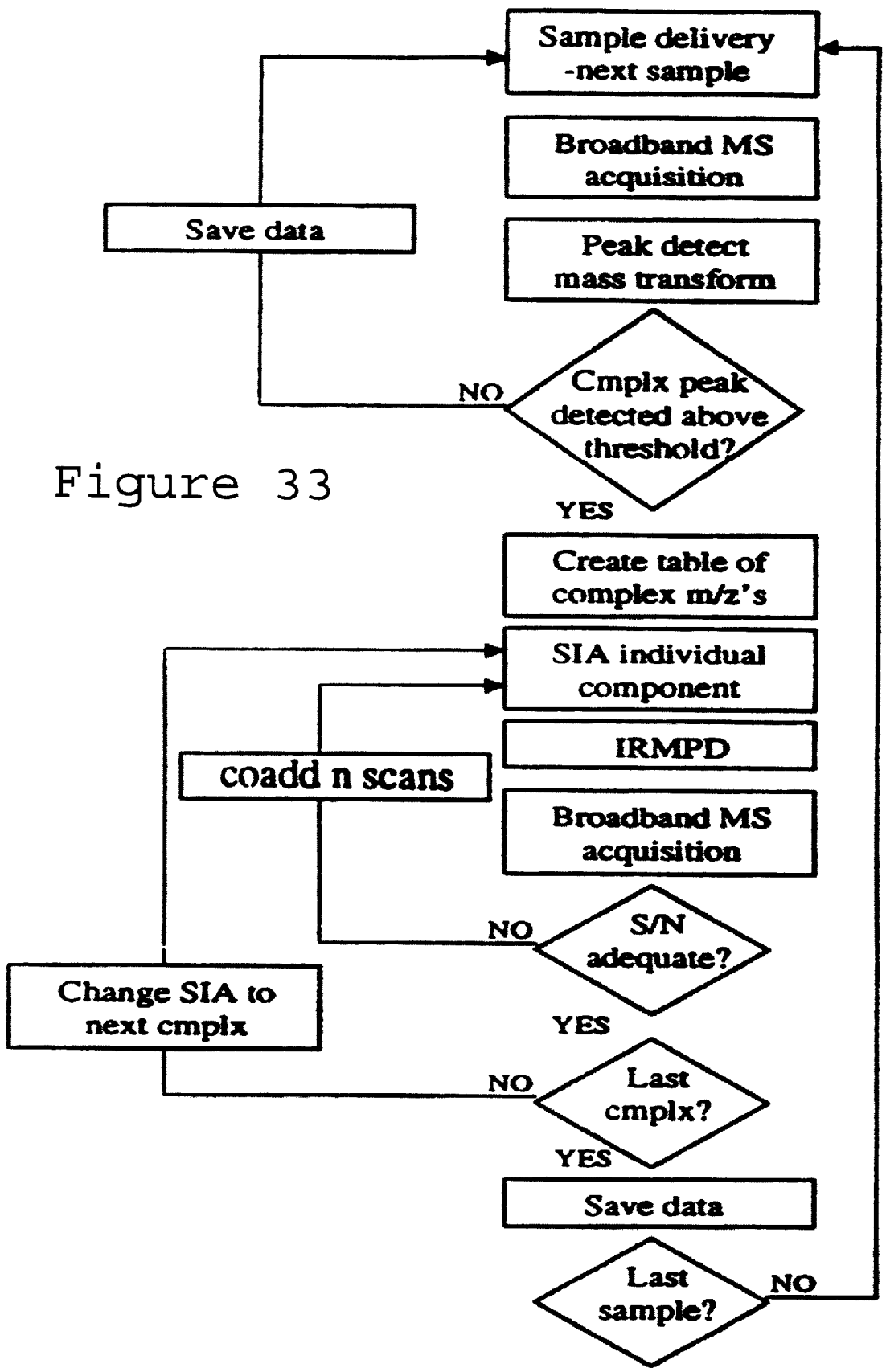
FIG. 33 shows an exemplary flow chart for a computer program for effecting certain methods in accordance with the invention.

FIG. 31 shows isotope clusters observed in the m/z range where RNA-ligand complexes are expected are further analyzed by peak centroiding and integration. FIG. 32 depicts data tabulated and stored in a relational database. Peaks which correspond to complexes between the RNA target and ligands are assigned and recorded in the database. If an internal affinity standard is employed, a relative Kd is automatically calculated from the relative abundance of the standard complex and the unknown complex and recorded in the database. FIG. 33 depicts a flow chart for one computer program for effectuating certain aspects of the present invention.

When computer controlled collection of the foregoing information is provided and computer control of relational databases is employed, the present invention is capable of very high throughput analysis of mass spectrometric binding information. Such control facilitates the identification of ligands having high binding affinities for the target biomolecules. Thus, automation permits the automatic calculation of the mass of the binding ligand or ligands, especially when the mass of the target is used for internal calibration purposes. From the precise mass of the binding ligands, their identity may be determined in an automated way. The dissociation constant for the ligand-target interaction may also be ascertained using either known Kd and abundance of a reference complex or by titration with multiple measurements at different target/ligand ratios. Further, tandem mass spectrometric analyses may be performed in an automated fashion such that the site of the small molecule, ligand, interaction with the target can be ascertained through fragmentation analysis. Computer input and output from the relational database is, of course, preferred.

What is claimed is:

1. A method for determining the relative binding affinity of a binding agent for a biomolecular target comprising:
    (a) providing a first complex of said biomolecular target and said binding agent;
    (b) ionizing said first complex in a mass spectrometer to provide one or more ions of said first complex;

(c) collecting mass spectral data from the ionization of step (b) and identifying therefrom the ion abundance of said first complex;

(d) providing a second complex of said biomolecular target and a standard binding compound which binds to said target;

(e) ionizing said second complex in a mass spectrometer to provide one or more ions of said second complex;

(f) collecting mass spectral data from the ionization of step (e) and identifying therefrom the ion abundance of said second complex, wherein the relative the ion abundances of said first and second complexes affords a measure of said relative binding affinity.

2. The method of claim 1 wherein said ion abundances of said first and second complexes are compared to identify said relative binding affinity.

3. The method of claim 1 wherein said biomolecular target is a nucleic acid.

4. The method of claim 3 wherein said nucleic acid is RNA.

5. The method of claim 4 wherein said RNA corresponds to a 16S rRNA A-site.

6. The method of claim 4 wherein said RNA includes one or more deoxynucleotide subunits at preselected locations thereof.

7. The method of claim 1 wherein said biomolecular target is a peptide, protein, antibody, carbohydrate, oligosaccharide or glycopeptide.

8. The method of claim 1 wherein said biomolecular target is a nucleic acid moiety.

9. The method of claim 1 wherein said ionizing is achieved through electrospray ionization, atmospheric pressure ionization or matrix-assisted laser desorption ionization.

10. A method for identifying in a combinatorial mixture compounds which bind to a biomolecular target, wherein the method comprises:

(a) providing mass spectral data on the ion abundance for said biomolecular target;

(b) providing a first complex of said biomolecular target and a standard binding compound which binds to said target;

(c) combining with said first complex a combinatorial mixture of compounds;

(d) ionizing in a mass spectrometer said combination from step c to provide a plurality of ions for said combination;

(e) collecting from the ionization of step (d) mass spectral data on the ion abundance of said first complex, wherein said ion abundances in steps (a) and (e) affords information for effecting said determination.

11. The method of claim 10 wherein mass differences in the mass spectral data from steps (a) and (e) are identified for determining the mass of compounds from the combinatorial mixture which preferentially bind with said bimolecular target.

12. The method of claim 10 wherein said biomolecular target is a nucleic acid.

13. The method of claim 12 wherein said nucleic acid is RNA.

14. The method of claim 13 wherein said RNA corresponds to a 16S rRNA A-site.

15. The method of claim 13 wherein said RNA includes one or more deoxynucleotide subunits at preselected locations thereof.

16. The method of claim 15 wherein said biomolecular target is a peptide, protein, antibody, carbohydrate, oligosaccharide or glycopeptide.

17. A method for determining the relative binding affinity of compounds in a combinatorial mixture for a biomolecular target comprising:

(a) providing a first complex of said biomolecular target and a standard binding compound which binds to said target;

(b) combining with said first complex a combinatorial mixture of compounds, wherein one or more of said compounds from said combinatorial mixture preferentially binds with said biomolecular target to provide secondary complexes;

(c) ionizing said combination of step (b) in a mass spectrometer to provide a plurality of ions;

(d) collecting mass spectral data from the ionization of step c and identifying therein ion abundances for said first and said secondary complexes, wherein the ion abundances of said first and additional complexes affords information for identifying said relative binding affinity.

18. The method of claim 17 wherein said ion abundances of said first and additional complexes are compared to identify said relative binding affinity.

19. The method of claim 17 wherein said biomolecular target is a nucleic acid.

20. A method for screening a plurality of biomolecular targets against a binding agent comprising:

(a) providing n different biomolecular targets, wherein n is an integer greater than or equal to 2;

(b) modifying n! 1 of said biomolecular targets with mass modifying tags, wherein the mass to charge ratio of ions of about the same charge of said modified biomolecular targets are substantially distinguishable by mass spectrometry;

(c) combining said modified biomolecular targets with a binding agent;

(d) ionizing said combination from step c in a mass spectrometer to provide a plurality of ions; and (e) collecting mass spectral data from the ionization of step (d) and identifying therefrom ion abundances of said modified biomolecular targets and any complexes formed between said binding agent and said modified biomolecular targets, wherein said ion abundances afford information for effecting said screening.

21. The method of claim 20 wherein the ion abundances of said ions of said modified biomolecular target and said complexes are compared to determine the selectivity of the binding interaction between said ligand and said targets.

22. The method of claim 20 wherein said biomolecular target is a nucleic acid.

23. The method of claim 20 wherein said mass modifying tags are polymeric.

24. The method of claim 23 wherein said polymers are a polyethylene glycol, polypropylene, polystyrene, cellulose, sephadex, dextran, peptide or polyacrylamide.

25. The method of claim 23 wherein said mass modifying tag is attached to the 3'-terminus, 5'-terminus or sugar-phosphate backbone of said biomolecular targets.

26. A method for screening a plurality of biomolecular targets against a combinatorial library of compounds comprising:

(a) providing n different biomolecular targets, wherein n is an integer greater than or equal to 2;

(b) modifying n! 1 of said biomolecular targets with mass modifying tags, wherein the mass to charge ratio of ions of about the same charge of said modified biomolecular targets are substantially distinguishable by mass spectrometry;

(c) combining said modified biomolecular targets with said combinatorial library of compounds;

(d) ionizing said combination from step c in a mass spectrometer to provide a plurality of ions; and (e) collecting mass spectral data from the ionization of step (d) and identifying therefrom ion abundances of said modified biomolecular targets and any complexes formed between said compounds and said modified biomolecular targets, wherein said ion abundances afford information for effecting said screening.

27. The method of claim 26 wherein the ion abundances of said ions of said modified biomolecular target and said complexes are compared to determine the selectivity of the binding interactions between said compounds and said targets.

28. The method of claim 26 wherein said biomolecular target is a nucleic acid.

29. The method of claim 26 wherein said mass modifying tags are polymeric.

30. The method of claim 26 wherein said mass modifying tag is attached to the 3'-terminus, 5'-terminus or sugar-phosphate backbone of said biomolecular targets.

31. A method of screening multiple biomolecular targets against a ligand comprising:

(a) providing at least two biomolecular targets which possess different masses such that the mass to charge ratio of ions of about the same charge of said biomolecular targets are substantially distinguishable by mass spectrometry;

(b) combining said bimolecular targets with said ligand;

(c) ionizing said combination of step (b) in a mass spectrometer to form a plurality of ions; and (d) collecting mass spectral data from the ionization of step c and identifying therefrom ion abundances of said biomolecular targets and any complexes formed between said ligand and said biomolecular targets, wherein said ion abundances afford information for effecting said screening.

32. The method of claim 31 wherein said ion abundances of said biomolecular target and said complexes are compared to determine the selectivity of the binding interactions between said bimolecular targets and said ligand.

33. The method of claim 31 wherein said biomolecular target is a nucleic acid.

34. The method of claim 31 wherein said nucleic acid is derived from prokaryotic or eukaryotic nucleic acids.

35. The method of claim 31 wherein said biomolecular targets comprise a mixture of proteins.

* * * * *

UNITED STATES PATENT AND TRADEMARK OFFICE
CERTIFICATE OF CORRECTION

PATENT NO. : 6,329,146 B1
DATED : December 11, 2001
INVENTOR(S) : Crooke et al.

It is certified that error appears in the above-identified patent and that said Letters Patent is hereby corrected as shown below:

Title page,
Item [56], OTHER PUBLICATIONS, (under Jonsson et al.) please delete "Redonance" and insert therefor -- Resonance --;

Column 2,
Line 31, please delete "apolymer" and insert therefor -- a polymer --;

Column 10,
Line 62, please delete "(KD)" and insert therefor -- ($K_D$) --;

Column 22,
Line 12, please delete "anoncovalent" and insert therefor -- a noncovalent --;

Column 25,
Line 46, please delete "tetaalkylammonium" and insert therefor
-- tetraalkylammonium --;

Column 28,
Line 5, please delete "be wildering" and insert therefor -- bewildering --;

Column 35,
Line 48, please delete "RNAIDNA" and insert therefor -- RNA/DNA --;

Column 45,
Line 25, please delete "of f" and insert therefor -- off --;

Column 47,
Line 24, please delete "22" and insert therefor -- 2217.8(w21)3-, --;

UNITED STATES PATENT AND TRADEMARK OFFICE
CERTIFICATE OF CORRECTION

PATENT NO. : 6,329,146 B1
DATED : December 11, 2001
INVENTOR(S) : Crooke et al.

It is certified that error appears in the above-identified patent and that said Letters Patent is hereby corrected as shown below:

<u>Column 52,</u>
Line 30, please delete "n!1" and insert therefor -- $n$-1 --;
Line 65, please delete "n!1" and insert therefor -- $n$-1 --;

Signed and Sealed this

Twentieth Day of August, 2002

Attest:

JAMES E. ROGAN
Attesting Officer *Director of the United States Patent and Trademark Office*

SEQUENCE LISTING

<160> NUMBER OF SEQ ID NOS: 2

<210> SEQ ID NO 1
<211> LENGTH: 27
<212> TYPE: RNA
<213> ORGANISM: Artificial Sequence
<220> FEATURE:
<223> OTHER INFORMATION: Description of Artificial Sequence:
      OLIGONUCLEOTIDE

<400> SEQUENCE: 1
ggcgucacac cuucggguga agucgcc                                          27

<210> SEQ ID NO 2
<211> LENGTH: 27
<212> TYPE: RNA
<213> ORGANISM: Artificial Sequence
<220> FEATURE:
<223> OTHER INFORMATION: Description of Artificial Sequence:
      OLIGONUCLEOTIDE

<400> SEQUENCE: 2
ggcgucacac cuucggguga agucgcc                                          27